United States Patent
Anderberg et al.

(10) Patent No.: US 10,324,093 B2
(45) Date of Patent: Jun. 18, 2019

(54) METHODS AND COMPOSITIONS FOR DIAGNOSIS AND PROGNOSIS OF RENAL INJURY AND RENAL FAILURE

(75) Inventors: Joseph Anderberg, Encinitas, CA (US); Jeff Gray, Solana Beach, CA (US); Paul McPherson, Encinitas, CA (US); Kevin Nakamura, Cardiff by the Sea, CA (US); James Patrick Kampf, San Diego, CA (US)

(73) Assignee: Astute Medical, Inc., San Diego, CA (US)

( * ) Notice: Subject to any disclaimer, the term of this patent is extended or adjusted under 35 U.S.C. 154(b) by 27 days.

(21) Appl. No.: 13/508,363

(22) PCT Filed: Nov. 5, 2010

(86) PCT No.: PCT/US2010/055730
§ 371 (c)(1),
(2), (4) Date: May 5, 2012

(87) PCT Pub. No.: WO2011/057147
PCT Pub. Date: May 12, 2011

(65) Prior Publication Data
US 2012/0231476 A1   Sep. 13, 2012

Related U.S. Application Data

(60) Provisional application No. 61/259,540, filed on Nov. 9, 2009, provisional application No. 61/259,140, filed on Nov. 7, 2009, provisional application No. 61/259,142, filed on Nov. 7, 2009, provisional application No. 61/259,141, filed on Nov. 7, 2009, provisional application No. 61/259,511, filed on Nov. 9, 2009, provisional application No. 61/259,163, filed on Nov. 7, 2009, provisional application No. 61/259,143, filed on Nov. 7, 2009.

(51) Int. Cl.
*G01N 33/53* (2006.01)
*G01N 33/68* (2006.01)

(52) U.S. Cl.
CPC ..... *G01N 33/6842* (2013.01); *G01N 33/6893* (2013.01); *G01N 2333/96413* (2013.01); *G01N 2800/347* (2013.01); *G01N 2800/56* (2013.01)

(58) Field of Classification Search
CPC ......... G01N 2800/347; G01N 2800/56; G01N 33/6863; G01N 33/6842; G01N 2333/96413
See application file for complete search history.

(56) References Cited

U.S. PATENT DOCUMENTS

| 6,218,122 B1 | 4/2001 | Friend et al. |
|---|---|---|
| 6,664,385 B1 | 12/2003 | Sanicola-Nadel et al. |
| 6,784,154 B2 | 8/2004 | Westenfelder |
| 6,861,404 B1 | 3/2005 | Cohen et al. |
| 6,941,172 B2 | 9/2005 | Nachum |
| 7,138,230 B2 | 11/2006 | Hu et al. |
| 7,141,382 B1 | 11/2006 | Parikh et al. |
| 7,235,358 B2 | 6/2007 | Wohlgemuth et al. |
| 7,608,413 B1 | 10/2009 | Joseloff et al. |
| 7,662,578 B2 | 2/2010 | Devarajan |
| 7,981,684 B2 | 7/2011 | Levin et al. |
| 7,998,744 B2 | 8/2011 | Stevenson et al. |
| 8,008,008 B2 | 8/2011 | Parr et al. |
| 8,071,293 B2 | 12/2011 | High et al. |
| 8,080,394 B2 | 12/2011 | Levy et al. |
| 8,241,861 B1 | 8/2012 | Heinecke et al. |
| 2003/0003588 A1 | 1/2003 | Comper |
| 2004/0053309 A1 | 3/2004 | Holt et al. |
| 2004/0106155 A1 | 6/2004 | Comper |
| 2005/0002934 A1 | 1/2005 | Reed |
| 2005/0048033 A1 | 3/2005 | Fraser et al. |
| 2005/0112688 A1 | 5/2005 | Hu et al. |
| 2005/0137481 A1 | 6/2005 | Sheard et al. |
| 2005/0148029 A1 | 7/2005 | Buechler et al. |
| 2005/0158801 A1 | 7/2005 | Hu et al. |
| 2005/0256075 A1 | 11/2005 | Alitalo et al. |
| 2005/0272101 A1 | 12/2005 | Devarajan et al. |
| 2006/0003327 A1 | 1/2006 | Achiron et al. |

(Continued)

FOREIGN PATENT DOCUMENTS

| CN | 1791797 A | 6/2006 |
|---|---|---|
| EP | 0828159 A1 | 3/1998 |

(Continued)

OTHER PUBLICATIONS

Luminex Press Release; 2002; retrieved on Nov. 5, 2013 from http://www.sec.gov/Archives/edgar/data/1033905/000095014402009542/g78279exv99w1.txt.*
Hang et al Journal of Immunology, 1999, 162: 3037-3044.*
International Preliminary Report on Patentability dated Sep. 7, 2012 in PCT/US2011/026384.
Non-Final Office Action issued by the US Patent and Trademark Office dated Nov. 16, 2012 in U.S. Appl. No. 13/389,351.
Non-Final Office Action issued by the US Patent and Trademark Office dated Nov. 27, 2012 in U.S. Appl. No. 13/130,474.
Flynn et al., Urinary excretion of beta2-glycoprotein-1 (apolipoprotein H) and other markers of tubular malfunction in "non-tubular" renal disease J Clin Pathol. Jul. 1992;45(7):561-567.

(Continued)

*Primary Examiner* — Julie Wu
*Assistant Examiner* — Carmencita M Belei
(74) *Attorney, Agent, or Firm* — Womble Bond Dickinson (US) LLP

(57) ABSTRACT

The present invention relates to methods and compositions for monitoring, diagnosis, prognosis, and determination of treatment regimens in subjects suffering from or suspected of having a renal injury. In particular, the invention relates to using a one or more assays configured to detect a kidney injury marker selected from the group consisting of Cathepsin B, Renin, Dipeptidyl Peptidase IV, Neprilysin, Beta-2-microglobulin, Carbonic anhydrase IX, and C-X-C motif chemokine 2 as diagnostic and prognostic biomarkers in renal injuries.

5 Claims, No Drawings

Specification includes a Sequence Listing.

(56) References Cited

U.S. PATENT DOCUMENTS

| | | |
|---|---|---|
| 2006/0057066 A1 | 3/2006 | Natsoulis et al. |
| 2006/0088823 A1 | 4/2006 | Haab et al. |
| 2006/0204951 A1 | 9/2006 | Folkman et al. |
| 2006/0205625 A1 | 9/2006 | Straub et al. |
| 2006/0223077 A1 | 10/2006 | Ni et al. |
| 2006/0240437 A1 | 10/2006 | Krolewski et al. |
| 2006/0246485 A1 | 11/2006 | Sarwal et al. |
| 2007/0031905 A1 | 2/2007 | Shariat |
| 2007/0087387 A1 | 4/2007 | Devarajan et al. |
| 2007/0093969 A1 | 4/2007 | Mendrick et al. |
| 2007/0105142 A1 | 5/2007 | Wilhelm |
| 2007/0112327 A1 | 5/2007 | Yun et al. |
| 2007/0154897 A1 | 7/2007 | Yen et al. |
| 2007/0248989 A1 | 10/2007 | Devarajan |
| 2007/0249002 A1 | 10/2007 | Hu et al. |
| 2007/0278989 A1 | 10/2007 | Devarajan |
| 2008/0014644 A1 | 1/2008 | Barasch et al. |
| 2008/0038192 A1 | 2/2008 | Gervais |
| 2008/0038269 A1 | 2/2008 | Susan |
| 2008/0090304 A1 | 4/2008 | Barasch et al. |
| 2008/0133141 A1 | 6/2008 | Frost |
| 2008/0153092 A1 | 6/2008 | Kienle et al. |
| 2008/0206794 A1 | 8/2008 | Hu et al. |
| 2008/0254483 A1 | 10/2008 | Darbouret et al. |
| 2008/0254485 A1 | 10/2008 | Valkirs et al. |
| 2009/0022730 A1 | 1/2009 | Raulf et al. |
| 2009/0047689 A1 | 2/2009 | Kolman et al. |
| 2009/0081713 A1 | 3/2009 | Klein et al. |
| 2009/0088409 A1 | 4/2009 | Charlton |
| 2009/0090856 A1 | 4/2009 | Grant et al. |
| 2009/0148539 A1 | 6/2009 | Elias et al. |
| 2009/0176656 A1 | 7/2009 | Halloran |
| 2009/0197287 A1 | 8/2009 | Hu et al. |
| 2009/0203588 A1 | 8/2009 | Willman et al. |
| 2009/0220526 A1 | 9/2009 | Hamid |
| 2009/0258002 A1 | 10/2009 | Barrett et al. |
| 2009/0298073 A1 | 12/2009 | Gerhold et al. |
| 2009/0298106 A1 | 12/2009 | Hooper |
| 2010/0022627 A1 | 1/2010 | Scherer |
| 2010/0081148 A1 | 4/2010 | Singbartl et al. |
| 2010/0190164 A1 | 7/2010 | Tammen et al. |
| 2010/0240078 A1 | 9/2010 | Lee et al. |
| 2010/0267041 A1 | 10/2010 | Shuber et al. |
| 2011/0065608 A1 | 3/2011 | Labrie et al. |
| 2011/0104726 A1 | 5/2011 | Valkirs et al. |
| 2011/0174062 A1 | 7/2011 | Anderberg et al. |
| 2011/0195429 A1 | 8/2011 | Anderberg et al. |
| 2011/0201038 A1 | 8/2011 | Anderberg et al. |
| 2011/0207161 A1 | 8/2011 | Anderberg et al. |
| 2012/0190044 A1 | 7/2012 | Anderberg et al. |
| 2012/0190051 A1 | 7/2012 | Anderberg et al. |
| 2013/0035290 A1 | 2/2013 | Elias et al. |

FOREIGN PATENT DOCUMENTS

| | | |
|---|---|---|
| EP | 1905846 A2 | 4/2008 |
| EP | 2261660 A1 | 12/2010 |
| EP | 2480882 A1 | 8/2012 |
| EP | 2513649 A1 | 10/2012 |
| RU | 2180965 C1 | 3/2002 |
| SU | 1429031 A1 | 10/1988 |
| WO | 1998055508 A2 | 12/1998 |
| WO | 2003054004 A2 | 7/2003 |
| WO | 2003075016 A1 | 9/2003 |
| WO | 2004005934 A2 | 1/2004 |
| WO | 2005087264 A1 | 9/2005 |
| WO | 2006083986 A3 | 8/2006 |
| WO | 20060839836 A2 | 8/2006 |
| WO | 2007013919 A2 | 2/2007 |
| WO | 2007041623 A2 | 4/2007 |
| WO | 2007054975 A1 | 5/2007 |
| WO | 2008060607 A2 | 5/2008 |
| WO | 2008084331 A2 | 7/2008 |
| WO | 2008104804 A2 | 9/2008 |
| WO | 2008116867 A1 | 10/2008 |
| WO | 2008122670 A2 | 10/2008 |
| WO | 2008154238 A1 | 12/2008 |
| WO | 2009038742 A2 | 3/2009 |
| WO | 2010025424 A1 | 3/2010 |
| WO | 2010025434 A1 | 3/2010 |
| WO | 2010048346 A1 | 4/2010 |
| WO | 2010048347 A2 | 4/2010 |
| WO | 2010054389 A1 | 5/2010 |
| WO | 2010091236 A1 | 8/2010 |
| WO | 2010111746 A1 | 10/2010 |
| WO | 2010128158 A1 | 11/2010 |
| WO | 2011035323 A1 | 3/2011 |
| WO | 2011075744 A1 | 6/2011 |

OTHER PUBLICATIONS

Kasahara et al Clinical Significance of Serum Oxidized Low-Density Lipoprotein/beta2-Giycoprotein I Complexes in Patients with Chronic Renal Diseases. Nephron Clin Pract. 2004;98(1):15-24.

Lapsley et al., Beta 2-glycoprotein-1 (apolipoprotein H) excretion in chronic renal tubular disorders: Comparison with other protein markers of tubular malfunction. J Clin Pathol. Oct. 1991;44(10):812-816.

Matsuda et al., Beta 2-Glycoprotein I-Dependent and -Independent Anticardiolipin Antibody in Patients with End-Stage Renal Disease. Thromb Res. Oct. 15, 1993;72(2):109-117.

Ramirez et al., Prospective Study on Autoantibodies Against Apolipoprotein H (beta2GPI) in Several Clinical Parameters From Patients With Terminal Renal Failure and Functioning Renal Transplants. Transplant Proc. Jul.-Aug. 2009;41(6):2370-2.

Zheng et al., Antiphospholipid antibody profiles in lupus nephritis with glomerular microthrombosis: a prospective study of 124 cases. Arthritis Res Ther. 2009;11(3):1-9.

Kehoe et al., Elevated Plasma Renin Activity Associated with Renal Dysfunction, Nephron, 1986, 44:51-57 (abstract only).

International Search Report and Written Opinion issued in PCT/US2010/055730 dated Feb. 8, 2011.

Response dated May 16, 2012 to Extended European Search Report and Written Opinion in PCT/US2009/055449.

Extended European Search Report and Written Opinion dated Feb. 23, 2012 in PCT/US2009/065419.

Extended European Search Report and Written Opinion dated Jul. 27, 2012 in PCT/US2010/023294.

Extended European Search Report and Written Opinion dated Oct. 24, 2011 in PCT/US2009/055449.

Extended European Search Report and Written Opinion dated Feb. 22, 2012 in PCT/US2009/055460.

Extended European Search Report and Written Opinion dated Jul. 9, 2012 in PCT/US2009/061561.

Extended European Search Report and Written Opinion dated Aug. 23, 2012 in PCT/US2009/061562.

Extended European Search Report and Written Opinion dated Jul. 9, 2012 in PCT/US2010/023292.

Extended European Search Report and Written Opinion dated Aug. 23, 2012 in PCT/US2010/023297.

Extended European Search Report and Written Opinion dated Jun. 8, 2012 in PCT/US2009/063906.

International Preliminary Report on Patentability dated Oct. 21, 2011 in PCT/US2010/023297.

International Preliminary Report on Patentability dated Mar. 29, 2011 in PCT/US2010/049234.

International Preliminary Report on Patentability dated May 18, 2012 in PCT/US2010/055730.

International Preliminary Report on Patentability dated Mar. 10, 2011 in PCT/US2009/055449.

International Preliminary Report on Patentability dated Mar. 10, 2011 in PCT/US2009/055460.

International Preliminary Report on Patentability dated Aug. 16, 2012 in PCT/US2011/023830.

International Preliminary Report on Patentability dated Aug. 16, 2012 in PCT/US2011/023831.

(56) References Cited

OTHER PUBLICATIONS

International Preliminary Report on Patentability dated Aug. 16, 2012 in PCT/US2011/023832.
International Preliminary Report on Patentability dated Apr. 5, 2012 in PCT/US2010/049695.
International Preliminary Report on Patentability dated May 5, 2011 in PCT/US2009/061561.
International Preliminary Report on Patentability dated May 5, 2011 in PCT/US2009/061562.
International Preliminary Report on Patentability dated Jun. 3, 2011 in PCT/US2009/065419.
International Preliminary Report on Patentability dated Jul. 5, 2012 in PCT/US2010/061377.
International Preliminary Report on Patentability dated Aug. 18, 2011 in PCT/US2010/023292.
International Preliminary Report on Patentability dated Aug. 18, 2011 in PCT/US2010/023294.
International Preliminary Report on Patentability dated May 10, 2011 in PCT/US2009/063906.
International Search Report and Written Opinion dated Dec. 3, 2010 in PCT/US2010/049234.
International Search Report and Written Opinion dated Feb. 8, 2011 in PCT/US2010/055730.
International Search Report and Written Opinion dated Oct. 28, 2010 in PCT/US2010/044772.
International Search Report and Written Opinion dated Oct. 8, 2010 in PCT/US2010/044708.
International Search Report and Written Opinion dated Dec. 10, 2009 in PCT/US2009/055449.
International Search Report and Written Opinion dated Dec. 31, 2009 in PCT/US2009/055460.
International Search Report and Written Opinion dated Dec. 3, 2010 in PCT/US2010/049695.
International Search Report and Written Opinion dated Jan. 20, 2010 in PCT/US2009/061561.
International Search Report and Written Opinion dated Apr. 13, 2010 in PCT/US2009/061562.
International Search Report and Written Opinion dated Mar. 30, 2010 in PCT/US2009/065419.
International Search Report and Written Opinion dated Mar. 8, 2011 in PCT/US2010/061377.
International Search Report and Written Opinion dated Apr. 30, 2010 in PCT/US2010/023292.
International Search Report and Written Opinion dated Apr. 22, 2010 in PCT/US2010/023294.
International Search Report and Written Opinion dated Jun. 3, 2010 in PCT/US2010/023297.
International Search Report and Written Opinion dated Jan. 15, 2010 in PCT/US2009/063906.
International Search Report and Written Opinion dated Nov. 18, 2010 in PCT/US2010/046910.
International Search Report and Written Opinion dated Jan. 18, 2012 in PCT/US2011/053015.
International Search Report and Written Opinion dated Feb. 24, 2012 in PCT/US2011/055055.
International Search Report and Written Opinion dated Jan. 19, 2011 in PCT/US2010/055721.
International Search Report and Written Opinion dated May 10, 2012 in PCT/US2012/020571.
International Search Report and Written Opinion dated Apr. 27, 2011 in PCT/US2011/023830.
International Search Report and Written Opinion dated Apr. 27, 2011 in PCT/US2011/023831.
International Search Report and Written Opinion dated Apr. 29, 2011 in PCT/US2011/023832.
International Search Report and Written Opinion dated May 17, 2011 in PCT/US2011/026384.
International Search Report and Written Opinion dated Jun. 3, 2011 in PCT/US2011/026759.
International Search Report and Written Opinion dated Sep. 7, 2012 in PCT/US2012/043279.
International Search Report and Written Opinion dated Dec. 15, 2011 in PCT/US2011/001126.
International Search Report and Written Opinion dated Nov. 25, 2011 in PCT/US2011/001127.
International Search Report and Written Opinion dated Nov. 25, 2011 in PCT/US2011/001128.
International Search Report and Written Opinion dated Nov. 25, 2011 in PCT/US2011/001125.
International Search Report and Written Opinion dated Jun. 20, 2012 in PCT/US2012/020572.
International Search Report and Written Opinion dated May 2, 2012 in PCT/US2012/022926.
International Search Report and Written Opinion dated Sep. 21, 2012 in PCT/US2012/045583.
Non Final Office Action issued by the USPTO in U.S. Appl. No. 13/061,446 dated Oct. 12, 2012.
Abd El Latif et al., Urinary epidermal growth factor excretion: A useful prognostic marker for progression of renal damage in children. J Med Sci Oct. 2007; 7(7): 1171-1176.
Abou-Shousha and Youssef, Interleukin-2 Regulatory Effect on P-Selectin and Interleukin-8 Production in Patients with Chronic Renal Failure. Egypt J Immunol. 2006;13(1):11-18.
Akcay et al., Mediators of Inflammation in Acute Kidney Injury. Mediators Inflamm. 2009;2009:137072 (12 pp).
Albright, Acute Renal Failure: A Practical Update. Mayo Clin. Proc. Jan. 2001;76(1):67-74.
Anders et al., Chemokines and chemokine receptors are involved in the resolution or progression of renal disease. Kidney Int. Feb. 2003;63(2):401-415.
Anilkumar et al., Trimeric assembly of the C-terminal region of Thrombospondin-1 or Thrombospondin-2 is necessary for cell spreading and fascin spike organisation. J Cell Sci. Jun. 1, 2002;115(Pt 11):2357-2366.
Arribas and Esselens, ADAM17 as a Therapeutic Target in Multiple Diseases. Curr Pharm Des. 2009;15(20):2319-2335.
Arrizabalaga et al., Tubular and Interstitial Expression of ICAM-1 as a Marker of Renal Injury in IgA Nephropathy. Am J Nephrol May-Jun. 2003;23(3):121-128.
Bagshaw et al., Urinary biomarkers in septic acute kidney injury. Intensive Care Med. Jul. 2007;33(7):1285-1296.
Bajwa et al., Immune Mechanisms and Novel Pharmacological Therapies of Acute Kidney Injury. Curr Drug Targets Dec. 2009;10(12):1196-1204.
Barrera-Chimal et al., Hsp72 is an early and sensitive biomarker to detect acute kidney injury. EMBO Mol Med. Jan. 2011;3(1):5-20.
Beushausen, NWG Biomarker Objectives. ILSI Health and Environmental Sciences Institute, ILSI-HESI Annual Meeting 2006:17 pp.
Bicik et al., Role of Transforming Growth Factor-.beta.2 in, and a Possible Transforming Growth Factor-beta2 Gene Polymorphism as a Marker of, Renal Dysfunction in Essential Hypertension: A Study in Turkish Patients, Current Therapeutic Research, 2005;44(4):266-278.
Biotrin International, Biotrin Biomarkers: How late do you want to detect preclinical kidney damage? Biotrin's acute kidney injury test (AKI Test). Biotrin's Preclinical Kidney Biomarkers: 8 pp.
Bonomini et al., Serum Levels of Soluble Adhesion Molecules in Chronic Renal Failure and Dialysis Patients. Nephron. Aug. 1998;79(4):399-407.
Bonventre and Zuk, Ischemic acute renal failure: An inflammatory disease? Kidney Int. Aug. 2004;66(2):480-485.
Bonventre, Dedifferentiation and Proliferation of Surviving Epithelial Cells in Acute Renal Failure. J Am Soc Nephrol Jun. 2003;14 Suppl 1:S55-S61.
Bonventre, Pathophysiology of Acute Kidney Injury: Roles of Potential Inhibitors of Inflammation. Contrib Nephrol. 2007; 156: 39-46.
Burne et al., IL-1 and TNF independent pathways mediate ICAM-1/VCAM-1 up-regulation in ischemia reperfusion injury. J Leukoc Biol. Aug. 2001;70(2):192-198.

(56) References Cited

OTHER PUBLICATIONS

Burne-Taney and Rabb, The role of adhesion molecules and T cells in ischemic renal injury. Curr Opin Nephrol Hypertens. Jan. 2003;12(1):85-90.
Canani et al., The Fatty Acid-Binding Protein-2 A54T Polymorphism Is Associated With Renal Disease in Patients With Type 2 Diabetes. Diabetes Nov. 2005;54(11):3326-3330.
Catania et al., Role of matrix metalloproteinases in renal pathophysiologies. Am J Physiol Renal Physiol Mar. 2007;292(3):F905-F911.
Coca et al., Biomarkers for the diagnosis and risk stratification of acute kidney injury: A systematic review. Kidney Int May 2008;73(9):1008-1016.
Cruz et al., North East Italian Prospective Hospital Renal Outcome Survey on Acute Kidney Injury (NEiPHROS-AKI): Targeting the Problem with the RIFLE Criteria. Clin J Amer. Soc. Nephrol. May 2007;2(3):418-425.
Daha and Van Kooten, Is the proximal tubular cell a proinflammatory cell? Nephrol Dial Transplant 2000;15 Suppl 6:41-43.
De Sa et al., Leukocyte, platelet and endothelial activation in patients with acute renal failure treated by intermittent hemodialysis. Am J Nephrol. Jul.-Aug. 2001;21(4):264-273.
Devarajan and Williams, Proteomics for Biomarker Discovery in Acute Kidney Injury. Semin Nephrol. Nov. 2007;27(6):637-651.
Devarajan, Cellular and molecular derangements in acute tubular necrosis. Curr Opin Pediatr. Apr. 2005;17(2):193-199.
Devarajan, Novel biomarkers for the early prediction of acute kidney injury. Cancer Therapy Sep. 2005;3:477-488.
Devarajan, Update on Mechanisms of Ischemic Acute Kidney Injury. J Am Soc Nephrol. Jun. 2006;17(6):1503-1520.
Domanski et al., Purine and Cytokine Concentrations in the Renal Vein of the Allograft During Reperfusion. Transplant Proc. Jun. 2007;39(5):1319-1322.
FDA, European Medicines Agency to Consider Additional Test Results When Assessing New Drug Safety—Collaborative effort by FDA and EMEA expected to yield additional safety data. http://www.natap.org/2008/newsUpdates/071608_01.htm.
Ferguson et al., Biomarkers of nephrotoxic acute kidney injury. Toxicology Mar. 20, 2008;245(3):182-193.
Frangogiannis, Chemokines in ischemia and reperfusion. Thromb Haemost May 2007;97(5):738-747.
Furuichi et al., Chemokine/chemokine receptor-mediated inflammation regulates pathologic changes from acute kidney injury to chronic kidney disease. Clin Exp Nephrol Feb. 2009;13(1):9-14.
Furuichi et al., Roles of chemokines in renal ischemia/reperfusion injury. Front Biosci. May 1, 2008;13:4021-4028.
Galkina and Ley, Leukocyte Recruitment and Vascular Injury in Diabetic Nephropathy. J Am Soc Nephrol. Feb. 2006;17(2):368-377.
Garcia et al., Adenosine A2A receptor activation and macrophagemediated experimental glomerulonephritis. FASEB J. Feb. 2008;22(2):445-454.
Gbadegesin et al., Plasma and urinary soluble adhesion molecule expression is increased during first documented acute pyelonephritis. Arch Dis Child. Mar. 2002;86(3):218-221.
Goes et al., Effect of Recombinant Human Insulin-Like Growth Factor-1 on the Inflammatory Response to Acute Renal Injury. J Am Soc Nephrol. May 1996;7(5):710-720.
Grigoryev et al., The Local and Systemic Inflammatory Transcriptome after Acute Kidney Injury. J Am Soc Nephrol. Mar. 2008;19(3):547-558.
Gümüs et al., Serum Levels of Total Acid Phosphatase, Prostatic Acid Phosphatase, Total and Free Prostate-Specific Antigen in Patients Within Chronic Hemodialysis Program. Braz J Urol, Mar.-Apr. 2001;27(2):133-135.
Gupta et al., Role of Protein C in Renal Dysfunction after Polymicrobial Sepsis. J Am Soc Nephrol. Mar. 2007;18(3):860-867.
Han et al, Urinary biomarkers in the early diagnosis of acute kidney injury, Kidney Int. Apr. 2008;73(7):863-869.
Han et al., Upregulation of hyaluronan and its binding receptors in an experimental model of chronic cyclosporine nephropathy. Nephrology (Carlton). Mar. 2010;15(2):216-224.
Han, Biomarkers for Early Detection of Acute Kidney Injury. Nephrology Rounds Apr. 2008;6(4):6 pp.
Harris et al., Growth Factors and Cytokines in Acute Renal Failure. Adv Ren Replace Ther. Apr. 1997;4(2 Suppl):43-53.
He et al., Interleukin-18 binding protein transgenic mice are protected against ischemic acute kidney injury. Am J Physiol Renal Physiol. Nov. 2008;295(5):F1414-F1421.
Herget-Rosenthal et al., Early detection of acute renal failure by serum cystatin C. Kidney Int. Sep. 2004;66(3):1115-1122.
Hidaka et al., Urinary clusterin levels in the rat correlate with the severity of tubular damage and may help to differentiate between glomerular and tubular injuries. Cell Tissue Res. Dec. 2002;310(3):289-296.
Hirschberg et al. Factors Predicting Poor Outcome in Patients with Acute Renal Failure (ARF). J. Am. Soc. Nephrol. Sep. 1, 1996;7(9):1374.
Hoste et al., RIFLE criteria for acute kidney injury are associated with hospital mortality in critically ill patients: a cohort analysis. Crit Care, 2006;10(3):R73 (10 pages).
Hugo and Daniel, Thrombospondin in Renal Disease. Nephron Exp Nephrol. 2009;111(3):e61-e66.
Hugo et al. ,Thrombospondin 1 precedes and predicts the development of tubulointerstitial fibrosis in glomerular disease in the rat. Kidney Int. Feb. 1998;53(2):302-311.
Jang and Rabb, The innate immune response in ischemic acute kidney injury. Clin Immunol. Jan. 2009;130(1):41-50.
Jonsson, The role of fibroblast growth factor 23 in renal disease. Nephrol. Dial. Transplant Mar. 2005;20(3):479-482.
Julian et al., Sources of Urinary Proteins and their Analysis by Urinary Proteomics for the Detection of Biomarkers of Disease. Proteomics Clin Appl., 2009;3(9):1029-1043.
Kadiroglu et al., The Evaluation of Effects of Demographic Features, Biochemical Parameters, and Cytokines on Clinical Outcomes in Patients with Acute Renal Failure. Ren Fail. 2007;29(4):503-508.
Kalousova et al., Soluble Receptor for Advanced Glycation End Products in Patients With Decreased Renal Function. Am. J. Kidney Dis.Mar. 2006;47(3): 406-411.
Kamata et al., Up-regulation of glomerular extracellular matrix and transforming growth factor-beta expression in RF/J mice. Kidney Int. Mar. 1999;55(3):864-876.
Kellum et al. Definition and Classification of Acute Kidney Injury. Nephron Clin Pract 2008;109(4):c182-c187.
Kellum., Acute kidney injury, Crit Care Med, 2008;36(4):S141-S145.
Keyes and Bagshaw, Early diagnosis of acute kidney injury in critically ill patients. Expert Rev Mol Diagn. Jul. 2008;8(4):455-464.
Khanna et al., Expression of TGF-beta and fibrogenic genes in transplant recipients with tacrolimus and cyclosporine nephrotoxicity. Kidney Int. Dec. 2002;62(6):2257-2263.
Kharasch et al., Gene Expression Profiling of Nephrotoxicity from the Sevoflurane Degradation Product Fluoromethyl-2,2-difluoro-1-(trifluoromethyl)vinyl Ether ("Compound A") in Rats. Toxicol Sci. Apr. 2006;90(2):419-431.
Kiley and Chevalier, Urinary biomarkers: The future looks promising. Kidney Int. Jul. 2009;76( 2): 133-134.
Kilis-Pstrusinska et al., [Levels of selected soluble adhesion molecules in blood serum of children with chronic glomerulonephritis]. Pol Merkur Lekarski. Apr. 2001;10(58):247-249.
Kilis-Pstrusinska et al., Serum levels of soluble adhesion molecules in children with glomerulonephritis (GN). Nephrol Dialysis Transplant. Jun. 2001;16(6):A62.
Kinsey et al., Inflammation in Acute Kidney Injury. Nephron Exp Nephrol. 2008; 109(4):e102-e107.
Koo et al., Cadaver versus living donor kidneys: Impact of donor factors on antigen induction before transplantation. Kidney Int. Oct. 1999;56(4):1551-1559.

(56) References Cited

OTHER PUBLICATIONS

Landray et al., Inflammation, Endothelial Dysfunction, and Platelet Activation in Patients With Chronic Kidney Disease: The Chronic Renal Impairment in Birmingham (CRIB) Study. Am J Kidney Dis. Feb. 2004;43(2):244-253.
Lang et al., Heat Shock Protein 60 Is Released in Immune-Mediated Glomerulonephritis and Aggravates Disease: In Vivo Evidence for an Immunologic Danger Signal. J Am Soc Nephrol. Feb. 2005;16(2):383-391.
Larsson et al., Circulating concentration of FGF-23 increases as renal function declines in patients with chronic kidney disease, but does not change in response to variation in Phosphate intake in healthy volunteers. Kidney Int.Dec. 2003;64(6):2272-2279.
Liu et al., Predictive and pathogenetic value of plasma biomarkers for acute kidney injury in patients with acute lung injury. Crit Care Med Dec. 2007;35(12):2755-2761.
Liu et al., Serum Interleukin-6 and interleukin-8 are early biomarkers of acute kidney injury and predict prolonged mechanical ventilation in children undergoing cardiac surgery: a case-control study. Critical Care 2009;13(4):R104 (9 pp.).
Lopes-Virella et al., Urinary high density lipoprotein in minimal change glomerular disease and chronic glomerulopathies. Clin Chim Acta. May 16, 1979;94(1):73-81.
Lu et al., Increased Macrophage Infiltration and Fractalkine Expression in Cisplatin-Induced Acute Renal Failure in Mice. J Pharmacol Exp Ther. Jan. 2008;324(1):111-117.
Malyszko et al., Visfatin and apelin, new adipocytokines, and their relation to endothelial function in patients with chronic renal failure. Adv Med Sci. 2008;53(1):32-36.
Matousovic et al., IgA-containing immune complexes in the urine of IgA nephropathy patients. Nephrol Dial Transplant Sep. 2006;21(9):2478-2484.
Mattes, Experience With a Biomarker Consortium. CPath Predictive Safety Training Consortium, Critical Path Institute:48 pp.
Melnikov et al., Impaired IL-18 processing protects caspase-1-deficient mice from ischemic acute renal failure. J Clin Invest, May 2001;107(9):1145-1152.
Milford et al., Prognostic Markers in Diarrhoea-Associated Haemolytic-Uraemic Syndrome: Initial Neutrophil Count, Human Neutrophil Elastase and Von Willebrand Factor Antigen. Nephrol Dial Transplant 1991;6(4):232-237.
Montagna et al., Impairment of cellular redox status and membrane protein activities in kidneys from rats with ischemic acute renal failure. Biochim Biophys Acta Aug. 14, 1998;1407(2):99-108.
Musial et al., Soluble adhesion molecules in chronic renal failure (CRF) children treated conservatively. Nephrol Dialysis Transplant. 2002:17(Abstracts Suppl 1):232.
Nguyen et al., Heparin-Binding EGF-Like Growth Factor Is Up-Regulated in the Obstructed Kidney in a Cell- and Region-Specific Manner and Acts to Inhibit Apoptosis. Am J Pathol. Mar. 2000;156(3):889-898.
Nishiyama et al., Up-Regulation of Galectin-3 in Acute Renal Failure of the Rat. Am J Pathol. Sep. 2000;157(3):815-823.
Ohno et al., Prognostic significance of tenascin-C expression in clear cell renal cell carcinoma. Oncol Rep. 2008;20(3):511-516.
Ozer et al., A panel of urinary biomarkers to monitor reversibility of renal injury and a serum marker with improved potential to assess renal function. Nat Biotechnol. May 2010;28(5):486-494.
Parikh and Devarajan, New biomarkers of acute kidney injury. Crit Care Med 2008;36(4 Suppl):S159-S165.
Parikh et al., Urinary IL-18 is an early predictive biomarker of acute kidney injury after cardiac surgery. Kidney Int, 2006;70(1):199-203.
Perco et al., Protein biomarkers associated with acute renal failure and chronic kidney disease. Eur J Clin Invest. Nov. 2006;36(11):753-763.
Picard et al., Origin of renal myofibroblasts in the model of unilateral ureter obstruction in the rat. Histochem Cell Biol. Jul. 2008;130(1):141-155.
Price, Abrupt Changes in Prostate-Specific Antigen Concentration in Acute Renal Failure. Clin Chem. Jan. 1993;39(1):161-162.
Prozialeck and Edwards, Cell Adhesion Molecules in Chemically-Induced Renal Injury. Pharmacol Ther. Apr. 2007;114(1):74-93.
Radford et al. Predicting renal outcome in IgA nephropathy. J Am Soc Nephrol Feb. 1997;8(2):199-207.
Ramesh and Reeves, TNF-α mediates chemokine and cytokine expression and renal injury in cisplatin nephrotoxicity. J. Clin. Invest. Sep. 2002;110(6):835-842.
Ramesh et al., Endotoxin and cisplatin synergistically induce renal dysfunction and cytokine production in mice. Am J Physiol Renal Physiol. Jul. 2007;293(1):F325-F332.
Ramirez et al., Prospective Study on Autoantibodies Against Apolipoprotein H ( B2GPI) in Several Clinical Parameters From Patients With Terminal Renal Failure and Functioning Renal Transplants. Transplantation Proceedings Jul. 2009;41(6):2370-2372.
Ricci et al., The RIFLE criteria and mortality in acute kidney injury: A systematic review. Kidney Int Mar. 2008;73(5):538-546.
Rosenkranz et al., P-selectin deficiency exacerbates experimental glomerulonephritis: a protective role for endothelial P-selectin in inflammation. J Clin Invest Mar. 1999;103(5):649-659.
Rouschop et al., Pre-transplant plasma and cellular levels of CD44 correlate with acute renal allograft rejection. Nephrol Dial Transplant Oct. 2005;20(10):2248-2254.
Rouschop et al., Renal expression of CD44 correlates with acute renal allograft rejection. Kidney Int. Sep. 2006;70(6):1127-1134.
Schena et al., EGF and MCP-1 Urinary Excretion Is a Suitable Prognostic Marker in Iga Nephropathy. J Am Soc of Nephrology; Meeting of the American Society of Nephrology. Sep. 1, 2002;13(Program and Abstracts Issue): 458A.
Schiffer et al., Activated Renal Macrophages Are Markers of Disease Onset and Disease Remission in Lupus Nephritis, J Immunol Feb. 1, 2008;180(3):1938-1947.
Schmaldienst et al., Angiogenin: a novel inhibitor of neutrophil-lactoferrin release during extracorporeal circulation. Kidney Blood Press Res. 2003;26(2):107-112.
Schmidt et al., Sexual hormone abnormalities in male patients with renal failure. Nephrol Dial Transplant. Mar. 2002;17(3):368-371.
Segawa et al., In situ expression and soluble form of P-selectin in human glomerulonephritis. Kidney Int. Oct. 1997;52(4):1054-1063.
Segerer et al., Chemokines, Chemokine Receptors, and Renal Disease: From Basic Science to Pathophysiologic and Therapeutic Studies. J Am Soc Nephrol Jan. 2000;11(1):152-176.
Severini and Aliberti, Diagnostic significance of urinary enzymes: Development of a high performance liquid chromatographic method for the measurement of urinary lysozyme. Clin Chim Acta Feb. 27, 1987;163(1):97-103.
Shlipak et al., Elevations of Inflammatory and Procoagulant Biomarkers in Elderly Persons With Renal Insufficiency. Circulation Jan. 2003;107(1):87-92.
Shoji et al., Plasma angiopoietin-like protein 3 (ANGPTL3) concentration is associated with uremic dyslipidemia. Atherosclerosis. Dec. 2009;207(2):579-584.
Stafford-Smith et al., Acute Kidney Injury and Chronic Kidney Disease After Cardiac Surgery. Adv Chronic Kidney Dis. Jul. 2008;15(3):257-277.
Stasko et al., Soluble P-Selectin During a Single Hemodialysis Session in Patients With Chronic Renal Failure and Erythropoietin Treatment. Clin Appl Thromb Hemost. Oct. 2007;13(4):410-415.
Stuard et al., Soluble adhesion molecules in chronic renal failure patients. Nephrol Dialysis Transplant. 1997;12(9): A100.
Supavekin et al., Differential gene expression following early renal ischemia/reperfusion. Kidney Int. May 2003;63(5):1714-1724.
Sutton et al., Injury of the renal microvascular endothelium alters barrier function after ischemia. Am J Physiol Renal Physiol Aug. 2003;285(2):F191-F198.
Sutton et al., Microvascular endothelial injury and dysfunction during ischemic acute renal failure. Kidney Int. Nov. 2002;62(5):1539-1549.
Sutton, Alteration of microvascular permeability in acute kidney injury. Microvasc Res. Jan. 2009;77(1):4-7.
Symon et al., The endogenous insulin-like growth factor system in radiocontrast nephropathy. Am. J. Physiol. Renal Physiol. Mar. 1998;274(3 Pt 2):F490-497.

(56) References Cited

OTHER PUBLICATIONS

Takada et al., The Cytokine-adhesion Molecule Cascade in Ischemia/Reperfusion Injury of the Rat Kidney. Inhibition by a Soluble P-selectin Ligand. J. Clin. Invest. Jun. 1997; 99(11):2682-2690.
Taulan et al., Comprehensive analysis of the renal transcriptional response to acute uranyl nitrate exposure. BMC Genomics Jan. 11, 2006;7(2) 14 pages.
Teppo et al., Soluble Intercellular Adhesion Molecule-1 (Sicam-1) after Kidney Transplantation: The Origin and Role of Urinary Sicam-1? Transplantation Apr. 27, 2001;71(8):1113-1119.
Thorburn et al., CXC and CC chemokines induced in human renal epithelial cells by inflammatory cytokines. APMIS Jul. 2009;117(7):477-487.
Timoshanko et al., Interleukin-12 from Intrinsic Cells Is an Effector of Renal Injury in Crescentic Glomerulonephritis. J. Am. Soc. Nephrol. Mar. 2001;12(3):464-471.
Torres et al., The ratio of epidermal growth factor to monocyte chemotactic peptide-1 in the urine predicts renal prognosis in IgA nephropathy. Kidney Int. Feb. 2008;73(3):327-333.
Vaidya and Bonventre, Mechanistic biomarkers for cytotoxic acute kidney injury. Expert Opin Drug Metab Toxicol. Oct. 2006;2(5):697-713.
Vaidya et al., Biomarkers of Acute Kidney Injury. Annu Rev Pharmacol Toxicol. Feb. 2008;48:463-493.
Vanhoutte et al., Biomarker discovery with SELDI-TOF MS in human urine associated with early renal injury: evaluation with computational analytical tools. Nephrol Dial Transplant Oct. 2007;22(10):2932-2943.
Villanueva et al., Ischemic acute renal failure induces the expression of a wide range of nephrogenic proteins. Am J Physiol Regul Integr Comp Physiol Apr. 2006;290(4):R861-R870.
Vonderscher, Biomarker of Drug Induced Kidney Injury Qualification for Regulatory Decision Making (CRADA). IOM/FDA, Silver Spring, MD Apr. 23, 2007:31 pp.
Waikar et al., Diagnosis, Epidemiology and Outcomes of Acute Kidney Injury. Clin J Am Soc Nephrol. May 2008;3(3):844-861.
Wan et al., The pathogenesis of septic acute renal failure. Curr Opin Crit Care Dec. 2003;9(6):496-502.
Wang et al., Netrin-1 and kidney injury. I. Netrin-1 protects against ischemia-reperfusion injury of the kidney. Am J Physiol Renal Physiol. Apr. 2008;294(4):F739-F747.
Wang et al., Validation of putative genomic biomarkers of nephrotoxicity in rats. Toxicology Apr. 18, 2008;246(2-3):91-100.
Wilson and Hadley, Urinary lysozyme. J Pediatr. Feb. 1950;36(2):199-211.
Winchester et al., Sorbents in Acute Renal Failure and End-Stage Renal Disease: Middle Molecule and Cytokine Removal. Blood Purif. 2004;22(1):73-77.
Yang et al. Frequency of anti-bactericidal/permeability-increasing protein (BPI) and anti-azurocidin in patients with renal disease. Clin. Exp. Immunol. Jul. 1996;105(1):125-131.
Yu et al., Urinary biomarkers trefoil factor 3 and albumin enable early detection of kidney tubular injury. Nat Biotechnol May 2010;128(5):470-477.
Yuen et al., Ischemic and Nephrotoxic Acute Renal Failure are Distinguished by their Broad Transcriptomic Responses. Physiol Genomics. May 16, 2006;25(3):375-386.
Zager et al. Proximal tubular cytochrome c efflux: Determinant, and potential marker, of mitochondrial injury. Kidney Int. Jun. 2004;65(6):2123-2134.
Mishra et al., Neutrophil gelatinase-associated lipocalin (NGAL) as a biomarker for acute renal injury after cardiac surgery. Lancet. Apr. 2-8, 2005;365(9466):1231-1238.
Stenvinkel et al., High Serum Hyaluronan Indicates Poor Survival in Renal Replacement Therapy. Am J Kidney Dis. Dec. 1999;34(6):1083-1088.
Tary-Lehmann et al., Enzyme-Linked Immunosorbent Assay Spot Detection of Interferon-Gamma and Interleukin 5-Producing Cells as a Predictive Marker for Renal Allograft Failure. Transplantation. Jul. 27, 1998;66(2):219-224.

Kimmel et al., Immunologic function and survival in hemodialysis patients. Kidney Int. Jul. 1998;54(1):236-244.
Simmons et al., Plasma cytokine levels predict mortality in patients with acute renal failure. Kidney Int. Apr. 2004;65(4):1357-1365.
Cai, Detection and Application for the biomarker of Rental Injury in Early Stage. Laboratory Med Clinic. Jun. 2005;2(3):124-127—incl Engl transl abstract only.
Jung et al., Diagnostic significance of urinary enzymes in detecting acute rejection crises in renal transplant recipients depending on expression of results illustrated through the example of alanine aminopeptidase. Clin Biochem. Aug. 1985;18(4):257-260.
Fried et al., Inflammatory and Prothrombotic Markers and the Progression of Renal Disease in Elderly Individuals. J Am Soc Nephrol. Dec. 2004;15(12):3184-3191.
Edelstein, Biomarkers of Acute Kidney Injury. Adv Chronic Kidney Dis.Jul. 2008;15(3)222-234.
Fujisaki et al., Infusion of radiocontrast agents induces exaggerated release of urinary endothelin in patients with impaired renal function. Clin Exp Nephrol. Dec. 2003;7(4):279-283.
Hirai et al., Plasma endothelin-1(ET-1) is a useful marker for renal dysfunction. Atheroscler Suppl. Jun. 19, 2006;7(3):60[Mo-P1:65].
Cottone et al., Endothelin-1 and F2-isoprostane relate to and predict renal dysfunction in hypertensive patients. Nephrol Dial Transpl. Feb. 2009;24(2):497-503.
Schulz et al., Endothelin-1 as an early prognostic marker in acute renal failure (ARF) and sepsis. Kidney Blood Press Res. 2000;23(3-5):341-342.
Song et al., Expression of TRAIL, DR4, and DR5 in kidney and serum from patients receiving renal transplantation. Transplant Proc. Jun. 2004;36(5):1340-1343.
Jayasena, "Aptamers: An Emerging Class of Molecules That Rival Antibodies in Diagnostics", Clin. Chem. 45: 1628-50 (1999).
Mezzano et al., Endothelial Cell Markers in Chronic Uremia: Relationship with Hemostatic Defects and Severity of Renal Failure. Thromb. Res. Dec. 15, 1997;88(6):465-472.
Tan et al., The level of urinary secretory immunoglobin A (sIgA) of patients with IgA nephropathy is elevated and associated with pathological phenotypes. Clin Exp Immunol. Apr. 2009;156(1):111-116.
Zhang et al., The level of serum secretory IgA of patients with IgA nephropathy is elevated and associated with pathological phenotypes. Nephrol Dial Transplant. Jan. 2008;23(1):207-212.
Choi et al., Expression of Vascular Endothelial Growth Factor-C and Its Receptor mRNA in the Rat Kidney With Ischemia-Reperfusion Injury. Clinical Kidney J. Jun. 2, 2011;4(Suppl 2):2 pages.
Cooper, Effect of Tobacco Smoking on Renal Function. Indian J Med Res Sep. 2006;124(3):261-268.
Senatorski et al., Urine activity of cathepsin B, collagenase and urine excretion of TGF-beta1 and fibronectin in membranous glomerulonephritis. Res Exp Med (Berl). Dec. 1998;198(4):199-206.
Schaefer et al., Urinary excretion of cathepsin B and cystatins as parameters of tubular damage. Kidney Int Suppl. Nov. 1994;47:S64-S67.
Kos et al., Cathepsins B,H and L and Their Inhibitors Stefin A and Cystatin C in Sera of Melanoma Patients. Clin Cancer Res. Oct. 1997;3(10):1815-1822.
Nambi et al., Down regulation of kidney neutral endopeptidase mRNA, protein and activity during acute renal failure: possible mechanism for ischemia-induced acute renal failure in rats? Mol Cell Biochem. Jul. 1999;197(1-2):53-59.
Li et al., Predictive value of RIFLE classification on prognosis of critically ill patients with acute kidney injury treated with continuous renal replacement therapy. Chin Med J (Engl). May 5, 2009;122(9):1020-1025.
Berahovich et al., Proteolytic activation of alternative CCR1 ligands in inflammation. J Immunol. Jun. 1, 2005;174(11):7341-7351.
Hatta et al., Cytokine Array Comparisons of Plasma from Cycling Fertile Women on Cycle Day 5 and Ovulation. Am J Reprod Immunol. Sep. 2009;62(3):158-164.

(56) References Cited

OTHER PUBLICATIONS

Voshol et al., Evaluation of Biomarker Discovery Approaches to Detect Protein Biomarkers of Acute Renal Allograft Rejection. J Proteome Res. Jul.-Aug. 2005;4(4):1192-1199.
Neziri et al., Cloning and molecular characterization of Dashurin encoded by C20orf116, a PCI-domain containing protein. Biochim Biophys Acta. Apr. 2010;1800(4):430-438.
Norman et al., Progressive Renal Disease: Fibroblasts, Extracellular Matrix, and Integrins. Exp Nephrol. Mar.-Apr. 1999;7(2):167-177.
English Translation of International Search Report and Written Opinion issued in 200980154224.5 dated Nov. 23, 2012.
Zhu et al., Expression of Urinary Epidermal Growth Factor and Renal Function. J Clin Urol Dec. 31, 1998;13(8):374-379.
Zhu et al., Expression of Urinary Epidermal Growth Factor and Renal Function. J Clin Urol Dec. 31, 1998;13(8):374-379 (abstract English translation).
Sun et al., A Survey on the Relationship between the Epidermal Growth Factor and Renal Function. Int J Transpl Hemopurific Dec. 31, 2006;4(1):41-44.
Sun et al., A Survey on the Relationship between the Epidermal Growth Factor and Renal Function. Int J Transpl Hemopurific Dec. 31, 2006;4(1):41-44 (abstract English translation).
Caron et al. Ischemic injury alters endothelial cell properties of kidney cortex:stimulation of MMP-9. Exp Cell Res. Oct. 15, 2005;301(1):105-116.
Non Final Office Action issued by the US Patent and Trademark Office in U.S. Appl. No. 13/577,243 dated Feb. 14, 2013.
FDA, European Medicines Agency to Consider Additional Test Results When Assessing New Drug Safety—Collaborative effort by FDA and EMEA expected to yield additional safety data. http://www.natap.org/2008/newsUpdates/071608_01.htm dated Jun. 12, 2008.
Harpur et al., Biological Qualification of Biomarkers of Chemical-Induced Renal Toxicity in Two Strains of Male Rat. Toxicol Sci. Aug. 2011;122(2):235-252.
Thaker et al., Identification of thrombospondin 1 (TSP-1) as a novel mediator of cell injury in kidney ischemia. J Clin Invest. Dec. 2005;115(12):3451-3458.
Mast et al., Clinical utility of the soluble transferrin receptor and comparison with serum ferritin in several populations. Clin Chem. Jan. 1998;44(1):45-51.
Iglesias et al., Thyroid Dysfunction and Kidney Disease (Revised version). Eur J Endocrinol. Dec. 18, 2008:32 pages retrieved from URL://www.eje.org/content!early/2008/12/18/EJE-08-0837.full.pdf.
Rajashekar et al., Systemic diseases with renal manifestations. Prim Care. Jun. 2008;35(2):297-328.abstract retrieved from URL:www.ncbi.nlm.nih.gov/pubmed/18486717.
Rini et al., Renal cell carcinoma. Lancet. Mar. 28, 2009;373(9669):1119-1132.
Sharma et al. Two-dimensional fluorescence difference gel electrophoresis analysis of the urine proteome in human diabetic nephropathy. Proteomics. Jul. 2005;5(10):2648-2655.
Malm et al., Changes in the plasma levels of vitamin K-dependent proteins C and S and of C4b-binding protein during pregnancy and oral contraception. Br J Haematol. Apr. 1988;68(4):437-443.
Matsuzaka et al., Relationship between vitamin K dependent coagulation factors and anticoagulants (protein C and protein S) in neonatal vitamin K deficiency. Arch Dis Child. Mar. 1993;68(3 Spec No):297-302.
Maddens et al., Chitinase-like Proteins are Candidate Biomarkers for Sepsis-induced Acute Kidney Injury. Mol Cell Proteomics. Jan. 10, 2012;11(6):1-13.
Haase et al., A comparison of the RIFLE and Acute Kidney Injury Network classifications for cardiac surgery-associated acute kidney injury: A prospective cohort study. J Thorac Cardiovasc Surg. Dec. 2009;138(6):1370-1376.
Zaffanello M et al., Early diagnosis of acute kidney injury with urinary biomarkers in the newborn. J Matern Fetal Neonatal Med. 2009;22 Suppl 3:62-66.
Calabrese et al., Oxidative stress and cellular stress response in diabetic nephropathy. Database Biosis [Online]. Biosciences Information Service Jan. 2007; XP002705326. Database accession No. PREV200800097004 (abstract):3 pages & Cell Stress Chaperones. 2007 Winter;12(4):299-306.
Musial et al., The Heat Shock Protein Profile in Children with Chronic Kidney Disease. Perit Dial Int. Mar.-Apr. 2010;30(2):227-232.
Tao et al., Expression of 60-kDa and Inducible 70-kDa Stress Proteins in Gentamicin-Induced Acute Renal Failure. Clin Exp Nephrol. Jul. 1997;1:254-260.
Daemen et al., Apoptosis and Chemokine Induction after Renal Ischemia-Reperfusion.
Lemay et al., Prominent and Sustained Up-Regulation of Gp130-Signaling Cytokines and of the Chemokine Mip-2 in Murine Renal Ischemia-Reperfusion Injury. Transplantation. Mar. 15, 2000;69(5):959-63.
Miura et al., Neutralization of Gro(alpha) and Macrophage Inflammatory Protein-2 Attenuates Renal Ischemia/Reperfusion Injury. Am J Pathol. Dec. 2001;159(6):2137-2145.
Molls et al., Keratinocyte-derived chemokine is an early biomarker of ischemic acute kidney injury. Am J Physiol Renal Physiol. May 2006;290(5):F1187-1193.
Sato et al., Midkine Is Involved in Neutrophil Infiltration into the Tubulointerstitium in Ischemic Renal Injury. J Immunol. Sep. 15, 2001;167(6):3463-3469.
Shimoda et al., Cathepsin G Is Required for Sustained Inflammation and Tissue Injury after Reperfusion of Ischemic Kidneys. Am J Pathol. Mar. 2007;170(3):930-940.
Thurman et al., C3a Is Required for the Production of CXC Chemokines by Tubular Epithelial Cells after Renal Ishemia/Reperfusion. J Immunol. Feb. 1, 2007;178(3):1819-1828.
Office Action issued by SIPO in Chinese patent application No. 201510191800.0 dated Mar. 30, 2016.
Office Action issued by SIPO in Chinese patent application No. 201510191800.0 dated Dec. 28, 2016.
Shi et al., Immune transmission turbidimetry. β2-microglobulin kit. Chinese medicine at the grass-roots level, Chin J Prim Med Pharm. Nov. 2006;13(11):1803-1804—incl Engl lang transl abstract only.
Sun et al., β-MG of time-resolved fluorescence immunoassay kits: Development and Quality Evaluation of β2 MG TRFIA Kit. The tag immune analysis and clinical, Labeled Immunoassays & Clin Med. Sep. 2007;14(3): 164-175—incl Engl lang transl abstract only.
Office Action issued by the JPO in Japanese patent application No. 2015-196689 dated Aug. 16, 2016.
Reichert et al., Urinary Excretion of beta2-Microglobulin Predicts Renal Outcome in Patients with Idiopathic Membranous Nephropathy. J Am Soc Nephrol. Dec. 1995;6(6):1666-1669.
Office Action issued by the JPO in Japanese patent application No. 2012-538053 dated Jun. 24, 2014.
Office Action issued by the JPO in Japanese patent application No. 2012-538053 dated Jun. 2, 2015.
Office Action issued by SIPO in Chinese patent application No. 201080060626.1 dated Jan. 17, 2014.
Office Action issued by SIPO in Chinese patent application No. 201080060626.1 dated Sep. 16, 2014.
Vlaskou et al., Human neutral brush border endopeptidase EC 3.4.24.11 in urine,its isolation,characterisation and activity in renal diseases. Clin Chim Acta. Jul. 2000;297(1-2):103-121.
Jo et al., "Pharmacologic Treatment of Acute Kidney Injury: Why Drugs Haven't Worked and What Is on the Horizon", Clin J Am Soc Nephrol 2: 356-365, 2007. doi: 10.2215/CJN.03280906.

* cited by examiner

METHODS AND COMPOSITIONS FOR DIAGNOSIS AND PROGNOSIS OF RENAL INJURY AND RENAL FAILURE

CROSS REFERENCE TO RELATED APPLICATIONS

The present invention is filed under 35 U.S.C. § 371 as the U.S. national phase of International Application No. PCT/US2010/055730, filed Nov. 5, 2010, which designated the U.S. and claims the benefit of priority to U.S. Provisional Patent Application No. 61/259,163 filed Nov. 7, 2009; U.S. Provisional Patent Application No. 61/259,540 filed Nov. 9, 2009; U.S. Provisional Patent Application No. 61/259,140 filed Nov. 7, 2009; U.S. Provisional Patent Application No. 61/259,142 filed Nov. 7, 2009; U.S. Provisional Patent Application No. 61/259,143 filed Nov. 7, 2009; U.S. Provisional Patent Application No. 61/259,141 filed Nov. 7, 2009; and U.S. Provisional Patent Application No. 61/259,511 filed Nov. 9, 2009, each of which is hereby incorporated in its entirety including all tables, figures, and claims.

SEQUENCE LISTING

The instant application contains a Sequence Listing which has been submitted in ASCII format via EFS-Web and is hereby incorporated by reference in its entirety. Said ASCII copy, created on May 5, 2012, is named AST1250US_SequenceListing_txt and is 26,063 bytes in size.

BACKGROUND OF THE INVENTION

The following discussion of the background of the invention is merely provided to aid the reader in understanding the invention and is not admitted to describe or constitute prior art to the present invention.

The kidney is responsible for water and solute excretion from the body. Its functions include maintenance of acid-base balance, regulation of electrolyte concentrations, control of blood volume, and regulation of blood pressure. As such, loss of kidney function through injury and/or disease results in substantial morbidity and mortality. A detailed discussion of renal injuries is provided in Harrison's Principles of Internal Medicine, 17$^{th}$ Ed., McGraw Hill, New York, pages 1741-1830, which are hereby incorporated by reference in their entirety. Renal disease and/or injury may be acute or chronic. Acute and chronic kidney disease are described as follows (from Current Medical Diagnosis & Treatment 2008, 47$^{th}$ Ed, McGraw Hill, New York, pages 785-815, which are hereby incorporated by reference in their entirety): "Acute renal failure is worsening of renal function over hours to days, resulting in the retention of nitrogenous wastes (such as urea nitrogen) and creatinine in the blood. Retention of these substances is called azotemia. Chronic renal failure (chronic kidney disease) results from an abnormal loss of renal function over months to years".

Acute renal failure (ARF, also known as acute kidney injury, or AKI) is an abrupt (typically detected within about 48 hours to 1 week) reduction in glomerular filtration. This loss of filtration capacity results in retention of nitrogenous (urea and creatinine) and non-nitrogenous waste products that are normally excreted by the kidney, a reduction in urine output, or both. It is reported that ARF complicates about 5% of hospital admissions, 4-15% of cardiopulmonary bypass surgeries, and up to 30% of intensive care admissions. ARF may be categorized as prerenal, intrinsic renal, or postrenal in causation. Intrinsic renal disease can be further divided into glomerular, tubular, interstitial, and vascular abnormalities. Major causes of ARF are described in the following table, which is adapted from the Merck Manual, 17$^{th}$ ed., Chapter 222, and which is hereby incorporated by reference in their entirety:

| Type | Risk Factors |
|---|---|
| Prerenal | |
| ECF volume depletion | Excessive diuresis, hemorrhage, GI losses, loss of intravascular fluid into the extravascular space (due to ascites, peritonitis, pancreatitis, or burns), loss of skin and mucus membranes, renal salt- and water-wasting states |
| Low cardiac output | Cardiomyopathy, MI, cardiac tamponade, pulmonary embolism, pulmonary hypertension, positive-pressure mechanical ventilation |
| Low systemic vascular resistance | Septic shock, liver failure, antihypertensive drugs |
| Increased renal vascular resistance | NSAIDs, cyclosporines, tacrolimus, hypercalcemia, anaphylaxis, anesthetics, renal artery obstruction, renal vein thrombosis, sepsis, hepatorenal syndrome |
| Decreased efferent arteriolar tone (leading to decreased GFR from reduced glomerular transcapillary pressure, especially in patients with bilateral renal artery stenosis) | ACE inhibitors or angiotensin II receptor blockers |
| Intrinsic Renal | |
| Acute tubular injury | Ischemia (prolonged or severe prerenal state): surgery, hemorrhage, arterial or venous obstruction; Toxins: NSAIDs, cyclosporines, tacrolimus, aminoglycosides, foscarnet, ethylene glycol, hemoglobin, myoglobin, ifosfamide, heavy metals, methotrexate, radiopaque contrast agents, streptozotocin |

-continued

| Type | Risk Factors |
|---|---|
| Acute glomerulonephritis | ANCA-associated: Crescentic glomerulonephritis, polyarteritis nodosa, Wegener's granulomatosis; Anti-GBM glomerulonephritis: Goodpasture's syndrome; Immune-complex: Lupus glomerulonephritis, postinfectious glomerulonephritis, cryoglobulinemic glomerulonephritis |
| Acute tubulointerstitial nephritis | Drug reaction (eg, β-lactams, NSAIDs, sulfonamides, ciprofloxacin, thiazide diuretics, furosemide, phenytoin, allopurinol, pyelonephritis, papillary necrosis |
| Acute vascular nephropathy | Vasculitis, malignant hypertension, thrombotic microangiopathies, scleroderma, atheroembolism |
| Infiltrative diseases | Lymphoma, sarcoidosis, leukemia |
| Postrenal | |
| Tubular precipitation | Uric acid (tumor lysis), sulfonamides, triamterene, acyclovir, indinavir, methotrexate, ethylene glycol ingestion, myeloma protein, myoglobin |
| Ureteral obstruction | Intrinsic: Calculi, clots, sloughed renal tissue, fungus ball, edema, malignancy, congenital defects; Extrinsic: Malignancy, retroperitoneal fibrosis, ureteral trauma during surgery or high impact injury |
| Bladder obstruction | Mechanical: Benign prostatic hyperplasia, prostate cancer, bladder cancer, urethral strictures, phimosis, paraphimosis, urethral valves, obstructed indwelling urinary catheter; Neurogenic: Anticholinergic drugs, upper or lower motor neuron lesion |

In the case of ischemic ARF, the course of the disease may be divided into four phases. During an initiation phase, which lasts hours to days, reduced perfusion of the kidney is evolving into injury. Glomerular ultrafiltration reduces, the flow of filtrate is reduced due to debris within the tubules, and back leakage of filtrate through injured epithelium occurs. Renal injury can be mediated during this phase by reperfusion of the kidney. Initiation is followed by an extension phase which is characterized by continued ischemic injury and inflammation and may involve endothelial damage and vascular congestion. During the maintenance phase, lasting from 1 to 2 weeks, renal cell injury occurs, and glomerular filtration and urine output reaches a minimum. A recovery phase can follow in which the renal epithelium is repaired and GFR gradually recovers. Despite this, the survival rate of subjects with ARF may be as low as about 60%.

Acute kidney injury caused by radiocontrast agents (also called contrast media) and other nephrotoxins such as cyclosporine, antibiotics including aminoglycosides and anticancer drugs such as cisplatin manifests over a period of days to about a week. Contrast induced nephropathy (CIN, which is AKI caused by radiocontrast agents) is thought to be caused by intrarenal vasoconstriction (leading to ischemic injury) and from the generation of reactive oxygen species that are directly toxic to renal tubular epithelial cells. CIN classically presents as an acute (onset within 24-48 h) but reversible (peak 3-5 days, resolution within 1 week) rise in blood urea nitrogen and serum creatinine.

A commonly reported criteria for defining and detecting AKI is an abrupt (typically within about 2-7 days or within a period of hospitalization) elevation of serum creatinine. Although the use of serum creatinine elevation to define and detect AKI is well established, the magnitude of the serum creatinine elevation and the time over which it is measured to define AKI varies considerably among publications. Traditionally, relatively large increases in serum creatinine such as 100%, 200%, an increase of at least 100% to a value over 2 mg/dL and other definitions were used to define AKI. However, the recent trend has been towards using smaller serum creatinine rises to define AKI. The relationship between serum creatinine rise, AKI and the associated health risks are reviewed in Praught and Shlipak, *Curr Opin Nephrol Hypertens* 14:265-270, 2005 and Chertow et al, *J Am Soc Nephrol* 16: 3365-3370, 2005, which, with the references listed therein, are hereby incorporated by reference in their entirety. As described in these publications, acute worsening renal function (AKI) and increased risk of death and other detrimental outcomes are now known to be associated with very small increases in serum creatinine. These increases may be determined as a relative (percent) value or a nominal value. Relative increases in serum creatinine as small as 20% from the pre-injury value have been reported to indicate acutely worsening renal function (AKI) and increased health risk, but the more commonly reported value to define AKI and increased health risk is a relative increase of at least 25%. Nominal increases as small as 0.3 mg/dL, 0.2 mg/dL or even 0.1 mg/dL have been reported to indicate worsening renal function and increased risk of death. Various time periods for the serum creatinine to rise to these threshold values have been used to define AKI, for example, ranging from 2 days, 3 days, 7 days, or a variable period defined as the time the patient is in the hospital or intensive care unit. These studies indicate there is not a particular threshold serum creatinine rise (or time period for the rise) for worsening renal function or AKI, but rather a continuous increase in risk with increasing magnitude of serum creatinine rise.

One study (Lassnigg et all, *J Am Soc Nephrol* 15:1597-1605, 2004, hereby incorporated by reference in its entirety) investigated both increases and decreases in serum creatinine. Patients with a mild fall in serum creatinine of −0.1 to −0.3 mg/dL following heart surgery had the lowest mortality rate. Patients with a larger fall in serum creatinine (more than or equal to −0.4 mg/dL) or any increase in serum creatinine had a larger mortality rate. These findings caused the authors to conclude that even very subtle changes in renal function (as detected by small creatinine changes within 48 hours of surgery) seriously effect patient's outcomes. In an effort to reach consensus on a unified classification system for using serum creatinine to define AKI in clinical trials and in clinical practice, Bellomo et al., *Crit. Care.* 8(4):R204-12, 2004, which is hereby incorporated by reference in its entirety, proposes the following classifications for stratifying AKI patients:

"Risk": serum creatinine increased 1.5 fold from baseline OR urine production of <0.5 ml/kg body weight/hr for 6 hours;

"Injury": serum creatinine increased 2.0 fold from baseline OR urine production <0.5 ml/kg/hr for 12 h;

"Failure": serum creatinine increased 3.0 fold from baseline OR creatinine >355 μmol/l (with a rise of >44) or urine output below 0.3 ml/kg/hr for 24 h or anuria for at least 12 hours;

And included two clinical outcomes:

"Loss": persistent need for renal replacement therapy for more than four weeks.

"ESRD": end stage renal disease—the need for dialysis for more than 3 months.

These criteria are called the RIFLE criteria, which provide a useful clinical tool to classify renal status. As discussed in Kellum, *Crit. Care Med.* 36: S141-45, 2008 and Ricci et al., *Kidney Int.* 73, 538-546, 2008, each hereby incorporated by reference in its entirety, the RIFLE criteria provide a uniform definition of AKI which has been validated in numerous studies.

More recently, Mehta et al., *Crit. Care* 11:R31 (doi: 10.1186.cc5713), 2007, hereby incorporated by reference in its entirety, proposes the following similar classifications for stratifying AKI patients, which have been modified from RIFLE:

"Stage I": increase in serum creatinine of more than or equal to 0.3 mg/dL (≥26.4 μmol/L) or increase to more than or equal to 150% (1.5-fold) from baseline OR urine output less than 0.5 mL/kg per hour for more than 6 hours;

"Stage II": increase in serum creatinine to more than 200% (>2-fold) from baseline OR urine output less than 0.5 mL/kg per hour for more than 12 hours;

"Stage III": increase in serum creatinine to more than 300% (>3-fold) from baseline OR serum creatinine ≥354 μmol/L accompanied by an acute increase of at least 44 μmol/L OR urine output less than 0.3 mL/kg per hour for 24 hours or anuria for 12 hours.

The CIN Consensus Working Panel (McCollough et al, Rev Cardiovasc Med. 2006; 7(4): 177-197, hereby incorporated by reference in its entirety) uses a serum creatinine rise of 25% to define Contrast induced nephropathy (which is a type of AKI). Although various groups propose slightly different criteria for using serum creatinine to detect AKI, the consensus is that small changes in serum creatinine, such as 0.3 mg/dL or 25%, are sufficient to detect AKI (worsening renal function) and that the magnitude of the serum creatinine change is an indicator of the severity of the AKI and mortality risk.

Although serial measurement of serum creatinine over a period of days is an accepted method of detecting and diagnosing AKI and is considered one of the most important tools to evaluate AKI patients, serum creatinine is generally regarded to have several limitations in the diagnosis, assessment and monitoring of AKI patients. The time period for serum creatinine to rise to values (e.g., a 0.3 mg/dL or 25% rise) considered diagnostic for AKI can be 48 hours or longer depending on the definition used. Since cellular injury in AKI can occur over a period of hours, serum creatinine elevations detected at 48 hours or longer can be a late indicator of injury, and relying on serum creatinine can thus delay diagnosis of AKI. Furthermore, serum creatinine is not a good indicator of the exact kidney status and treatment needs during the most acute phases of AKI when kidney function is changing rapidly. Some patients with AKI will recover fully, some will need dialysis (either short term or long term) and some will have other detrimental outcomes including death, major adverse cardiac events and chronic kidney disease. Because serum creatinine is a marker of filtration rate, it does not differentiate between the causes of AKI (pre-renal, intrinsic renal, post-renal obstruction, atheroembolic, etc) or the category or location of injury in intrinsic renal disease (for example, tubular, glomerular or interstitial in origin). Urine output is similarly limited, Knowing these things can be of vital importance in managing and treating patients with AKI.

These limitations underscore the need for better methods to detect and assess AKI, particularly in the early and subclinical stages, but also in later stages when recovery and repair of the kidney can occur. Furthermore, there is a need to better identify patients who are at risk of having an AKI.

BRIEF SUMMARY OF THE INVENTION

It is an object of the invention to provide methods and compositions for evaluating renal function in a subject. As described herein, measurement of one or more biomarkers selected from the group consisting of Cathepsin B, Renin, Dipeptidyl Peptidase IV, Neprilysin, Beta-2-microglobulin, Carbonic anhydrase IX, and C-X-C motif chemokine 2 (each referred to herein as a "kidney injury marker") can be used for diagnosis, prognosis, risk stratification, staging, monitoring, categorizing and determination of further diagnosis and treatment regimens in subjects suffering or at risk of suffering from an injury to renal function, reduced renal function, and/or acute renal failure (also called acute kidney injury).

The kidney injury markers of the present invention may be used, individually or in panels comprising a plurality of kidney injury markers, for risk stratification (that is, to identify subjects at risk for a future injury to renal function, for future progression to reduced renal function, for future progression to ARF, for future improvement in renal function, etc.); for diagnosis of existing disease (that is, to identify subjects who have suffered an injury to renal function, who have progressed to reduced renal function, who have progressed to ARF, etc.); for monitoring for deterioration or improvement of renal function; and for predicting a future medical outcome, such as improved or worsening renal function, a decreased or increased mortality risk, a decreased or increased risk that a subject will require renal replacement therapy (i.e., hemodialysis, peritoneal dialysis, hemofiltration, and/or renal transplantation, a decreased or increased risk that a subject will recover from an injury to renal function, a decreased or increased risk that a subject will recover from ARF, a decreased or increased risk that a subject will progress to end stage renal disease, a decreased or increased risk that a subject will progress to chronic renal failure, a decreased or increased risk that a subject will suffer rejection of a transplanted kidney, etc.

In a first aspect, the present invention relates to methods for evaluating renal status in a subject. These methods comprise performing an assay method that is configured to detect one or more biomarkers selected from the group consisting of Cathepsin B, Renin, Dipeptidyl Peptidase IV, Neprilysin, Beta-2-microglobulin, Carbonic anhydrase IX, and C-X-C motif chemokine 2 is/are then correlated to the renal status of the subject. This correlation to renal status may include correlating the assay result(s) to one or more of risk stratification, diagnosis, prognosis, staging, classifying and monitoring of the subject as described herein. Thus, the present invention utilizes one or more kidney injury markers of the present invention for the evaluation of renal injury.

In certain embodiments, the methods for evaluating renal status described herein are methods for risk stratification of the subject; that is, assigning a likelihood of one or more future changes in renal status to the subject. In these embodiments, the assay result(s) is/are correlated to one or more such future changes. The following are preferred risk stratification embodiments.

In preferred risk stratification embodiments, these methods comprise determining a subject's risk for a future injury to renal function, and the assay result(s) is/are correlated to a likelihood of such a future injury to renal function. For example, the measured concentration(s) may each be compared to a threshold value. For a "positive going" kidney injury marker, an increased likelihood of suffering a future injury to renal function is assigned to the subject when the measured concentration is above the threshold, relative to a likelihood assigned when the measured concentration is below the threshold. For a "negative going" kidney injury marker, an increased likelihood of suffering a future injury to renal function is assigned to the subject when the measured concentration is below the threshold, relative to a likelihood assigned when the measured concentration is above the threshold.

In other preferred risk stratification embodiments, these methods comprise determining a subject's risk for future reduced renal function, and the assay result(s) is/are correlated to a likelihood of such reduced renal function. For example, the measured concentrations may each be compared to a threshold value. For a "positive going" kidney injury marker, an increased likelihood of suffering a future reduced renal function is assigned to the subject when the measured concentration is above the threshold, relative to a likelihood assigned when the measured concentration is below the threshold. For a "negative going" kidney injury marker, an increased likelihood of future reduced renal function is assigned to the subject when the measured concentration is below the threshold, relative to a likelihood assigned when the measured concentration is above the threshold.

In still other preferred risk stratification embodiments, these methods comprise determining a subject's likelihood for a future improvement in renal function, and the assay result(s) is/are correlated to a likelihood of such a future improvement in renal function. For example, the measured concentration(s) may each be compared to a threshold value. For a "positive going" kidney injury marker, an increased likelihood of a future improvement in renal function is assigned to the subject when the measured concentration is below the threshold, relative to a likelihood assigned when the measured concentration is above the threshold. For a "negative going" kidney injury marker, an increased likelihood of a future improvement in renal function is assigned to the subject when the measured concentration is above the threshold, relative to a likelihood assigned when the measured concentration is below the threshold.

In yet other preferred risk stratification embodiments, these methods comprise determining a subject's risk for progression to ARF, and the result(s) is/are correlated to a likelihood of such progression to ARF. For example, the measured concentration(s) may each be compared to a threshold value. For a "positive going" kidney injury marker, an increased likelihood of progression to ARF is assigned to the subject when the measured concentration is above the threshold, relative to a likelihood assigned when the measured concentration is below the threshold. For a "negative going" kidney injury marker, an increased likelihood of progression to ARF is assigned to the subject when the measured concentration is below the threshold, relative to a likelihood assigned when the measured concentration is above the threshold.

And in other preferred risk stratification embodiments, these methods comprise determining a subject's outcome risk, and the assay result(s) is/are correlated to a likelihood of the occurrence of a clinical outcome related to a renal injury suffered by the subject. For example, the measured concentration(s) may each be compared to a threshold value. For a "positive going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is above the threshold, relative to a likelihood assigned when the measured concentration is below the threshold. For a "negative going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is below the threshold, relative to a likelihood assigned when the measured concentration is above the threshold.

In such risk stratification embodiments, preferably the likelihood or risk assigned is that an event of interest is more or less likely to occur within 180 days of the time at which the body fluid sample is obtained from the subject. In particularly preferred embodiments, the likelihood or risk assigned relates to an event of interest occurring within a shorter time period such as 18 months, 120 days, 90 days, 60 days, 45 days, 30 days, 21 days, 14 days, 7 days, 5 days, 96 hours, 72 hours, 48 hours, 36 hours, 24 hours, 12 hours, or less. A risk at 0 hours of the time at which the body fluid sample is obtained from the subject is equivalent to diagnosis of a current condition.

In preferred risk stratification embodiments, the subject is selected for risk stratification based on the pre-existence in the subject of one or more known risk factors for prerenal, intrinsic renal, or postrenal ARF. For example, a subject undergoing or having undergone major vascular surgery, coronary artery bypass, or other cardiac surgery; a subject having pre-existing congestive heart failure, preeclampsia, eclampsia, diabetes mellitus, hypertension, coronary artery disease, proteinuria, renal insufficiency, glomerular filtration below the normal range, cirrhosis, serum creatinine above the normal range, or sepsis; or a subject exposed to NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin are all preferred subjects for monitoring risks according to the methods described herein. This list is not meant to be limiting. By "pre-existence" in this context is meant that the risk factor exists at the time the body fluid sample is obtained from the subject. In particularly preferred embodiments, a subject is chosen for risk stratification based on an existing diagnosis of injury to renal function, reduced renal function, or ARF.

In other embodiments, the methods for evaluating renal status described herein are methods for diagnosing a renal injury in the subject; that is, assessing whether or not a subject has suffered from an injury to renal function, reduced renal function, or ARF. In these embodiments, the assay result(s), for example measured concentration(s) of one or more biomarkers selected from the group consisting of Cathepsin B, Renin, Dipeptidyl Peptidase IV, Neprilysin, Beta-2-microglobulin, Carbonic anhydrase IX, and C-X-C motif chemokine 2 is/are correlated to the occurrence or nonoccurrence of a change in renal status. The following are preferred diagnostic embodiments.

In preferred diagnostic embodiments, these methods comprise diagnosing the occurrence or nonoccurrence of an injury to renal function, and the assay result(s) is/are correlated to the occurrence or nonoccurrence of such an injury. For example, each of the measured concentration(s) may be compared to a threshold value. For a positive going marker, an increased likelihood of the occurrence of an injury to renal function is assigned to the subject when the measured concentration is above the threshold (relative to the likelihood assigned when the measured concentration is below the threshold); alternatively, when the measured concentration is below the threshold, an increased likelihood of the nonoccurrence of an injury to renal function may be assigned to the subject (relative to the likelihood assigned when the measured concentration is above the threshold). For a negative going marker, an increased likelihood of the occurrence of an injury to renal function is assigned to the subject when the measured concentration is below the threshold (relative to the likelihood assigned when the measured concentration is above the threshold); alternatively, when the measured concentration is above the threshold, an increased likelihood of the nonoccurrence of an injury to renal function may be assigned to the subject (relative to the likelihood assigned when the measured concentration is below the threshold).

In other preferred diagnostic embodiments, these methods comprise diagnosing the occurrence or nonoccurrence of reduced renal function, and the assay result(s) is/are correlated to the occurrence or nonoccurrence of an injury causing reduced renal function. For example, each of the measured concentration(s) may be compared to a threshold value. For a positive going marker, an increased likelihood of the occurrence of an injury causing reduced renal function is assigned to the subject when the measured concentration is above the threshold (relative to the likelihood assigned when the measured concentration is below the threshold); alternatively, when the measured concentration is below the threshold, an increased likelihood of the nonoccurrence of an injury causing reduced renal function may be assigned to the subject (relative to the likelihood assigned when the measured concentration is above the threshold). For a negative going marker, an increased likelihood of the occurrence of an injury causing reduced renal function is assigned to the subject when the measured concentration is below the threshold (relative to the likelihood assigned when the measured concentration is above the threshold); alternatively, when the measured concentration is above the threshold, an increased likelihood of the nonoccurrence of an injury causing reduced renal function may be assigned to the subject (relative to the likelihood assigned when the measured concentration is below the threshold).

In yet other preferred diagnostic embodiments, these methods comprise diagnosing the occurrence or nonoccurrence of ARF, and the assay result(s) is/are correlated to the occurrence or nonoccurrence of an injury causing ARF. For example, each of the measured concentration(s) may be compared to a threshold value. For a positive going marker, an increased likelihood of the occurrence of ARF is assigned to the subject when the measured concentration is above the threshold (relative to the likelihood assigned when the measured concentration is below the threshold); alternatively, when the measured concentration is below the threshold, an increased likelihood of the nonoccurrence of ARF may be assigned to the subject (relative to the likelihood assigned when the measured concentration is above the threshold). For a negative going marker, an increased likelihood of the occurrence of ARF is assigned to the subject when the measured concentration is below the threshold (relative to the likelihood assigned when the measured concentration is above the threshold); alternatively, when the measured concentration is above the threshold, an increased likelihood of the nonoccurrence of ARF may be assigned to the subject (relative to the likelihood assigned when the measured concentration is below the threshold).

In still other preferred diagnostic embodiments, these methods comprise diagnosing a subject as being in need of renal replacement therapy, and the assay result(s) is/are correlated to a need for renal replacement therapy. For example, each of the measured concentration(s) may be compared to a threshold value. For a positive going marker, an increased likelihood of the occurrence of an injury creating a need for renal replacement therapy is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal replacement therapy may be assigned to the subject (relative to the likelihood assigned when the measured concentration is above the threshold). For a negative going marker, an increased likelihood of the occurrence of an injury creating a need for renal replacement therapy is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal replacement therapy may be assigned to the subject (relative to the likelihood assigned when the measured concentration is below the threshold).

In still other preferred diagnostic embodiments, these methods comprise diagnosing a subject as being in need of renal transplantation, and the assay result(s0 is/are correlated to a need for renal transplantation. For example, each of the measured concentration(s) may be compared to a threshold value. For a positive going marker, an increased likelihood of the occurrence of an injury creating a need for renal transplantation is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal transplantation may be assigned to the subject (relative to the likelihood assigned when the measured concentration is above the threshold). For a negative going marker, an increased likelihood of the occurrence of an injury creating a need for renal transplantation is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal transplantation may be assigned to the subject (relative to the likelihood assigned when the measured concentration is below the threshold).

In still other embodiments, the methods for evaluating renal status described herein are methods for monitoring a renal injury in the subject; that is, assessing whether or not renal function is improving or worsening in a subject who has suffered from an injury to renal function, reduced renal function, or ARF. In these embodiments, the assay result(s), for example measured concentration(s) of one or more biomarkers selected from the group consisting of Cathepsin B, Renin, Dipeptidyl Peptidase IV, Neprilysin, Beta-2-microglobulin, Carbonic anhydrase IX, and C-X-C motif chemokine 2 is/are correlated to the occurrence or nonoccurrence of a change in renal status. The following are preferred monitoring embodiments.

In preferred monitoring embodiments, these methods comprise monitoring renal status in a subject suffering from an injury to renal function, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other preferred monitoring embodiments, these methods comprise monitoring renal status in a subject suffering from reduced renal function, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In yet other preferred monitoring embodiments, these methods comprise monitoring renal status in a subject suffering from acute renal failure, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other additional preferred monitoring embodiments, these methods comprise monitoring renal status in a subject at risk of an injury to renal function due to the pre-existence of one or more known risk factors for prerenal, intrinsic renal, or postrenal ARF, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In still other embodiments, the methods for evaluating renal status described herein are methods for classifying a renal injury in the subject; that is, determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage. In these embodiments, the assay result(s), for example measured concentration(s) of one or more biomarkers selected from the group consisting of Cathepsin B, Renin, Dipeptidyl Peptidase IV, Neprilysin, Beta-2-microglobulin, Carbonic anhydrase IX, and C-X-C motif chemokine 2 is/are correlated to a particular class and/or subclass. The following are preferred classification embodiments.

In preferred classification embodiments, these methods comprise determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage, and the assay result(s) is/are correlated to the injury classification for the subject. For example, the measured concentration may be compared to a threshold value, and when the measured concentration is above the threshold, a particular classification is assigned; alternatively, when the measured concentration is below the threshold, a different classification may be assigned to the subject.

A variety of methods may be used by the skilled artisan to arrive at a desired threshold value for use in these methods. For example, the threshold value may be determined from a population of normal subjects by selecting a concentration representing the $75^{th}$, $85^{th}$, $90^{th}$, $95^{th}$, or $99^{th}$ percentile of a kidney injury marker measured in such normal subjects. Alternatively, the threshold value may be determined from a "diseased" population of subjects, e.g., those suffering from an injury or having a predisposition for an injury (e.g., progression to ARF or some other clinical outcome such as death, dialysis, renal transplantation, etc.), by selecting a concentration representing the $75^{th}$, $85^{th}$, $90^{th}$, $95^{th}$, or $99^{th}$ percentile of a kidney injury marker measured in such subjects. In another alternative, the threshold value may be determined from a prior measurement of a kidney injury marker in the same subject; that is, a temporal change in the level of a kidney injury marker in the subject may be used to assign risk to the subject.

The foregoing discussion is not meant to imply, however, that the kidney injury markers of the present invention must be compared to corresponding individual thresholds. Methods for combining assay results can comprise the use of multivariate logistical regression, loglinear modeling, neural network analysis, n-of-m analysis, decision tree analysis, calculating ratios of markers, etc. This list is not meant to be limiting. In these methods, a composite result which is determined by combining individual markers may be treated as if it is itself a marker; that is, a threshold may be determined for the composite result as described herein for individual markers, and the composite result for an individual patient compared to this threshold.

The ability of a particular test to distinguish two populations can be established using ROC analysis. For example, ROC curves established from a "first" subpopulation which is predisposed to one or more future changes in renal status, and a "second" subpopulation which is not so predisposed can be used to calculate a ROC curve, and the area under the curve provides a measure of the quality of the test. Preferably, the tests described herein provide a ROC curve area greater than 0.5, preferably at least 0.6, more preferably 0.7, still more preferably at least 0.8, even more preferably at least 0.9, and most preferably at least 0.95.

In certain aspects, the measured concentration of one or more kidney injury markers, or a composite of such markers, may be treated as continuous variables. For example, any particular concentration can be converted into a corresponding probability of a future reduction in renal function for the subject, the occurrence of an injury, a classification, etc. In yet another alternative, a threshold that can provide an acceptable level of specificity and sensitivity in separating a population of subjects into "bins" such as a "first" subpopulation (e.g., which is predisposed to one or more future changes in renal status, the occurrence of an injury, a classification, etc.) and a "second" subpopulation which is not so predisposed. A threshold value is selected to separate this first and second population by one or more of the following measures of test accuracy:

an odds ratio greater than 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less;

a specificity of greater than 0.5, preferably at least about 0.6, more preferably at least about 0.7, still more preferably at least about 0.8, even more preferably at least about 0.9 and most preferably at least about 0.95, with a corresponding sensitivity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

a sensitivity of greater than 0.5, preferably at least about 0.6, more preferably at least about 0.7, still more preferably at least about 0.8, even more preferably at least about 0.9 and most preferably at least about 0.95, with a corresponding specificity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

at least about 75% sensitivity, combined with at least about 75% specificity;

a positive likelihood ratio (calculated as sensitivity/(1-specificity)) of greater than 1, at least about 2, more preferably at least about 3, still more preferably at least about 5, and most preferably at least about 10; or a negative likelihood ratio (calculated as (1-sensitivity)/specificity) of less than 1, less than or equal to about 0.5, more preferably less than or equal to about 0.3, and most preferably less than or equal to about 0.1.

The term "about" in the context of any of the above measurements refers to +/−5% of a given measurement.

Multiple thresholds may also be used to assess renal status in a subject. For example, a "first" subpopulation which is predisposed to one or more future changes in renal status, the occurrence of an injury, a classification, etc., and a "second" subpopulation which is not so predisposed can be combined into a single group. This group is then subdivided into three or more equal parts (known as tertiles, quartiles, quintiles, etc., depending on the number of subdivisions). An odds ratio is assigned to subjects based on which subdivision they fall into. If one considers a tertile, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to suffer one or more future changes in renal status in comparison to someone in the first tertile. The third tertile is also assigned an odds ratio that is relative to that first tertile.

In certain embodiments, the assay method is an immunoassay. Antibodies for use in such assays will specifically bind a full length kidney injury marker of interest, and may also bind one or more polypeptides that are "related" thereto, as that term is defined hereinafter. Numerous immunoassay formats are known to those of skill in the art. Preferred body fluid samples are selected from the group consisting of urine, blood, serum, saliva, tears, and plasma.

The foregoing method steps should not be interpreted to mean that the kidney injury marker assay result(s) is/are used in isolation in the methods described herein. Rather, additional variables or other clinical indicia may be included in the methods described herein. For example, a risk stratification, diagnostic, classification, monitoring, etc. method may combine the assay result(s) with one or more variables measured for the subject selected from the group consisting of demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a glomerular filtration rate, an estimated glomerular filtration rate, a urine production rate, a serum or plasma creatinine concentration, a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, a renal failure index calculated as urine sodium/(urine creatinine/plasma creatinine), a serum or plasma neutrophil gelatinase (NGAL) concentration, a urine NGAL concentration, a serum or plasma cystatin C concentration, a serum or plasma cardiac troponin concentration, a serum or plasma BNP concentration, a serum or plasma NTproBNP concentration, and a serum or plasma proBNP concentration. Other measures of renal function which may be combined with one or more kidney injury marker assay result(s) are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

When more than one marker is measured, the individual markers may be measured in samples obtained at the same time, or may be determined from samples obtained at different (e.g., an earlier or later) times. The individual markers may also be measured on the same or different body fluid samples. For example, one kidney injury marker may be measured in a serum or plasma sample and another kidney injury marker may be measured in a urine sample. In addition, assignment of a likelihood may combine an individual kidney injury marker assay result with temporal changes in one or more additional variables.

In various related aspects, the present invention also relates to devices and kits for performing the methods described herein. Suitable kits comprise reagents sufficient for performing an assay for at least one of the described kidney injury markers, together with instructions for performing the described threshold comparisons.

In certain embodiments, reagents for performing such assays are provided in an assay device, and such assay devices may be included in such a kit. Preferred reagents can comprise one or more solid phase antibodies, the solid phase antibody comprising antibody that detects the intended biomarker target(s) bound to a solid support. In the case of sandwich immunoassays, such reagents can also include one or more detectably labeled antibodies, the detectably labeled antibody comprising antibody that detects the intended biomarker target(s) bound to a detectable label. Additional optional elements that may be provided as part of an assay device are described hereinafter.

Detectable labels may include molecules that are themselves detectable (e.g., fluorescent moieties, electrochemical labels, ecl (electrochemical luminescence) labels, metal chelates, colloidal metal particles, etc.) as well as molecules that may be indirectly detected by production of a detectable reaction product (e.g., enzymes such as horseradish peroxidase, alkaline phosphatase, etc.) or through the use of a specific binding molecule which itself may be detectable (e.g., a labeled antibody that binds to the second antibody, biotin, digoxigenin, maltose, oligohistidine, 2,4-dintrobenzene, phenylarsenate, ssDNA, dsDNA, etc.).

Generation of a signal from the signal development element can be performed using various optical, acoustical, and electrochemical methods well known in the art. Examples of detection modes include fluorescence, radiochemical detection, reflectance, absorbance, amperometry, conductance, impedance, interferometry, ellipsometry, etc. In certain of these methods, the solid phase antibody is coupled to a transducer (e.g., a diffraction grating, electrochemical sensor, etc) for generation of a signal, while in others, a signal is generated by a transducer that is spatially separate from the solid phase antibody (e.g., a fluorometer that employs an excitation light source and an optical detector). This list is not meant to be limiting. Antibody-based biosensors may also be employed to determine the presence or amount of analytes that optionally eliminate the need for a labeled molecule.

DETAILED DESCRIPTION OF THE INVENTION

The present invention relates to methods and compositions for diagnosis, differential diagnosis, risk stratification, monitoring, classifying and determination of treatment regimens in subjects suffering or at risk of suffering from injury to renal function, reduced renal function and/or acute renal failure through measurement of one or more kidney injury markers. In various embodiments, a measured concentration of one or more biomarkers selected from the group consisting of Cathepsin B, Renin, Dipeptidyl Peptidase IV, Neprilysin, Beta-2-microglobulin, Carbonic anhydrase IX, and C-X-C motif chemokine 2 or one or more markers related thereto, are correlated to the renal status of the subject.

For purposes of this document, the following definitions apply:

As used herein, an "injury to renal function" is an abrupt (within 14 days, preferably within 7 days, more preferably within 72 hours, and still more preferably within 48 hours) measurable reduction in a measure of renal function. Such an injury may be identified, for example, by a decrease in glomerular filtration rate or estimated GFR, a reduction in urine output, an increase in serum creatinine, an increase in serum cystatin C, a requirement for renal replacement therapy, etc. "Improvement in Renal Function" is an abrupt (within 14 days, preferably within 7 days, more preferably within 72 hours, and still more preferably within 48 hours) measurable increase in a measure of renal function. Preferred methods for measuring and/or estimating GFR are described hereinafter.

As used herein, "reduced renal function" is an abrupt (within 14 days, preferably within 7 days, more preferably within 72 hours, and still more preferably within 48 hours) reduction in kidney function identified by an absolute increase in serum creatinine of greater than or equal to 0.1 mg/dL (≥8.8 µmol/L), a percentage increase in serum creatinine of greater than or equal to 20% (1.2-fold from baseline), or a reduction in urine output (documented oliguria of less than 0.5 ml/kg per hour).

As used herein, "acute renal failure" or "ARF" is an abrupt (within 14 days, preferably within 7 days, more preferably within 72 hours, and still more preferably within 48 hours) reduction in kidney function identified by an absolute increase in serum creatinine of greater than or equal to 0.3 mg/dl (≥26.4 µmol/l), a percentage increase in serum creatinine of greater than or equal to 50% (1.5-fold from baseline), or a reduction in urine output (documented oliguria of less than 0.5 ml/kg per hour for at least 6 hours). This term is synonymous with "acute kidney injury" or "AKI."

As used herein, the term "Cathepsin B" refers to one or more polypeptides present in a biological sample that are derived from the Cathepsin B precursor (Swiss-Prot P07858 (SEQ ID NO: 1))

```
          10         20         30         40         50         60
MWQLWASLCC LLVLANARSR PSFHPLSDEL VNYVNKRNTT WQAGHNFYNV DMSYLKRLCG 70         80         90        100        110        120
TFLGGPKPPQ RVMFTEDLKL PASFDAREQW PQCPTIKEIR DQGSCGSCWA FGAVEAISDR
```

```
        130        140        150        160        170        180
ICIHTNAHVS VEVSAEDLLT CCGSMCGDGC NGGYPAEAWN FWTRKGLVSG GLYESHVGCR 190        200        210        220        230        240
PYSIPPCEHH VNGSRPPCTG EGDTPKCSKI CEPGYSPTYK QDKHYGYNSY SVSNSEKDIM 250        260        270        280        290        300
AEIYKNGPVE GAFSVYSDFL LYKSGVYQHV TGEMMGGHAI RILGWGVENG TPYWLVANSW 310        320        330
NTDWGDNGFF KILRGQDHCG IESEVVAGIP RTDQYWEKI
```

The following domains have been identified in Cathepsin B:

| Residues | Length | Domain ID |
|---|---|---|
| 1-17 | 17 | signal peptide |
| 18-79 | 62 | activation peptide |
| 334-339 | 6 | propeptide |
| 80-333 | 254 | Cathepsin B |
| 80-126 | 47 | Cathepsin B light chain |
| 129-333 | 205 | Cathepsin B heavy chain |

As used herein, the term "Renin" refers to one or more polypeptides present in a biological sample that are derived from the Renin precursor (Swiss-Prot P00797 (SEQ ID NO: 2)).

```
        10         20         30         40         50         60
MDGWRRMPRW GLLLLLWGSC TFGLPTDTTT FKRIFLKRMP SIRESLKERG VDMARLGPEW 70         80         90        100        110        120
SQPMKRLTLG NTTSSVILTN YMDTQYYGEI GIGTPPQTFK VVFDTGSSNV WVPSSKCSRL 130        140        150        160        170        180
YTACVYHKLF DASDSSSYKH NGTELTLRYS TGTVSGFLSQ DIITVGGITV TQMFGEVTEM 190        200        210        220        230        240
PALPFMLAEF DGVVGMGFIE QAIGRVTPIF DNIISQGVLK EDVFSFYYNR DSENSQSLGG 250        260        270        280        290        300
QIVLGGSDPQ HYEGNFHYIN LIKTGVWQIQ MKGVSVGSST LLCEDGCLAL VDTGASYISG 310        320        330        340        350        360
STSSIEKLME ALGAKKRLFD YVVKCNEGPT LPDISFHLGG KEYTLTSADY VFQESYSSKK 370        380        390        400
LCTLAIHAMD IPPPTGPTWA LGATFIRKFY TEFDRRNNRI GFALAR
```

The following domains have been identified in Renin:

| Residues | Length | Domain ID |
|---|---|---|
| 1-23 | 23 | Propeptide |
| 24-66 | 43 | Activation peptide |
| 67-406 | 340 | Renin |
| 231-233 | 3 | Missing in isoform 2 |

As used herein, the term "Dipeptidyl peptidase 4" refers to one or more polypeptides present in a biological sample that are derived from the Dipeptidyl peptidase 4 precursor (Swiss-Prot P27487 (SEQ ID NO: 3))

```
        10         20         30         40         50         60
MKTPWKVLLG LLGAAALVTI ITVPVVLLNK GTDDATADSR KTYTLTDYLK NTYRLKLYSL 70         80         90        100        110        120
RWISDHEYLY KQENNILVFN AEYGNSSVFL ENSTFDEFGH SINDYSISPD GQFILLEYNY
```

-continued

```
          130        140        150        160        170        180
   VKQWRHSYTA SYDIYDLNKR QLITEERIPN NTQWVTWSPV GHKLAYVWNN DIYVKIEPNL 190        200        210        220        230        240
   PSYRITWTGK EDIIYNGITD WVYEEEVFSA YSALWWSPNG TFLAYAQFND TEVPLIEYSF 250        260        270        280        290        300
   YSDESLQYPK TVRVPYPKAG AVNPTVKFFV VNTDSLSSVT NATSIQITAP ASMLIGDHYL 310        320        330        340        350        360
   CDVTWATQER ISLQWLRRIQ NYSVMDICDY DESSGRWNCL VARQHIEMST TGWVGRFRPS 370        380        390        400        410        420
   EPHFTLDGNS FYKIISNEEG YRHICYFQID KKDCTFITKG TWEVIGIEAL TSDYLYYISN 430        440        450        460        470        480
   EYKGMPGGRN LYKIQLSDYT KVTCLSCELN PERCQYYSVS FSKEAKYYQL RCSGPGLPLY 490        500        510        520        530        540
   TLHSSVNDKG LRVLEDNSAL DKMLQNVQMP SKKLDFIILN ETKFWYQMIL PPHFDKSKKY 550        560        570        580        590        600
   PLLLDVYAGP CSQKADTVFR LNWATYLAST ENIIVASFDG RGSGYQGDKI MHAINRRLGT 610        620        630        640        650        660
   FEVEDQIEAA RQFSKMGFVD NKRIAIWGWS YGGYVTSMVL GSGSGVFKCG IAVAPVSRWE 670        680        690        700        710        720
   YYDSVYTERY MGLPTPEDNL DHYRNSTVMS RAENFKQVEY LLIHGTADDN VHFQQSAQIS 730        740        750        760
   KALVDVGVDF QAMWYTDEDH GIASSTAHQH IYTHMSHFIK QCFSLP
```

Most preferably, the Dipeptidyl peptidase 4 assay detects one or more soluble forms of Dipeptidyl peptidase 4. Dipeptidyl peptidase 4 is a type II membrane protein having a large extracellular domain, most or all of which is present in soluble forms of Dipeptidyl peptidase 4 generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in Dipeptidyl peptidase 4:

| Residues | Length | Domain ID |
| --- | --- | --- |
| 1-766 | 766 | Dipeptidyl peptidase 4 |
| 39-766 | 728 | Dipeptidyl peptidase 4, soluble form |
| 1-6 | 6 | Cytoplasmic |
| 7-28 | 22 | Anchor signal |
| 29-766 | 738 | Extracellular |

As used herein, the term "Neprilysin" refers to one or more polypeptides present in a biological sample that are derived from the Neprilysin precursor (Swiss-Prot P08473 (SEQ ID NO: 4))

```
           10         20         30         40         50         60
   MGKSESQMDI TDINTPKPKK KQRWTPLEIS LSVLVLLLTI IAVTMIALYA TYDDGICKSS 70         80         90        100        110        120
   DCIKSAARLI QNMDATTEPC TDFFKYACGG WLKRNVIPET SSRYGNFDIL RDELEVVLKD 130        140        150        160        170        180
   VLQEPKTEDI VAVQKAKALY RSCINESAID SRGGEPLLKL LPDIYGWPVA TENWEQKYGA 190        200        210        220        230        240
   SWTAEKAIAQ LNSKYGKKVL INLFVGTDDK NSVNHVIHID QPRLGLPSRD YYECTGIYKE 250        260        270        280        290        300
   ACTAYVDFMI SVARLIRQEE RLPIDENQLA LEMNKVMELE KEIANATAKP EDRNDPMLLY 310        320        330        340        350        360
   NKMTLAQIQN NFSLEINGKP FSWLNFTNEI MSTVNISITN EEDVVVYAPE YLTKLKPILT 370        380        390        400        410        420
   KYSARDLQNL MSWRFIMDLV SSLSRTYKES RNAFRKALYG TTSETATWRR CANYVNGNME
```

```
                           -continued
           430        440        450        460        470        480
    NAVGRLYVEA AFAGESKHVV EDLIAQIREV FIQTLDDLTW MDAETKKRAE EKALAIKERI 490        500        510        520        530        540
    GYPDDIVSND NKLNNEYLEL NYKEDEYFEN IIQNLKFSQS KQLKKLREKV DKDEWISGAA 550        560        570        580        590        600
    VVNAFYSSGR NQIVFPAGIL QPPFFSAQQS NSLNYGGIGM VIGHEITHGF DDNGRNFNKD 610        620        630        640        650        660
    GDLVDWWTQQ SASNFKEQSQ CMVYQYGNFS WDLAGGQHLN GINTLGENIA DNGGLGQAYR 670        680        690        700        710        720
    AYQNYIKKNG EEKLLPGLDL NHKQLFFLNF AQVWCGTYRP EYAVNSIKTD VHSPGNFRII 730        740        750
    GTLQNSAEFS EAFHCRKNSY MNPEKKCRVW
```

Most preferably, the Neprilysin assay detects one or more soluble forms of Neprilysin. Neprilysin is a type II membrane protein having a large extracellular domain, most or all of which is present in soluble forms of Neprilysin generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in Neprilysin:

| Residues | Length | Domain ID |
|---|---|---|
| 1 | 1 | initiator methionine |
| 2-750 | 749 | Neprilysin |
| 2-28 | 27 | Cytoplasmic |
| 29-51 | 23 | Anchor signal |
| 52-750 | 699 | Extracellular |

As used herein, the term "Beta-2-microglobulin" refers to one or more polypeptides present in a biological sample that are derived from the Beta-2-microglobulin precursor (Swiss-Prot P61769 (SEQ ID NO: 5))

```
            10         20         30         40         50         60
    MSRSVALAVL ALLSLSGLEA IQRTPKIQVY SRHPAENGKS NFLNCYVSGF HPSDIEVDLL 70         80         90        100        110
    KNGERIEKVE HSDLSFSKDW SFYLLYYTEF TPTEKDEYAC RVNHVTLSQP KIVKWDRDM
```

The following domains have been identified in Beta-2-microglobulin:

| Residues | Length | Domain ID |
|---|---|---|
| 1-20 | 20 | signal peptide |
| 21-119 | 99 | Beta-2-microglobulin |
| 22-119 | 21 | Beta-2-microglobulin form pI 5.3 |

As used herein, the term "Carbonic anhydrase IX" refers to one or more polypeptides present in a biological sample that are derived from the Carbonic anhydrase IX precursor (Swiss-Prot Q16790 (SEQ ID NO: 6))

```
            10         20         30         40         50         60
    MAPLCPSPWL PLLIPAPAPG LTVQLLLSLL LLVPVHPQRL PRMQEDSPLG GGSSGEDDPL 70         80         90        100        110        120
    GEEDLPSEED SPREEDPPGE EDLPGEEDLP GEEDLPEVKP KSEEEGSLKL EDLPTVEAPG 130        140        150        160        170        180
    DPQEPQNNAH RDKEGDDQSH WRYGGDPPWP RVSPACAGRF QSPVDIRPQL AAFCPALRPL 190        200        210        220        230        240
    ELLGFQLPPL PELRLRNNGH SVQLTLPPGL EMALGPGREY RALQLHLHWG AAGRPGSEHT 250        260        270        280        290        300
    VEGHRFPAEI HVVHLSTAFA RVDEALGRPG GLAVLAAFLE EGPEENSAYE QLLSRLEEIA
```

```
           310        320        330        340        350        360
EEGSETQVPG LDISALLPSD FSRYFQYEGS LTTPPCAQGV IWTVFNQTVM LSAKQLHTLS 370        380        390        400        410        420
DTLWGPGDSR LQLNFRATQP LNGRVIEASF PAGVDSSPRA AEPVQLNSCL AAGDILALVF 430        440        450
GLLFAVTSVA FLVQMRRQHR RGTKGGVSYR PAEVAETGA
```

Most preferably, the Carbonic anhydrase IX assay detects one or more soluble forms of Carbonic anhydrase IX. Carbonic anhydrase IX is a type I membrane protein having a large extracellular domain, most or all of which is present in soluble forms of Carbonic anhydrase IX generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in Carbonic anhydrase IX:

| Residues | Length | Domain ID |
|---|---|---|
| 1-37 | 37 | Signal peptide |
| 38-459 | 422 | Carbonic anhydrase IX |
| 38-414 | 377 | Extracellular |
| 415-435 | 21 | Transmembrane domain |
| 436-459 | 699 | Cytoplasmic |

As used herein, the term "C-X-C motif chemokine 2" refers to one or more polypeptides present in a biological sample that are derived from the C-X-C motif chemokine 2 precursor (Swiss-Prot P19875 (SEQ ID NO: 7)).

```
           10         20         30         40         50         60
MARATLSAAP SNPRLLRVAL LLLLLVAASR RAAGAPLATE LRCQCLQTLQ GIHLKNIQSV 70         80         90         100
KVKSPGPHCA QTEVIATLKN GQKACLNPAS PMVKKIIEKM LKNGKSN
```

The following domains have been identified in C-X-C motif chemokine 2:

| Residues | Length | Domain ID |
|---|---|---|
| 1-34 | 34 | Signal peptide |
| 35-107 | 73 | C-X-C motif chemokine 2 |
| 39-107 | 69 | GRO-beta |

As used herein, the term "relating a signal to the presence or amount" of an analyte reflects the following understanding. Assay signals are typically related to the presence or amount of an analyte through the use of a standard curve calculated using known concentrations of the analyte of interest. As the term is used herein, an assay is "configured to detect" an analyte if an assay can generate a detectable signal indicative of the presence or amount of a physiologically relevant concentration of the analyte. Because an antibody epitope is on the order of 8 amino acids, an immunoassay configured to detect a marker of interest will also detect polypeptides related to the marker sequence, so long as those polypeptides contain the epitope(s) necessary to bind to the antibody or antibodies used in the assay. The term "related marker" as used herein with regard to a biomarker such as one of the kidney injury markers described herein refers to one or more fragments, variants, etc., of a particular marker or its biosynthetic parent that may be detected as a surrogate for the marker itself or as independent biomarkers. The term also refers to one or more polypeptides present in a biological sample that are derived from the biomarker precursor complexed to additional species, such as binding proteins, receptors, heparin, lipids, sugars, etc.

In this regard, the skilled artisan will understand that the signals obtained from an immunoassay are a direct result of complexes formed between one or more antibodies and the target biomolecule (i.e., the analyte) and polypeptides containing the necessary epitope(s) to which the antibodies bind. While such assays may detect the full length biomarker and the assay result be expressed as a concentration of a biomarker of interest, the signal from the assay is actually a result of all such "immunoreactive" polypeptides present in the sample. Expression of biomarkers may also be determined by means other than immunoassays, including protein measurements (such as dot blots, western blots, chromatographic methods, mass spectrometry, etc.) and nucleic acid measurements (mRNA quatitation). This list is not meant to be limiting.

The term "positive going" marker as that term is used herein refer to a marker that is determined to be elevated in subjects suffering from a disease or condition, relative to subjects not suffering from that disease or condition. The term "negative going" marker as that term is used herein refer to a marker that is determined to be reduced in subjects suffering from a disease or condition, relative to subjects not suffering from that disease or condition.

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology.

Preferably, an analyte is measured in a sample. Such a sample may be obtained from a subject, or may be obtained from biological materials intended to be provided to the subject. For example, a sample may be obtained from a kidney being evaluated for possible transplantation into a subject, and an analyte measurement used to evaluate the kidney for preexisting damage. Preferred samples are body fluid samples.

The term "body fluid sample" as used herein refers to a sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a kidney injury marker of the present invention, optionally together with other clinical characteristics, to arrive at a diagnosis (that is, the occurrence or nonoccurrence) of an acute renal injury or ARF for the subject from which a sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity (e.g., worsening renal function, future ARF, or death) is referred to as being "indicative of an increased likelihood" of an adverse outcome in a patient.

Marker Assays

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and The Immunoassay Handbook, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGel™ resins (Rapp Polymere GmbH), AgroGel™ resins (I.L.S.A. Industria Lavorazione Sottoprodotti Animali S.P.A.), polyethylene glycol and acrylamide (PEGA) gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of the described kidney injury markers. The kit comprises reagents for the analysis of at least one test sample which comprise at least one antibody that a kidney injury marker. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Antibodies used in the immunoassays described herein preferably specifically bind to a kidney injury marker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{12}$ $M^{-1}$.

Affinity is calculated as $K_d = k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: $r/c=K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Numerous publications discuss the use of phage display technology to produce and screen libraries of polypeptides for binding to a selected analyte. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

While the present application describes antibody-based binding assays in detail, alternatives to antibodies as binding species in assays are well known in the art. These include receptors for a particular target, aptamers, etc. Aptamers are oligonucleic acid or peptide molecules that bind to a specific target molecule. Aptamers are usually created by selecting them from a large random sequence pool, but natural aptamers also exist. High-affinity aptamers containing modified nucleotides conferring improved characteristics on the ligand, such as improved in vivo stability or improved delivery characteristics. Examples of such modifications include chemical substitutions at the ribose and/or phosphate and/or base positions, and may include amino acid side chain functionalities.

Assay Correlations

The term "correlating" as used herein in reference to the use of biomarkers refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the 97.5th percentile of the concentration seen in a normal population. Another method may be to look at serial samples from the same patient, where a prior "baseline" result is used to monitor for temporal changes in a biomarker level.

Population studies may also be used to select a decision threshold. Reciever Operating Characteristic ("ROC") arose from the field of signal detection theory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1-specificity, the ROC graph is sometimes called the sensitivity vs (1-specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a subject belongs to one classification out of a plurality of classifications.

Measures of test accuracy may be obtained as described in Fischer et al., *Intensive Care Med.* 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1-specificity)) of greater than 1, at least 2, more preferably at least 3, still more preferably at least 5, and most preferably at least 10; and or a negative likelihood ratio (calculated as (1-sensitivity)/specificity) of less than 1, less than or equal to 0.5, more preferably less than or equal to 0.3, and most preferably less than or equal to 0.1

Additional clinical indicia may be combined with the kidney injury marker assay result(s) of the present invention. These include other biomarkers related to renal status. Examples include the following, which recite the common biomarker name, followed by the Swiss-Prot entry number for that biomarker or its parent: Actin (P68133); Adenosine deaminase binding protein (DPP4, P27487); Alpha-1-acid glycoprotein 1 (P02763); Alpha-1-microglobulin (P02760); Albumin (P02768); Angiotensinogenase (Renin, P00797); Annexin A2 (P07355); Beta-glucuronidase (P08236); B-2-microglobulin (P61679); Beta-galactosidase (P16278); BMP-7 (P18075); Brain natriuretic peptide (proBNP, BNP-32, NTproBNP; P16860); Calcium-binding protein Beta (S100-beta, P04271); Carbonic anhydrase (Q16790); Casein Kinase 2 (P68400); Ceruloplasmin (P00450); Clusterin (P10909); Complement C3 (P01024); Cysteine-rich protein (CYR61, O00622); Cytochrome C(P99999); Epidermal growth factor (EGF, P01133); Endothelin-1 (P05305); Exosomal Fetuin-A (P02765); Fatty acid-binding protein, heart (FABP3, P05413); Fatty acid-binding protein, liver (P07148); Ferritin (light chain, P02793; heavy chain P02794); Fructose-1,6-biphosphatase (P09467); GRO-alpha (CXCL1, (P09341); Growth Hormone (P01241); Hepatocyte growth factor (P14210); Insulin-like growth factor I (P01343); Immunoglobulin G; Immunoglobulin Light Chains (Kappa and Lambda); Interferon gamma (P01308); Lysozyme (P61626); Interleukin-1alpha (P01583); Interleukin-2 (P60568); Interleukin-4 (P60568); Interleukin-9 (P15248); Interleukin-12p40 (P29460); Interleukin-13 (P35225); Interleukin-16 (Q14005); L1 cell adhesion molecule (P32004); Lactate dehydrogenase (P00338); Leucine Aminopeptidase (P28838); Meprin A-alpha subunit (Q16819); Meprin A-beta subunit (Q16820); Midkine (P21741); MIP2-alpha (CXCL2, P19875); MMP-2 (P08253); MMP-9 (P14780); Netrin-1 (O95631); Neutral endopeptidase (P08473); Osteopontin (P10451); Renal papillary antigen 1 (RPA1); Renal papillary antigen 2 (RPA2); Retinol binding protein (P09455); Ribonuclease; S100 calcium-binding protein A6 (P06703); Serum Amyloid P Component (P02743); Sodium/Hydrogen exchanger isoform (NHE3, P48764); Spermidine/spermine N1-acetyltransferase (P21673); TGF-Beta1 (P01137); Transferrin (P02787); Trefoil factor 3 (TFF3, Q07654); Toll-Like protein 4 (O00206); Total protein; Tubulointerstitial nephritis antigen (Q9UJW2); Uromodulin (Tamm-Horsfall protein, P07911).

For purposes of risk stratification, Adiponectin (Q15848); Alkaline phosphatase (P05186); Aminopeptidase N(P15144); CalbindinD28k (P05937); Cystatin C(P01034); 8 subunit of FIFO ATPase (P03928); Gamma-glutamyltransferase (P19440); GSTa (alpha-glutathione-S-transferase, P08263); GSTpi (Glutathione-S-transferase P; GST class-pi; P09211); IGFBP-1 (P08833); IGFBP-2 (P18065); IGFBP-6 (P24592); Integral membrane protein 1 (Itm 1, P46977); Interleukin-6 (P05231); Interleukin-8 (P10145); Interleukin-18 (Q14116); IP-10 (10 kDa interferon-gamma-induced protein, P02778); IRPR (IFRD1, O00458); Isovaleryl-CoA dehydrogenase (IVD, P26440); I-TAC/CXCL11 (O14625); Keratin 19 (P08727); Kim-1 (Hepatitis A virus cellular receptor 1, O43656); L-arginine:glycine amidinotransferase (P50440); Leptin (P41159); Lipocalin2 (NGAL, P80188); MCP-1 (P13500); MIG (Gamma-interferon-induced monokine Q07325); MIP-1a (P10147); MIP-3a (P78556); MIP-1beta (P13236); MIP-1d (Q16663); NAG (N-acetyl-beta-D-glucosaminidase, P54802); Organic ion transporter (OCT2, O15244); Osteoprotegerin (O14788); P8 protein (O60356); Plasminogen activator inhibitor 1 (PAI-1, O05121); ProANP (1-98) (P01160); Protein phosphatase 1-beta (PPI-beta, P62140); Rab GDI-beta (P50395); Renal kallikrein (Q86U61); RT1.B-1 (alpha) chain of the integral membrane protein (Q5Y7A8); Soluble tumor necrosis factor receptor superfamily member 1A (sTNFR-I, P19438); Soluble tumor necrosis factor receptor superfamily member 1B (sTNFR-II, P20333); Tissue inhibitor of metalloproteinases 3 (TIMP-3, P35625); uPAR (Q03405) may be combined with the kidney injury marker assay result(s) of the present invention.

Other clinical indicia which may be combined with the kidney injury marker assay result(s) of the present invention includes demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a urine total protein measurement, a glomerular filtration rate, an estimated glomerular filtration rate, a urine production rate, a serum or plasma creatinine concentration, a renal papillary antigen 1 (RPA1) measurement; a renal papillary antigen 2 (RPA2) measurement; a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, and/or a renal failure index calculated as urine sodium/(urine creatinine/plasma creatinine). Other measures of renal function which may be combined with the kidney injury marker assay result(s) are described hereinafter and in Harrison's Principles of Internal Medicine, $17^{th}$ Ed., McGraw Hill, New York, pages 1741-1830, and Current Medical Diagnosis & Treatment 2008, $47^{th}$ Ed, McGraw Hill, New York, pages 785-815, each of which are hereby incorporated by reference in their entirety.

Combining assay results/clinical indicia in this manner can comprise the use of multivariate logistical regression, loglinear modeling, neural network analysis, n-of-m analysis, decision tree analysis, etc. This list is not meant to be limiting.

Diagnosis of Acute Renal Failure

As noted above, the terms "acute renal (or kidney) injury" and "acute renal (or kidney) failure" as used herein are defined in part in terms of changes in serum creatinine from a baseline value. Most definitions of ARF have common elements, including the use of serum creatinine and, often, urine output. Patients may present with renal dysfunction without an available baseline measure of renal function for use in this comparison. In such an event, one may estimate a baseline serum creatinine value by assuming the patient initially had a normal GFR. Glomerular filtration rate (GFR) is the volume of fluid filtered from the renal (kidney)

glomerular capillaries into the Bowman's capsule per unit time. Glomerular filtration rate (GFR) can be calculated by measuring any chemical that has a steady level in the blood, and is freely filtered but neither reabsorbed nor secreted by the kidneys. GFR is typically expressed in units of ml/min:

$$GFR = \frac{\text{Urine Concentration} \times \text{Urine Flow}}{\text{Plasma Concentration}}$$

By normalizing the GFR to the body surface area, a GFR of approximately 75-100 ml/min per 1.73 m² can be assumed. The rate therefore measured is the quantity of the substance in the urine that originated from a calculable volume of blood.

There are several different techniques used to calculate or estimate the glomerular filtration rate (GFR or eGFR). In clinical practice, however, creatinine clearance is used to measure GFR. Creatinine is produced naturally by the body (creatinine is a metabolite of creatine, which is found in muscle). It is freely filtered by the glomerulus, but also actively secreted by the renal tubules in very small amounts such that creatinine clearance overestimates actual GFR by 10-20%. This margin of error is acceptable considering the ease with which creatinine clearance is measured.

Creatinine clearance (CCr) can be calculated if values for creatinine's urine concentration ($U_{Cr}$), urine flow rate (V), and creatinine's plasma concentration ($P_{Cr}$) are known. Since the product of urine concentration and urine flow rate yields creatinine's excretion rate, creatinine clearance is also said to be its excretion rate ($U_{Cr} \times V$) divided by its plasma concentration. This is commonly represented mathematically as:

$$C_{Cr} = \frac{U_{Cr} \times V}{P_{Cr}}$$

Commonly a 24 hour urine collection is undertaken, from empty-bladder one morning to the contents of the bladder the following morning, with a comparative blood test then taken:

$$C_{Cr} = \frac{U_{Cr} \times \text{24-hour volume}}{P_{Cr} \times 24 \times 60 \text{ mins}}$$

To allow comparison of results between people of different sizes, the CCr is often corrected for the body surface area (BSA) and expressed compared to the average sized man as ml/min/1.73 m2. While most adults have a BSA that approaches 1.7 (1.6-1.9), extremely obese or slim patients should have their CCr corrected for their actual BSA:

$$C_{Cr-corrected} = \frac{C_{Cr} \times 1.73}{BSA}$$

The accuracy of a creatinine clearance measurement (even when collection is complete) is limited because as glomerular filtration rate (GFR) falls creatinine secretion is increased, and thus the rise in serum creatinine is less. Thus, creatinine excretion is much greater than the filtered load, resulting in a potentially large overestimation of the GFR (as much as a twofold difference). However, for clinical purposes it is important to determine whether renal function is stable or getting worse or better. This is often determined by monitoring serum creatinine alone. Like creatinine clearance, the serum creatinine will not be an accurate reflection of GFR in the non-steady-state condition of ARF. Nonetheless, the degree to which serum creatinine changes from baseline will reflect the change in GFR. Serum creatinine is readily and easily measured and it is specific for renal function.

For purposes of determining urine output on a Urine output on a mL/kg/hr basis, hourly urine collection and measurement is adequate. In the case where, for example, only a cumulative 24-h output was available and no patient weights are provided, minor modifications of the RIFLE urine output criteria have been described. For example, Bagshaw et al., *Nephrol. Dial. Transplant.* 23: 1203-1210, 2008, assumes an average patient weight of 70 kg, and patients are assigned a RIFLE classification based on the following: <35 mL/h (Risk), <21 mL/h (Injury) or <4 mL/h (Failure).

Selecting a Treatment Regimen

Once a diagnosis is obtained, the clinician can readily select a treatment regimen that is compatible with the diagnosis, such as initiating renal replacement therapy, withdrawing delivery of compounds that are known to be damaging to the kidney, kidney transplantation, delaying or avoiding procedures that are known to be damaging to the kidney, modifying diuretic administration, initiating goal directed therapy, etc. The skilled artisan is aware of appropriate treatments for numerous diseases discussed in relation to the methods of diagnosis described herein. See, e.g., Merck Manual of Diagnosis and Therapy, 17th Ed. Merck Research Laboratories, Whitehouse Station, N.J., 1999. In addition, since the methods and compositions described herein provide prognostic information, the markers of the present invention may be used to monitor a course of treatment. For example, improved or worsened prognostic state may indicate that a particular treatment is or is not efficacious.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

EXAMPLE 1

Contrast-induced Nephropathy Sample Collection

The objective of this sample collection study is to collect samples of plasma and urine and clinical data from patients before and after receiving intravascular contrast media. Approximately 250 adults undergoing radiographic/angiographic procedures involving intravascular administration of iodinated contrast media are enrolled. To be enrolled in the study, each patient must meet all of the following inclusion criteria and none of the following exclusion criteria:

Inclusion Criteria males and females 18 years of age or older;

undergoing a radiographic/angiographic procedure (such as a CT scan or coronary intervention) involving the intravascular administration of contrast media;

expected to be hospitalized for at least 48 hours after contrast administration.

able and willing to provide written informed consent for study participation and to comply with all study procedures.

Exclusion Criteria renal transplant recipients;

acutely worsening renal function prior to the contrast procedure;

already receiving dialysis (either acute or chronic) or in imminent need of dialysis at enrollment;

expected to undergo a major surgical procedure (such as involving cardiopulmonary bypass) or an additional imaging procedure with contrast media with significant risk for further renal insult within the 48 hrs following contrast administration;

participation in an interventional clinical study with an experimental therapy within the previous 30 days;

known infection with human immunodeficiency virus (HIV) or a hepatitis virus.

Immediately prior to the first contrast administration (and after any pre-procedure hydration), an EDTA anti-coagulated blood sample (10 mL) and a urine sample (10 mL) are collected from each patient. Blood and urine samples are then collected at 4 (±0.5), 8 (±1), 24 (±2) 48 (±2), and 72 (±2) hrs following the last administration of contrast media during the index contrast procedure. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Serum creatinine is assessed at the site immediately prior to the first contrast administration (after any pre-procedure hydration) and at 4 (±0.5), 8 (±1), 24 (±2) and 48 (±2)), and 72 (±2) hours following the last administration of contrast (ideally at the same time as the study samples are obtained). In addition, each patient's status is evaluated through day 30 with regard to additional serum and urine creatinine measurements, a need for dialysis, hospitalization status, and adverse clinical outcomes (including mortality).

Prior to contrast administration, each patient is assigned a risk based on the following assessment: systolic blood pressure<80 mm Hg=5 points; intra-arterial balloon pump=5 points; congestive heart failure (Class III-IV or history of pulmonary edema)=5 points; age>75 yrs=4 points; hematocrit level<39% for men, <35% for women=3 points; diabetes=3 points; contrast media volume=1 point for each 100 mL; serum creatinine level>1.5 g/dL=4 points OR estimated GFR 40-60 mL/min/1.73 m²=2 points, 20-40 mL/min/1.73 m²=4 points, <20 mL/min/1.73 m²=6 points. The risks assigned are as follows: risk for CIN and dialysis: 5 or less total points=risk of CIN—7.5%, risk of dialysis—0.04%; 6-10 total points=risk of CIN—14%, risk of dialysis—0.12%; 11-16 total points=risk of CIN—26.1%, risk of dialysis—1.09%; >16 total points=risk of CIN—57.3%, risk of dialysis—12.8%.

EXAMPLE 2

Cardiac Surgery Sample Collection

The objective of this sample collection study is to collect samples of plasma and urine and clinical data from patients before and after undergoing cardiovascular surgery, a procedure known to be potentially damaging to kidney function. Approximately 900 adults undergoing such surgery are enrolled. To be enrolled in the study, each patient must meet all of the following inclusion criteria and none of the following exclusion criteria:

Inclusion Criteria males and females 18 years of age or older;

undergoing cardiovascular surgery;

Toronto/Ottawa Predictive Risk Index for Renal Replacement risk score of at least 2 (Wijeysundera et al., *JAMA* 297: 1801-9, 2007); and able and willing to provide written informed consent for study participation and to comply with all study procedures.

Exclusion Criteria known pregnancy;

previous renal transplantation;

acutely worsening renal function prior to enrollment (e.g., any category of RIFLE criteria);

already receiving dialysis (either acute or chronic) or in imminent need of dialysis at enrollment;

currently enrolled in another clinical study or expected to be enrolled in another clinical study within 7 days of cardiac surgery that involves drug infusion or a therapeutic intervention for AKI;

known infection with human immunodeficiency virus (HIV) or a hepatitis virus.

Within 3 hours prior to the first incision (and after any pre-procedure hydration), an EDTA anti-coagulated blood sample (10 mL), whole blood (3 mL), and a urine sample (35 mL) are collected from each patient. Blood and urine samples are then collected at 3 (±0.5), 6 (±0.5), 12 (±1), 24 (±2) and 48 (±2) hrs following the procedure and then daily on days 3 through 7 if the subject remains in the hospital. Blood is collected via direct venipuncture or via other available venous access, such as an existing femoral sheath, central venous line, peripheral intravenous line or hep-lock. These study blood samples are frozen and shipped to Astute Medical, Inc., San Diego, Calif. The study urine samples are frozen and shipped to Astute Medical, Inc.

EXAMPLE 3

Acutely Ill Subject Sample Collection

The objective of this study is to collect samples from acutely ill patients. Approximately 900 adults expected to be in the ICU for at least 48 hours will be enrolled. To be enrolled in the study, each patient must meet all of the following inclusion criteria and none of the following exclusion criteria:

Inclusion Criteria males and females 18 years of age or older;

Study population 1: approximately 300 patients that have at least one of:

shock (SBP<90 mmHg and/or need for vasopressor support to maintain MAP>60 mmHg and/or documented drop in SBP of at least 40 mmHg); and sepsis;

Study population 2: approximately 300 patients that have at least one of:

IV antibiotics ordered in computerized physician order entry (CPOE) within 24 hours of enrollment;

contrast media exposure within 24 hours of enrollment;

increased Intra-Abdominal Pressure with acute decompensated heart failure; and severe trauma as the primary reason for ICU admission and likely to be hospitalized in the ICU for 48 hours after enrollment;

Study population 3: approximately 300 patients expected to be hospitalized through acute care setting (ICU or ED) with a known risk factor for acute renal injury (e.g. sepsis, hypotension/shock (Shock=systolic BP<90 mmHg and/or the need for vasopressor support to maintain a MAP>60 mmHg and/or a documented drop in SBP>40 mmHg), major trauma, hemorrhage, or major surgery); and/or expected to be hospitalized to the ICU for at least 24 hours after enrollment.

Exclusion Criteria known pregnancy;

institutionalized individuals;

previous renal transplantation;

known acutely worsening renal function prior to enrollment (e.g., any category of RIFLE criteria);

received dialysis (either acute or chronic) within 5 days prior to enrollment or in imminent need of dialysis at the time of enrollment;

known infection with human immunodeficiency virus (HIV) or a hepatitis virus;

meets only the SBP<90 mmHg inclusion criterion set forth above, and does not have shock in the attending physician's or principal investigator's opinion.

After providing informed consent, an EDTA anti-coagulated blood sample (10 mL) and a urine sample (25-30 mL) are collected from each patient. Blood and urine samples are then collected at 4 (±0.5) and 8 (±1) hours after contrast administration (if applicable); at 12 (±1), 24 (±2), and 48 (±2) hours after enrollment, and thereafter daily up to day 7 to day 14 while the subject is hospitalized. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

EXAMPLE 4

Immunoassay Format

Analytes are measured using standard sandwich enzyme immunoassay techniques. A first antibody which binds the analyte is immobilized in wells of a 96 well polystyrene microplate. Analyte standards and test samples are pipetted into the appropriate wells and any analyte present is bound by the immobilized antibody. After washing away any unbound substances, a horseradish peroxidase-conjugated second antibody which binds the analyte is added to the wells, thereby forming sandwich complexes with the analyte (if present) and the first antibody. Following a wash to remove any unbound antibody-enzyme reagent, a substrate solution comprising tetramethylbenzidine and hydrogen peroxide is added to the wells. Color develops in proportion to the amount of analyte present in the sample. The color development is stopped and the intensity of the color is measured at 540 nm or 570 nm. An analyte concentration is assigned to the test sample by comparison to a standard curve determined from the analyte standards. Concentrations reported below are as follows: Cathepsin B ng/mL; Renin pg/mL; Dipeptidyl Peptidase IV (soluble form) ng/mL; Neprilysin (soluble form) ng/mL; Beta-2-microglobulin μg/mL; Carbonic anhydrase IX (soluble form) ng/mL; and C-X-C motif chemokine 2 pg/mL.

EXAMPLE 5

Apparently Healthy Donor and Chronic Disease Patient Samples

Human urine samples from donors with no known chronic or acute disease ("Apparently Healthy Donors") were purchased from two vendors (Golden West Biologicals, Inc., 27625 Commerce Center Dr., Temecula, Calif. 92590 and Virginia Medical Research, Inc., 915 First Colonial Rd., Virginia Beach, Va. 23454). The urine samples were shipped and stored frozen at less than −20° C. The vendors supplied demographic information for the individual donors including gender, race (Black/White), smoking status and age.

Human urine samples from donors with various chronic diseases ("Chronic Disease Patients") including congestive heart failure, coronary artery disease, chronic kidney disease, chronic obstructive pulmonary disease, diabetes mellitus and hypertension were purchased from Virginia Medical Research, Inc., 915 First Colonial Rd., Virginia Beach, Va. 23454. The urine samples were shipped and stored frozen at less than −20 degrees centigrade. The vendor provided a case report form for each individual donor with age, gender, race (Black/White), smoking status and alcohol use, height, weight, chronic disease(s) diagnosis, current medications and previous surgeries.

EXAMPLE 6

Use of Kidney Injury Markers for Evaluating Renal Status in Patients

Patients from the intensive care unit (ICU) were enrolled in the following study. Each patient was classified by kidney status as non-injury (0), risk of injury (R), injury (I), and failure (F) according to the maximum stage reached within 7 days of enrollment as determined by the RIFLE criteria. EDTA anti-coagulated blood samples (10 mL) and a urine samples (25-30 mL) were collected from each patient at enrollment, 4 (±0.5) and 8 (±1) hours after contrast administration (if applicable); at 12 (±1), 24 (±2), and 48 (±2) hours after enrollment, and thereafter daily up to day 7 to day 14 while the subject is hospitalized. Markers were each measured by standard immunoassay methods using commercially available assay reagents in the urine samples and the plasma component of the blood samples collected.

Two cohorts were defined to represent a "diseased" and a "normal" population. While these terms are used for convenience, "diseased" and "normal" simply represent two cohorts for comparison (say RIFLE 0 vs RIFLE R, I and F; RIFLE 0 vs RIFLE R; RIFLE 0 and R vs RIFLE I and F; etc.). The time "prior max stage" represents the time at which a sample is collected, relative to the time a particular patient reaches the lowest disease stage as defined for that cohort, binned into three groups which are +/−12 hours. For example, "24 hr prior" which uses 0 vs R, I, F as the two cohorts would mean 24 hr (+/−12 hours) prior to reaching stage R (or I if no sample at R, or F if no sample at R or I).

A receiver operating characteristic (ROC) curve was generated for each biomarker measured and the area under each ROC curve (AUC) is determined. Patients in Cohort 2 were also separated according to the reason for adjudication to cohort 2 as being based on serum creatinine measurements (sCr), being based on urine output (UO), or being based on either serum creatinine measurements or urine output. Using the same example discussed above (0 vs R, I, F), for those patients adjudicated to stage R, I, or F on the basis of serum creatinine measurements alone, the stage 0 cohort may include patients adjudicated to stage R, I, or F on the basis of urine output; for those patients adjudicated to stage R, I, or F on the basis of urine output alone, the stage 0 cohort may include patients adjudicated to stage R, I, or F on the basis of serum creatinine measurements; and for those patients adjudicated to stage R, I, or F on the basis of serum creatinine measurements or urine output, the stage 0 cohort contains only patients in stage 0 for both serum creatinine measurements and urine output. Also, in the data for patients adjudicated on the basis of serum creatinine measurements or urine output, the adjudication method which yielded the most severe RIFLE stage is used.

The ability to distinguish cohort 1 from Cohort 2 was determined using ROC analysis. SE is the standard error of the AUC, n is the number of sample or individual patients ("pts," as indicated). Standard errors are calculated as described in Hanley, J. A., and McNeil, B. J., The meaning and use of the area under a receiver operating characteristic (ROC) curve. Radiology (1982) 143: 29-36; p values are calculated with a two-tailed Z-test. An AUC<0.5 is indicative of a negative going marker for the comparison, and an AUC>0.5 is indicative of a positive going marker for the comparison.

Various threshold (or "cutoff") concentrations were selected, and the associated sensitivity and specificity for distinguishing cohort 1 from cohort 2 are determined. OR is the odds ratio calculated for the particular cutoff concentration, and 95% CI is the confidence interval for the odds ratio.

TABLE 1

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | Beta-2-microglobulin | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| | sCr or UO | | | | | |
| Median | 1.44 | 4.76 | 1.44 | 2.61 | 1.44 | 4.70 |
| Average | 2.57 | 3.52 | 2.57 | 2.83 | 2.57 | 3.36 |
| Stdev | 2.43 | 2.58 | 2.43 | 2.53 | 2.43 | 2.39 |
| p(t-test) | | 0.014 | | 0.48 | | 0.11 |
| Min | 0.00152 | 0.00403 | 0.00152 | 0.00212 | 0.00152 | 0.0378 |
| Max | 6.10 | 6.10 | 6.10 | 6.07 | 6.10 | 5.80 |
| n (Samp) | 255 | 48 | 255 | 57 | 255 | 27 |
| n (Patient) | 103 | 48 | 103 | 57 | 103 | 27 |
| | sCr only | | | | | |
| Median | 1.43 | 0.462 | 1.43 | 0.763 | 1.43 | 1.24 |
| Average | 2.59 | 2.48 | 2.59 | 2.51 | 2.59 | 2.07 |
| Stdev | 2.45 | 2.78 | 2.45 | 2.68 | 2.45 | 2.33 |
| p(t-test) | | 0.86 | | 0.89 | | 0.45 |
| Min | 0.00152 | 0.00925 | 0.00152 | 0.0114 | 0.00152 | 0.0324 |
| Max | 6.10 | 6.10 | 6.10 | 5.80 | 6.10 | 5.80 |
| n (Samp) | 447 | 16 | 447 | 21 | 447 | 13 |
| n (Patient) | 170 | 16 | 170 | 21 | 170 | 13 |
| | UO only | | | | | |
| Median | 1.39 | 4.57 | 1.39 | 2.61 | 1.39 | 4.82 |
| Average | 2.56 | 3.58 | 2.56 | 2.90 | 2.56 | 3.51 |
| Stdev | 2.44 | 2.45 | 2.44 | 2.50 | 2.44 | 2.41 |
| p(t-test) | | 0.010 | | 0.37 | | 0.064 |
| Min | 0.00152 | 0.00403 | 0.00152 | 0.00212 | 0.00152 | 0.0378 |
| Max | 6.10 | 6.10 | 6.10 | 6.07 | 6.10 | 5.80 |
| n (Samp) | 218 | 46 | 218 | 51 | 218 | 25 |
| n (Patient) | 87 | 46 | 87 | 51 | 87 | 25 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.59 | 0.45 | 0.60 | 0.51 | 0.46 | 0.51 | 0.57 | 0.45 | 0.58 |
| SE | 0.046 | 0.075 | 0.048 | 0.043 | 0.066 | 0.045 | 0.060 | 0.083 | 0.063 |
| p | 0.044 | 0.53 | 0.031 | 0.83 | 0.59 | 0.79 | 0.25 | 0.55 | 0.19 |
| nCohort 1 | 255 | 447 | 218 | 255 | 447 | 218 | 255 | 447 | 218 |
| nCohort 2 | 48 | 16 | 46 | 57 | 21 | 51 | 27 | 13 | 25 |
| Cutoff 1 | 0.734 | 0.0999 | 1.48 | 0.278 | 0.153 | 0.278 | 1.22 | 0.171 | 1.02 |
| Sens 1 | 71% | 75% | 72% | 70% | 71% | 71% | 70% | 77% | 72% |
| Spec 1 | 40% | 17% | 51% | 27% | 21% | 27% | 48% | 23% | 46% |
| Cutoff 2 | 0.0999 | 0.0513 | 0.278 | 0.0999 | 0.0851 | 0.152 | 0.213 | 0.0743 | 0.354 |
| Sens 2 | 81% | 81% | 80% | 81% | 81% | 80% | 81% | 85% | 80% |
| Spec 2 | 14% | 11% | 27% | 14% | 15% | 19% | 24% | 14% | 31% |
| Cutoff 3 | 0.0273 | 0.0197 | 0.0298 | 0.0246 | 0.0372 | 0.0168 | 0.0683 | 0.0683 | 0.141 |
| Sens 3 | 92% | 94% | 91% | 91% | 90% | 90% | 93% | 92% | 92% |
| Spec 3 | 4% | 4% | 5% | 3% | 8% | 2% | 10% | 13% | 18% |
| Cutoff 4 | 5.08 | 5.13 | 5.16 | 5.08 | 5.13 | 5.16 | 5.08 | 5.13 | 5.16 |
| Sens 4 | 48% | 38% | 43% | 37% | 38% | 37% | 41% | 23% | 36% |
| Spec 4 | 70% | 70% | 70% | 70% | 70% | 70% | 70% | 70% | 70% |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| Cutoff 5 | 5.80 | 5.80 | 5.80 | 5.80 | 5.80 | 5.80 | 5.80 | 5.80 | 5.80 |
| Sens 5 | 17% | 6% | 17% | 2% | 0% | 2% | 0% | 0% | 0% |
| Spec 5 | 95% | 95% | 94% | 95% | 95% | 94% | 95% | 95% | 94% |
| Cutoff 6 | 5.80 | 5.80 | 5.80 | 5.80 | 5.80 | 5.80 | 5.80 | 5.80 | 5.80 |
| Sens 6 | 17% | 6% | 17% | 2% | 0% | 2% | 0% | 0% | 0% |
| Spec 6 | 95% | 95% | 94% | 95% | 95% | 94% | 95% | 95% | 94% |
| OR Quart 2 | 0.41 | 0.39 | 0.52 | 0.57 | 0.49 | 0.51 | 0.47 | 1.0 | 0.57 |
| p Value | 0.12 | 0.27 | 0.26 | 0.20 | 0.32 | 0.17 | 0.30 | 1.0 | 0.45 |
| 95% CI of | 0.14 | 0.074 | 0.16 | 0.24 | 0.12 | 0.20 | 0.11 | 0.20 | 0.13 |
| OR Quart2 | 1.2 | 2.0 | 1.6 | 1.3 | 2.0 | 1.3 | 2.0 | 5.1 | 2.5 |
| OR Quart 3 | 1.1 | 0.59 | 2.2 | 0.85 | 0.83 | 1.4 | 1.8 | 1.0 | 1.9 |
| p Value | 0.85 | 0.48 | 0.084 | 0.68 | 0.76 | 0.42 | 0.29 | 1.0 | 0.28 |
| 95% CI of | 0.45 | 0.14 | 0.90 | 0.38 | 0.24 | 0.63 | 0.61 | 0.20 | 0.60 |
| OR Quart3 | 2.7 | 2.5 | 5.4 | 1.9 | 2.8 | 3.1 | 5.2 | 5.1 | 6.1 |
| OR Quart 4 | 2.1 | 1.2 | 1.9 | 1.1 | 1.2 | 0.73 | 1.4 | 1.3 | 1.7 |
| p Value | 0.080 | 0.75 | 0.18 | 0.84 | 0.78 | 0.48 | 0.59 | 0.70 | 0.40 |
| 95% CI of | 0.92 | 0.36 | 0.75 | 0.50 | 0.38 | 0.30 | 0.44 | 0.29 | 0.51 |
| OR Quart4 | 4.7 | 4.1 | 4.6 | 2.3 | 3.6 | 1.8 | 4.1 | 6.2 | 5.4 |

C-X-C motif chemokine 2

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| | sCr or UO | | | | | |
| Median | 0.135 | 2.51 | 0.135 | 4.01 | 0.135 | 0.0260 |
| Average | 8.01 | 11.4 | 8.01 | 12.4 | 8.01 | 7.85 |
| Stdev | 26.5 | 27.8 | 26.5 | 30.9 | 26.5 | 19.6 |
| p(t-test) | | 0.32 | | 0.17 | | 0.97 |
| Min | 0.00804 | 0.0260 | 0.00804 | 0.0260 | 0.00804 | 0.0260 |
| Max | 266 | 217 | 266 | 217 | 266 | 111 |
| n (Samp) | 360 | 75 | 360 | 91 | 360 | 43 |
| n (Patient) | 190 | 75 | 190 | 91 | 190 | 43 |
| | sCr only | | | | | |
| Median | 0.536 | 2.64 | 0.536 | 4.37 | 0.536 | 3.34 |
| Average | 8.92 | 17.6 | 8.92 | 17.4 | 8.92 | 6.53 |
| Stdev | 25.5 | 42.4 | 25.5 | 40.9 | 25.5 | 8.89 |
| p(t-test) | | 0.083 | | 0.058 | | 0.65 |
| Min | 0.00804 | 0.0260 | 0.00804 | 0.0260 | 0.00804 | 0.0260 |
| Max | 266 | 217 | 266 | 217 | 266 | 36.2 |
| n (Samp) | 755 | 29 | 755 | 37 | 755 | 23 |
| n (Patient) | 295 | 29 | 295 | 37 | 295 | 23 |
| | UO only | | | | | |
| Median | 0.262 | 2.64 | 0.262 | 5.28 | 0.262 | 0.0260 |
| Average | 7.67 | 12.4 | 7.67 | 14.9 | 7.67 | 9.52 |
| Stdev | 25.1 | 29.6 | 25.1 | 33.2 | 25.1 | 21.4 |
| p(t-test) | | 0.18 | | 0.035 | | 0.67 |
| Min | 0.00804 | 0.0260 | 0.00804 | 0.0260 | 0.00804 | 0.0260 |
| Max | 266 | 217 | 266 | 217 | 266 | 111 |
| n (Samp) | 315 | 65 | 315 | 78 | 315 | 36 |
| n (Patient) | 134 | 65 | 134 | 78 | 134 | 36 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.61 | 0.61 | 0.62 | 0.62 | 0.61 | 0.64 | 0.49 | 0.57 | 0.49 |
| SE | 0.037 | 0.057 | 0.040 | 0.034 | 0.050 | 0.037 | 0.047 | 0.063 | 0.051 |
| p | 0.0039 | 0.049 | 0.0025 | 5.8E−4 | 0.025 | 9.7E−5 | 0.82 | 0.27 | 0.83 |
| nCohort 1 | 360 | 755 | 315 | 360 | 755 | 315 | 360 | 755 | 315 |
| nCohort 2 | 75 | 29 | 65 | 91 | 37 | 78 | 43 | 23 | 36 |
| Cutoff 1 | 0.00804 | 0.244 | 0.299 | 0.00804 | 0.00804 | 0.299 | 0.00804 | 0.00804 | 0.00804 |
| Sens 1 | 100% | 72% | 71% | 100% | 100% | 71% | 100% | 100% | 100% |
| Spec 1 | 0% | 46% | 51% | 0% | 0% | 51% | 0% | 0% | 0% |
| Cutoff 2 | 0.00804 | 0.00804 | 0.00804 | 0.00804 | 0.00804 | 0.00804 | 0.00804 | 0.00804 | 0.00804 |
| Sens 2 | 100% | 100% | 100% | 100% | 100% | 100% | 100% | 100% | 100% |
| Spec 2 | 0% | 0% | 0% | 0% | 0% | 0% | 0% | 0% | 0% |
| Cutoff 3 | 0.00804 | 0.00804 | 0.00804 | 0.00804 | 0.00804 | 0.00804 | 0.00804 | 0.00804 | 0.00804 |
| Sens 3 | 100% | 100% | 100% | 100% | 100% | 100% | 100% | 100% | 100% |
| Spec 3 | 0% | 0% | 0% | 0% | 0% | 0% | 0% | 0% | 0% |
| Cutoff 4 | 3.08 | 3.96 | 3.82 | 3.08 | 3.96 | 3.82 | 3.08 | 3.96 | 3.82 |
| Sens 4 | 45% | 38% | 45% | 52% | 54% | 55% | 37% | 43% | 28% |
| Spec 4 | 70% | 70% | 70% | 70% | 70% | 70% | 70% | 70% | 70% |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| Cutoff 5 | 6.49 | 7.98 | 7.00 | 6.49 | 7.98 | 7.00 | 6.49 | 7.98 | 7.00 |
| Sens 5 | 36% | 31% | 38% | 37% | 35% | 40% | 23% | 30% | 25% |
| Spec 5 | 80% | 80% | 80% | 80% | 80% | 80% | 80% | 80% | 80% |
| Cutoff 6 | 15.4 | 20.2 | 14.9 | 15.4 | 20.2 | 14.9 | 15.4 | 20.2 | 14.9 |
| Sens 6 | 23% | 21% | 25% | 19% | 22% | 24% | 19% | 4% | 25% |
| Spec 6 | 90% | 90% | 90% | 90% | 90% | 90% | 90% | 90% | 90% |
| OR Quart 2 | 0.14 | >9.4 | 0.25 | >44 | >13 | 3.1 | 0.89 | >9.4 | 0.76 |
| p Value | 4.8E−4 | <0.034 | 0.010 | <2.2E−4 | <0.015 | 0.015 | 0.81 | <0.034 | 0.60 |
| 95% CI of | 0.047 | >1.2 | 0.090 | >5.9 | >1.6 | 1.2 | 0.35 | >1.2 | 0.27 |
| OR Quart2 | 0.42 | na | 0.72 | na | na | 7.8 | 2.3 | na | 2.1 |
| OR Quart 3 | 0.78 | >12 | 1.1 | >30 | >11 | 3.3 | 0.78 | >5.1 | 0.10 |
| p Value | 0.47 | <0.019 | 0.85 | <9.4E−4 | <0.025 | 0.0097 | 0.62 | <0.14 | 0.031 |
| 95% CI of | 0.40 | >1.5 | 0.51 | >4.0 | >1.3 | 1.3 | 0.30 | >0.59 | 0.012 |
| OR Quart3 | 1.5 | na | 2.2 | na | na | 8.3 | 2.1 | na | 0.81 |
| OR Quart 4 | 1.3 | >9.4 | 1.6 | >50 | >16 | 6.2 | 1.7 | >9.4 | 2.5 |
| p Value | 0.36 | <0.034 | 0.16 | <1.3E−4 | <0.0073 | 4.4E−5 | 0.20 | <0.034 | 0.040 |
| 95% CI of | 0.72 | >1.2 | 0.82 | >6.7 | >2.1 | 2.6 | 0.75 | >1.2 | 1.0 |
| OR Quart4 | 2.5 | na | 3.3 | na | na | 15 | 4.0 | na | 5.8 |

Renin

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | | | | | | |
|---|---|---|---|---|---|---|
| Median | 319 | 494 | 319 | 483 | 319 | 323 |
| Average | 750 | 886 | 750 | 1350 | 750 | 1120 |
| Stdev | 1270 | 1110 | 1270 | 3110 | 1270 | 1660 |
| p(t-test) | | 0.53 | | 0.073 | | 0.20 |
| Min | 1.00E−9 | 1.00E−9 | 1.00E−9 | 1.00E−9 | 1.00E−9 | 1.00E−9 |
| Max | 9810 | 5150 | 9810 | 21100 | 9810 | 5550 |
| n (Samp) | 121 | 45 | 121 | 50 | 121 | 26 |
| n (Patient) | 98 | 45 | 98 | 50 | 98 | 26 | sCr only

| | | | | | | |
|---|---|---|---|---|---|---|
| Median | 394 | 254 | 394 | 565 | 394 | 304 |
| Average | 978 | 1150 | 978 | 1340 | 978 | 985 |
| Stdev | 1840 | 1760 | 1840 | 1670 | 1840 | 1460 |
| p(t-test) | | 0.75 | | 0.40 | | 0.99 |
| Min | 1.00E−9 | 1.00E−9 | 1.00E−9 | 1.00E−9 | 1.00E−9 | 1.00E−9 |
| Max | 21100 | 4570 | 21100 | 5380 | 21100 | 4250 |
| n (Samp) | 259 | 12 | 259 | 19 | 259 | 13 |
| n (Patient) | 159 | 12 | 159 | 19 | 159 | 13 |

UO only

| | | | | | | |
|---|---|---|---|---|---|---|
| Median | 297 | 638 | 297 | 606 | 297 | 385 |
| Average | 758 | 996 | 758 | 1540 | 758 | 1290 |
| Stdev | 1340 | 1100 | 1340 | 3230 | 1340 | 1710 |
| p(t-test) | | 0.31 | | 0.035 | | 0.10 |
| Min | 1.00E−9 | 1.00E−9 | 1.00E−9 | 1.00E−9 | 1.00E−9 | 1.00E−9 |
| Max | 9810 | 5150 | 9810 | 21100 | 9810 | 5550 |
| n (Samp) | 106 | 42 | 106 | 46 | 106 | 23 |
| n (Patient) | 82 | 42 | 82 | 46 | 82 | 23 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.58 | 0.46 | 0.64 | 0.57 | 0.56 | 0.63 | 0.53 | 0.47 | 0.59 |
| SE | 0.051 | 0.087 | 0.052 | 0.049 | 0.070 | 0.051 | 0.063 | 0.083 | 0.068 |
| p | 0.12 | 0.65 | 0.0072 | 0.13 | 0.42 | 0.012 | 0.59 | 0.76 | 0.21 |
| nCohort 1 | 121 | 259 | 106 | 121 | 259 | 106 | 121 | 259 | 106 |
| nCohort 2 | 45 | 12 | 42 | 50 | 19 | 46 | 26 | 13 | 23 |
| Cutoff 1 | 234 | 161 | 279 | 203 | 84.2 | 211 | 123 | 137 | 123 |
| Sens 1 | 71% | 75% | 71% | 70% | 74% | 72% | 73% | 77% | 74% |
| Spec 1 | 40% | 29% | 46% | 38% | 20% | 41% | 31% | 28% | 32% |
| Cutoff 2 | 177 | 34.5 | 224 | 111 | 34.5 | 134 | 10.6 | 0 | 10.6 |
| Sens 2 | 80% | 83% | 81% | 80% | 84% | 80% | 81% | 100% | 83% |
| Spec 2 | 36% | 15% | 41% | 30% | 15% | 33% | 21% | 0% | 20% |
| Cutoff 3 | 10.1 | 0 | 131 | 65.6 | 0 | 88.6 | 0 | 0 | 7.32 |
| Sens 3 | 91% | 100% | 90% | 90% | 100% | 91% | 100% | 100% | 91% |
| Spec 3 | 21% | 0% | 33% | 27% | 0% | 28% | 0% | 0% | 18% |
| Cutoff 4 | 606 | 881 | 600 | 606 | 881 | 600 | 606 | 881 | 600 |
| Sens 4 | 44% | 25% | 52% | 42% | 42% | 50% | 31% | 31% | 39% |
| Spec 4 | 70% | 70% | 71% | 70% | 70% | 71% | 70% | 70% | 71% |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| Cutoff 5 | 1130 | 1590 | 1130 | 1130 | 1590 | 1130 | 1130 | 1590 | 1130 |
| Sens 5 | 22% | 25% | 29% | 30% | 37% | 35% | 31% | 23% | 39% |
| Spec 5 | 80% | 80% | 80% | 80% | 80% | 80% | 80% | 80% | 80% |
| Cutoff 6 | 1990 | 2390 | 2060 | 1990 | 2390 | 2060 | 1990 | 2390 | 2060 |
| Sens 6 | 13% | 25% | 14% | 16% | 16% | 22% | 23% | 15% | 22% |
| Spec 6 | 90% | 90% | 91% | 90% | 90% | 91% | 90% | 90% | 91% |
| OR Quart 2 | 2.9 | 0.66 | 6.1 | 2.1 | 0.15 | 2.5 | 0.97 | 0.66 | 0.56 |
| p Value | 0.052 | 0.65 | 0.0089 | 0.16 | 0.085 | 0.11 | 0.96 | 0.65 | 0.45 |
| 95% CI of | 0.99 | 0.11 | 1.6 | 0.75 | 0.018 | 0.81 | 0.28 | 0.11 | 0.12 |
| OR Quart2 | 8.6 | 4.1 | 24 | 5.6 | 1.3 | 7.5 | 3.3 | 4.1 | 2.6 |
| OR Quart 3 | 2.1 | 1.4 | 5.4 | 1.6 | 0.65 | 2.5 | 0.97 | 1.7 | 1.2 |
| p Value | 0.18 | 0.70 | 0.015 | 0.34 | 0.51 | 0.11 | 0.96 | 0.47 | 0.74 |
| 95% CI of | 0.71 | 0.29 | 1.4 | 0.59 | 0.17 | 0.81 | 0.28 | 0.39 | 0.34 |
| OR Quart3 | 6.5 | 6.3 | 21 | 4.6 | 2.4 | 7.5 | 3.3 | 7.5 | 4.6 |
| OR Quart 4 | 2.9 | 1.0 | 6.9 | 2.5 | 1.4 | 3.9 | 1.4 | 1.0 | 2.0 |
| p Value | 0.052 | 0.99 | 0.0052 | 0.067 | 0.59 | 0.014 | 0.59 | 1.0 | 0.26 |
| 95% CI of | 0.99 | 0.20 | 1.8 | 0.94 | 0.44 | 1.3 | 0.43 | 0.19 | 0.60 |
| OR Quart4 | 8.6 | 5.2 | 27 | 6.8 | 4.1 | 11 | 4.5 | 5.1 | 6.9 |

Cathepsin B

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | Cohort 1 | Cohort 2 | Cohort 1 | Cohort 2 | Cohort 1 | Cohort 2 |
|---|---|---|---|---|---|---|
| Median | 0.504 | 0.628 | 0.504 | 1.15 | 0.504 | 0.649 |
| Average | 2.26 | 1.84 | 2.26 | 5.00 | 2.26 | 4.06 |
| Stdev | 8.48 | 2.68 | 8.48 | 11.8 | 8.48 | 15.2 |
| p(t-test) | | 0.74 | | 0.084 | | 0.40 |
| Min | 1.00E−9 | 1.00E−9 | 1.00E−9 | 1.00E−9 | 1.00E−9 | 1.00E−9 |
| Max | 72.4 | 11.0 | 72.4 | 64.9 | 72.4 | 78.1 |
| n (Samp) | 131 | 47 | 131 | 50 | 131 | 26 |
| n (Patient) | 102 | 47 | 102 | 50 | 102 | 26 | sCr only

| | Cohort 1 | Cohort 2 | Cohort 1 | Cohort 2 | Cohort 1 | Cohort 2 |
|---|---|---|---|---|---|---|
| Median | 0.657 | 0.485 | 0.657 | 1.92 | 0.657 | 0.338 |
| Average | 2.89 | 1.92 | 2.89 | 4.95 | 2.89 | 1.27 |
| Stdev | 9.57 | 2.68 | 9.57 | 7.48 | 9.57 | 1.85 |
| p(t-test) | | 0.71 | | 0.36 | | 0.55 |
| Min | 1.00E−9 | 1.00E−9 | 1.00E−9 | 1.00E−9 | 1.00E−9 | 0.0682 |
| Max | 78.1 | 7.84 | 78.1 | 29.7 | 78.1 | 6.19 |
| n (Samp) | 269 | 14 | 269 | 19 | 269 | 13 |
| n (Patient) | 162 | 14 | 162 | 19 | 162 | 13 |

UO only

| | Cohort 1 | Cohort 2 | Cohort 1 | Cohort 2 | Cohort 1 | Cohort 2 |
|---|---|---|---|---|---|---|
| Median | 0.539 | 0.951 | 0.539 | 1.32 | 0.539 | 0.846 |
| Average | 2.37 | 2.21 | 2.37 | 5.79 | 2.37 | 5.24 |
| Stdev | 8.90 | 2.91 | 8.90 | 12.6 | 8.90 | 16.1 |
| p(t-test) | | 0.91 | | 0.052 | | 0.23 |
| Min | 1.00E−9 | 1.00E−9 | 1.00E−9 | 1.00E−9 | 1.00E−9 | 1.00E−9 |
| Max | 72.4 | 11.6 | 72.4 | 64.9 | 72.4 | 78.1 |
| n (Samp) | 118 | 44 | 118 | 46 | 118 | 23 |
| n (Patient) | 87 | 44 | 87 | 46 | 87 | 23 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.56 | 0.48 | 0.62 | 0.63 | 0.67 | 0.65 | 0.50 | 0.46 | 0.56 |
| SE | 0.050 | 0.080 | 0.051 | 0.048 | 0.070 | 0.050 | 0.062 | 0.084 | 0.067 |
| p | 0.25 | 0.83 | 0.021 | 0.0072 | 0.015 | 0.0032 | 0.98 | 0.64 | 0.41 |
| nCohort 1 | 131 | 269 | 118 | 131 | 269 | 118 | 131 | 269 | 118 |
| nCohort 2 | 47 | 14 | 44 | 50 | 19 | 46 | 26 | 13 | 23 |
| Cutoff 1 | 0.339 | 0.142 | 0.546 | 0.665 | 0.797 | 0.665 | 0.185 | 0.265 | 0.185 |
| Sens 1 | 70% | 71% | 70% | 70% | 74% | 72% | 73% | 77% | 74% |
| Spec 1 | 40% | 18% | 51% | 58% | 55% | 56% | 21% | 28% | 21% |
| Cutoff 2 | 0.140 | 0.0513 | 0.309 | 0.245 | 0.265 | 0.268 | 0.105 | 0.128 | 0.0764 |
| Sens 2 | 81% | 86% | 82% | 80% | 84% | 80% | 81% | 85% | 83% |
| Spec 2 | 18% | 14% | 37% | 30% | 28% | 31% | 17% | 17% | 12% |
| Cutoff 3 | 0 | 0 | 0.0764 | 0 | 0 | 0 | 0 | 0.0901 | 0 |
| Sens 3 | 100% | 100% | 91% | 100% | 100% | 100% | 100% | 92% | 100% |
| Spec 3 | 0% | 0% | 12% | 0% | 0% | 0% | 0% | 15% | 0% |
| Cutoff 4 | 1.16 | 1.35 | 1.17 | 1.16 | 1.35 | 1.17 | 1.16 | 1.35 | 1.17 |
| Sens 4 | 36% | 36% | 45% | 50% | 63% | 54% | 27% | 23% | 39% |
| Spec 4 | 70% | 70% | 70% | 70% | 70% | 70% | 70% | 70% | 70% |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| Cutoff 5 | 1.81 | 2.07 | 2.02 | 1.81 | 2.07 | 2.02 | 1.81 | 2.07 | 2.02 |
| Sens 5 | 28% | 36% | 30% | 38% | 42% | 41% | 19% | 23% | 30% |
| Spec 5 | 80% | 80% | 81% | 80% | 80% | 81% | 80% | 80% | 81% |
| Cutoff 6 | 3.53 | 4.65 | 3.53 | 3.53 | 4.65 | 3.53 | 3.53 | 4.65 | 3.53 |
| Sens 6 | 19% | 14% | 20% | 26% | 26% | 28% | 15% | 8% | 30% |
| Spec 6 | 90% | 90% | 91% | 90% | 90% | 91% | 90% | 90% | 91% |
| OR Quart 2 | 0.85 | 0.19 | 2.9 | 0.44 | 1.5 | 0.49 | 1.7 | 1.0 | 0.24 |
| p Value | 0.75 | 0.13 | 0.071 | 0.16 | 0.65 | 0.25 | 0.36 | 0.99 | 0.092 |
| 95% CI of | 0.31 | 0.021 | 0.91 | 0.14 | 0.25 | 0.15 | 0.54 | 0.20 | 0.047 |
| OR Quart2 | 2.3 | 1.7 | 9.2 | 1.4 | 9.4 | 1.6 | 5.3 | 5.2 | 1.3 |
| OR Quart 3 | 1.4 | 0.38 | 3.0 | 1.9 | 1.5 | 1.8 | 0.47 | 1.4 | 1.0 |
| p Value | 0.47 | 0.26 | 0.062 | 0.17 | 0.65 | 0.22 | 0.31 | 0.70 | 1.0 |
| 95% CI of | 0.55 | 0.072 | 0.94 | 0.76 | 0.25 | 0.69 | 0.11 | 0.29 | 0.31 |
| OR Quart3 | 3.7 | 2.0 | 9.5 | 4.9 | 9.4 | 4.9 | 2.0 | 6.3 | 3.2 |
| OR Quart 4 | 1.7 | 1.2 | 4.0 | 2.5 | 6.3 | 2.8 | 1.5 | 1.0 | 0.97 |
| p Value | 0.27 | 0.74 | 0.016 | 0.054 | 0.019 | 0.037 | 0.52 | 0.99 | 0.95 |
| 95% CI of | 0.66 | 0.36 | 1.3 | 0.99 | 1.3 | 1.1 | 0.46 | 0.20 | 0.30 |
| OR Quart4 | 4.3 | 4.3 | 13 | 6.2 | 30 | 7.3 | 4.7 | 5.2 | 3.1 |

Neprilysin

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 1.26 | 0.949 | 1.26 | 1.03 | nd | nd |
| Average | 4.09 | 2.29 | 4.09 | 5.48 | nd | nd |
| Stdev | 8.95 | 3.70 | 8.95 | 13.1 | nd | nd |
| p(t-test) | | 0.40 | | 0.60 | nd | nd |
| Min | 0.0532 | 0.0313 | 0.0532 | 0.0902 | nd | nd |
| Max | 51.0 | 16.0 | 51.0 | 46.3 | nd | nd |
| n (Samp) | 62 | 19 | 62 | 19 | nd | nd |
| n (Patient) | 50 | 19 | 50 | 19 | nd | nd |
| UO only | | | | | | |
| Median | 0.963 | 0.949 | 0.963 | 0.896 | nd | nd |
| Average | 2.98 | 2.47 | 2.98 | 5.23 | nd | nd |
| Stdev | 6.67 | 4.11 | 6.67 | 12.8 | nd | nd |
| p(t-test) | | 0.78 | | 0.33 | nd | nd |
| Min | 0.0532 | 0.0313 | 0.0532 | 0.0203 | nd | nd |
| Max | 35.3 | 16.0 | 35.3 | 46.3 | nd | nd |
| n (Samp) | 52 | 15 | 52 | 20 | nd | nd |
| n (Patient) | 41 | 15 | 41 | 20 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.43 | nd | 0.47 | 0.47 | nd | 0.50 | nd | nd | nd |
| SE | 0.077 | nd | 0.086 | 0.077 | nd | 0.077 | nd | nd | nd |
| p | 0.38 | nd | 0.69 | 0.74 | nd | 0.99 | nd | nd | nd |
| nCohort 1 | 62 | nd | 52 | 62 | nd | 52 | nd | nd | nd |
| nCohort 2 | 19 | nd | 15 | 19 | nd | 20 | nd | nd | nd |
| Cutoff 1 | 0.279 | nd | 0.376 | 0.586 | nd | 0.690 | nd | nd | nd |
| Sens 1 | 74% | nd | 73% | 74% | nd | 70% | nd | nd | nd |
| Spec 1 | 8% | nd | 15% | 23% | nd | 31% | nd | nd | nd |
| Cutoff 2 | 0.238 | nd | 0.251 | 0.351 | nd | 0.461 | nd | nd | nd |
| Sens 2 | 84% | nd | 80% | 84% | nd | 80% | nd | nd | nd |
| Spec 2 | 8% | nd | 8% | 15% | nd | 21% | nd | nd | nd |
| Cutoff 3 | 0.117 | nd | 0.0869 | 0.178 | nd | 0.306 | nd | nd | nd |
| Sens 3 | 95% | nd | 93% | 95% | nd | 90% | nd | nd | nd |
| Spec 3 | 5% | nd | 4% | 6% | nd | 10% | nd | nd | nd |
| Cutoff 4 | 1.99 | nd | 1.45 | 1.99 | nd | 1.45 | nd | nd | nd |
| Sens 4 | 37% | nd | 33% | 21% | nd | 35% | nd | nd | nd |
| Spec 4 | 71% | nd | 71% | 71% | nd | 71% | nd | nd | nd |
| Cutoff 5 | 3.50 | nd | 2.26 | 3.50 | nd | 2.26 | nd | nd | nd |
| Sens 5 | 21% | nd | 33% | 16% | nd | 15% | nd | nd | nd |
| Spec 5 | 81% | nd | 81% | 81% | nd | 81% | nd | nd | nd |
| Cutoff 6 | 10.1 | nd | 4.43 | 10.1 | nd | 4.43 | nd | nd | nd |
| Sens 6 | 5% | nd | 13% | 11% | nd | 10% | nd | nd | nd |
| Spec 6 | 90% | nd | 90% | 90% | nd | 90% | nd | nd | nd |
| OR Quart 2 | 0.44 | nd | 0.51 | 1.4 | nd | 1.8 | nd | nd | nd |
| p Value | 0.30 | nd | 0.42 | 0.65 | nd | 0.46 | nd | nd | nd |
| 95% CI of | 0.094 | nd | 0.10 | 0.32 | nd | 0.40 | nd | nd | nd |
| OR Quart2 | 2.1 | nd | 2.6 | 6.3 | nd | 7.7 | nd | nd | nd |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| OR Quart 3 | 0.44 | nd | 0.32 | 1.1 | nd | 1.3 | nd | nd | nd |
| p Value | 0.30 | nd | 0.22 | 0.94 | nd | 0.70 | nd | nd | nd |
| 95% CI of | 0.094 | nd | 0.053 | 0.23 | nd | 0.30 | nd | nd | nd |
| OR Quart3 | 2.1 | nd | 1.9 | 5.0 | nd | 6.1 | nd | nd | nd |
| OR Quart 4 | 1.3 | nd | 1.1 | 1.8 | nd | 1.3 | nd | nd | nd |
| p Value | 0.66 | nd | 0.91 | 0.42 | nd | 0.70 | nd | nd | nd |
| 95% CI of | 0.36 | nd | 0.25 | 0.43 | nd | 0.30 | nd | nd | nd |
| OR Quart4 | 5.0 | nd | 4.8 | 7.8 | nd | 6.1 | nd | nd | nd |

Carbonic anhydrase IX

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | Cohort 1 | Cohort 2 | Cohort 1 | Cohort 2 | Cohort 1 | Cohort 2 |
|---|---|---|---|---|---|---|
| Median | 0.00525 | 0.00780 | 0.00525 | 0.0170 | nd | nd |
| Average | 0.0125 | 0.0158 | 0.0125 | 0.0706 | nd | nd |
| Stdev | 0.0182 | 0.0196 | 0.0182 | 0.193 | nd | nd |
| p(t-test) | | 0.51 | | 0.020 | nd | nd |
| Min | 1.00E-9 | 0.000522 | 1.00E-9 | 0.00216 | nd | nd |
| Max | 0.119 | 0.0760 | 0.119 | 0.859 | nd | nd |
| n (Samp) | 62 | 19 | 62 | 19 | nd | nd |
| n (Patient) | 50 | 19 | 50 | 19 | nd | nd |

UO only

| | Cohort 1 | Cohort 2 | Cohort 1 | Cohort 2 | Cohort 1 | Cohort 2 |
|---|---|---|---|---|---|---|
| Median | 0.00432 | 0.0111 | 0.00432 | 0.0204 | nd | nd |
| Average | 0.0112 | 0.0178 | 0.0112 | 0.0693 | nd | nd |
| Stdev | 0.0189 | 0.0211 | 0.0189 | 0.188 | nd | nd |
| p(t-test) | | 0.25 | | 0.029 | nd | nd |
| Min | 1.00E-9 | 0.000522 | 1.00E-9 | 0.00216 | nd | nd |
| Max | 0.119 | 0.0760 | 0.119 | 0.859 | nd | nd |
| n (Samp) | 52 | 15 | 52 | 20 | nd | nd |
| n (Patient) | 41 | 15 | 41 | 20 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.54 | nd | 0.63 | 0.73 | nd | 0.81 | nd | nd | nd |
| SE | 0.077 | nd | 0.085 | 0.072 | nd | 0.063 | nd | nd | nd |
| p | 0.60 | nd | 0.12 | 0.0017 | nd | 8.1E-7 | nd | nd | nd |
| nCohort 1 | 62 | nd | 52 | 62 | nd | 52 | nd | nd | nd |
| nCohort 2 | 19 | nd | 15 | 19 | nd | 20 | nd | nd | nd |
| Cutoff 1 | 0.00269 | nd | 0.00444 | 0.0102 | nd | 0.0158 | nd | nd | nd |
| Sens 1 | 74% | nd | 73% | 74% | nd | 70% | nd | nd | nd |
| Spec 1 | 26% | nd | 52% | 61% | nd | 83% | nd | nd | nd |
| Cutoff 2 | 0.00187 | nd | 0.00269 | 0.00548 | nd | 0.0114 | nd | nd | nd |
| Sens 2 | 84% | nd | 80% | 84% | nd | 80% | nd | nd | nd |
| Spec 2 | 15% | nd | 35% | 52% | nd | 71% | nd | nd | nd |
| Cutoff 3 | 0.000712 | nd | 0.00105 | 0.00337 | nd | 0.00548 | nd | nd | nd |
| Sens 3 | 95% | nd | 93% | 95% | nd | 90% | nd | nd | nd |
| Spec 3 | 6% | nd | 13% | 32% | nd | 56% | nd | nd | nd |
| Cutoff 4 | 0.0121 | nd | 0.0114 | 0.0121 | nd | 0.0114 | nd | nd | nd |
| Sens 4 | 42% | nd | 47% | 58% | nd | 80% | nd | nd | nd |
| Spec 4 | 71% | nd | 71% | 71% | nd | 71% | nd | nd | nd |
| Cutoff 5 | 0.0183 | nd | 0.0143 | 0.0183 | nd | 0.0143 | nd | nd | nd |
| Sens 5 | 32% | nd | 47% | 42% | nd | 75% | nd | nd | nd |
| Spec 5 | 81% | nd | 81% | 81% | nd | 81% | nd | nd | nd |
| Cutoff 6 | 0.0293 | nd | 0.0212 | 0.0293 | nd | 0.0212 | nd | nd | nd |
| Sens 6 | 16% | nd | 20% | 26% | nd | 50% | nd | nd | nd |
| Spec 6 | 90% | nd | 90% | 90% | nd | 90% | nd | nd | nd |
| OR Quart 2 | 1.0 | nd | 1.5 | 3.4 | nd | 2.1 | nd | nd | nd |
| p Value | 1.0 | nd | 0.68 | 0.31 | nd | 0.55 | nd | nd | nd |
| 95% CI of | 0.21 | nd | 0.22 | 0.32 | nd | 0.18 | nd | nd | nd |
| OR Quart2 | 4.7 | nd | 10 | 35 | nd | 26 | nd | nd | nd |
| OR Quart 3 | 1.3 | nd | 1.5 | 10 | nd | 8.5 | nd | nd | nd |
| p Value | 0.71 | nd | 0.68 | 0.039 | nd | 0.061 | nd | nd | nd |
| 95% CI of | 0.30 | nd | 0.22 | 1.1 | nd | 0.90 | nd | nd | nd |
| OR Quart3 | 5.9 | nd | 10 | 93 | nd | 80 | nd | nd | nd |
| OR Quart 4 | 1.6 | nd | 4.9 | 12 | nd | 27 | nd | nd | nd |
| p Value | 0.52 | nd | 0.078 | 0.028 | nd | 0.0039 | nd | nd | nd |
| 95% CI of | 0.38 | nd | 0.84 | 1.3 | nd | 2.9 | nd | nd | nd |
| OR Quart4 | 6.8 | nd | 29 | 110 | nd | 250 | nd | nd | nd |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | Dipeptidyl peptidase IV | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| | sCr or UO | | | | | |
| Median | 147 | 435 | 147 | 237 | 147 | 239 |
| Average | 7480 | 1090 | 7480 | 423 | 7480 | 852 |
| Stdev | 67000 | 2170 | 67000 | 468 | 67000 | 1110 |
| p(t-test) | | 0.60 | | 0.53 | | 0.64 |
| Min | 0.200 | 0.899 | 0.200 | 3.65 | 0.200 | 2.62 |
| Max | 677000 | 11000 | 677000 | 1480 | 677000 | 4320 |
| n (Samp) | 102 | 31 | 102 | 36 | 102 | 22 |
| n (Patient) | 82 | 31 | 82 | 36 | 82 | 22 |
| | sCr only | | | | | |
| Median | 266 | 147 | 266 | 130 | 266 | 96.7 |
| Average | 4260 | 927 | 4260 | 672 | 4260 | 1030 |
| Stdev | 47800 | 2100 | 47800 | 1270 | 47800 | 1670 |
| p(t-test) | | 0.82 | | 0.80 | | 0.84 |
| Min | 0.200 | 6.52 | 0.200 | 18.2 | 0.200 | 10.1 |
| Max | 677000 | 7150 | 677000 | 4460 | 677000 | 4950 |
| n (Samp) | 201 | 11 | 201 | 12 | 201 | 9 |
| n (Patient) | 131 | 11 | 131 | 12 | 131 | 9 |
| | UO only | | | | | |
| Median | 121 | 577 | 121 | 312 | 121 | 328 |
| Average | 536 | 1260 | 536 | 463 | 536 | 888 |
| Stdev | 1240 | 2270 | 1240 | 451 | 1240 | 1120 |
| p(t-test) | | 0.030 | | 0.74 | | 0.24 |
| Min | 0.200 | 0.899 | 0.200 | 3.65 | 0.200 | 2.62 |
| Max | 9980 | 11000 | 9980 | 1410 | 9980 | 4320 |
| n (Samp) | 93 | 28 | 93 | 35 | 93 | 20 |
| n (Patient) | 71 | 28 | 71 | 35 | 71 | 20 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.57 | 0.48 | 0.63 | 0.53 | 0.49 | 0.60 | 0.61 | 0.53 | 0.65 |
| SE | 0.060 | 0.091 | 0.063 | 0.057 | 0.086 | 0.058 | 0.069 | 0.100 | 0.072 |
| p | 0.23 | 0.79 | 0.038 | 0.60 | 0.91 | 0.086 | 0.12 | 0.79 | 0.038 |
| nCohort 1 | 102 | 201 | 93 | 102 | 201 | 93 | 102 | 201 | 93 |
| nCohort 2 | 31 | 11 | 28 | 36 | 12 | 35 | 22 | 9 | 20 |
| Cutoff 1 | 58.9 | 58.9 | 62.9 | 58.9 | 52.2 | 104 | 93.8 | 78.9 | 95.2 |
| Sens 1 | 71% | 73% | 71% | 72% | 75% | 71% | 73% | 78% | 70% |
| Spec 1 | 37% | 32% | 39% | 37% | 31% | 49% | 44% | 35% | 47% |
| Cutoff 2 | 20.7 | 52.2 | 19.1 | 36.5 | 42.6 | 52.2 | 83.4 | 52.2 | 83.4 |
| Sens 2 | 81% | 82% | 82% | 81% | 83% | 80% | 82% | 89% | 80% |
| Spec 2 | 24% | 31% | 23% | 29% | 29% | 35% | 41% | 31% | 44% |
| Cutoff 3 | 6.52 | 12.4 | 6.36 | 9.55 | 36.5 | 9.55 | 42.6 | 9.55 | 42.6 |
| Sens 3 | 90% | 91% | 93% | 92% | 92% | 91% | 91% | 100% | 90% |
| Spec 3 | 12% | 15% | 12% | 15% | 26% | 15% | 34% | 13% | 33% |
| Cutoff 4 | 538 | 677 | 407 | 538 | 677 | 407 | 538 | 677 | 407 |
| Sens 4 | 48% | 27% | 61% | 33% | 25% | 40% | 36% | 33% | 45% |
| Spec 4 | 71% | 70% | 71% | 71% | 70% | 71% | 71% | 70% | 71% |
| Cutoff 5 | 1110 | 1110 | 698 | 1110 | 1110 | 698 | 1110 | 1110 | 698 |
| Sens 5 | 23% | 18% | 43% | 11% | 17% | 26% | 32% | 33% | 40% |
| Spec 5 | 80% | 80% | 81% | 80% | 80% | 81% | 80% | 80% | 81% |
| Cutoff 6 | 1960 | 1990 | 1560 | 1960 | 1990 | 1560 | 1960 | 1990 | 1560 |
| Sens 6 | 13% | 9% | 18% | 0% | 8% | 0% | 14% | 11% | 25% |
| Spec 6 | 90% | 90% | 90% | 90% | 90% | 90% | 90% | 90% | 90% |
| OR Quart 2 | 0.83 | 1.0 | 0.23 | 1.9 | 1.0 | 0.66 | 4.2 | 5.3 | 2.8 |
| p Value | 0.76 | 1.0 | 0.088 | 0.29 | 0.98 | 0.52 | 0.089 | 0.13 | 0.24 |
| 95% CI of | 0.24 | 0.14 | 0.044 | 0.59 | 0.14 | 0.19 | 0.80 | 0.60 | 0.50 |
| OR Quart2 | 2.8 | 7.4 | 1.2 | 5.9 | 7.5 | 2.4 | 22 | 47 | 16 |
| OR Quart 3 | 1.2 | 2.7 | 1.0 | 1.9 | 4.0 | 2.1 | 2.8 | 0 | 2.8 |
| p Value | 0.77 | 0.26 | 1.0 | 0.26 | 0.096 | 0.18 | 0.24 | na | 0.24 |
| 95% CI of | 0.38 | 0.49 | 0.30 | 0.62 | 0.78 | 0.71 | 0.50 | na | 0.50 |
| OR Quart3 | 3.8 | 14 | 3.3 | 6.1 | 20 | 6.5 | 16 | na | 16 |
| OR Quart 4 | 1.5 | 1.0 | 2.1 | 1.9 | 0.50 | 1.9 | 5.0 | 3.1 | 5.0 |
| p Value | 0.44 | 1.0 | 0.20 | 0.29 | 0.58 | 0.27 | 0.054 | 0.34 | 0.058 |
| 95% CI of | 0.51 | 0.14 | 0.68 | 0.59 | 0.044 | 0.62 | 0.98 | 0.31 | 0.95 |
| OR Quart4 | 4.7 | 7.4 | 6.3 | 5.9 | 5.7 | 5.7 | 26 | 30 | 26 |

TABLE 2

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | Beta-2-microglobulin | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| | sCr or UO | | | | | |
| Median | 1.75 | 3.29 | 1.75 | 0.538 | 1.75 | 0.362 |
| Average | 2.67 | 2.85 | 2.67 | 2.11 | 2.67 | 1.46 |
| Stdev | 2.47 | 2.38 | 2.47 | 2.56 | 2.47 | 1.95 |
| p(t-test) | | 0.73 | | 0.21 | | 0.046 |
| Min | 0.00152 | 0.00181 | 0.00152 | 0.00212 | 0.00152 | 0.00546 |
| Max | 6.10 | 6.10 | 6.10 | 6.10 | 6.10 | 5.80 |
| n (Samp) | 421 | 25 | 421 | 33 | 421 | 17 |
| n (Patient) | 165 | 25 | 165 | 33 | 165 | 17 |
| | sCr only | | | | | |
| Median | nd | nd | 1.47 | 3.95 | 1.47 | 0.763 |
| Average | nd | nd | 2.57 | 3.27 | 2.57 | 1.33 |
| Stdev | nd | nd | 2.45 | 2.75 | 2.45 | 1.42 |
| p(t-test) | nd | nd | | 0.43 | | 0.18 |
| Min | nd | nd | 0.00152 | 0.0843 | 0.00152 | 0.0324 |
| Max | nd | nd | 6.10 | 5.80 | 6.10 | 3.49 |
| n (Samp) | nd | nd | 511 | 8 | 511 | 7 |
| n (Patient) | nd | nd | 198 | 8 | 198 | 7 |
| | UO only | | | | | |
| Median | 1.81 | 3.29 | 1.81 | 0.721 | 1.81 | 0.261 |
| Average | 2.73 | 2.89 | 2.73 | 1.92 | 2.73 | 1.84 |
| Stdev | 2.48 | 2.35 | 2.48 | 2.38 | 2.48 | 2.40 |
| p(t-test) | | 0.74 | | 0.093 | | 0.15 |
| Min | 0.00152 | 0.00181 | 0.00152 | 0.00212 | 0.00152 | 0.00546 |
| Max | 6.10 | 6.10 | 6.10 | 6.10 | 6.10 | 5.80 |
| n (Samp) | 357 | 25 | 357 | 29 | 357 | 17 |
| n (Patient) | 135 | 25 | 135 | 29 | 135 | 17 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.52 | nd | 0.51 | 0.43 | 0.57 | 0.41 | 0.33 | 0.39 | 0.35 |
| SE | 0.060 | nd | 0.060 | 0.054 | 0.11 | 0.057 | 0.073 | 0.11 | 0.074 |
| p | 0.75 | nd | 0.84 | 0.21 | 0.48 | 0.11 | 0.024 | 0.35 | 0.040 |
| nCohort 1 | 421 | nd | 357 | 421 | 511 | 357 | 421 | 511 | 357 |
| nCohort 2 | 25 | nd | 25 | 33 | 8 | 29 | 17 | 7 | 17 |
| Cutoff 1 | 0.363 | nd | 0.363 | 0.153 | 0.518 | 0.152 | 0.107 | 0.476 | 0.107 |
| Sens 1 | 72% | nd | 72% | 73% | 75% | 72% | 71% | 71% | 71% |
| Spec 1 | 33% | nd | 31% | 22% | 37% | 19% | 17% | 36% | 15% |
| Cutoff 2 | 0.278 | nd | 0.278 | 0.0572 | 0.200 | 0.0497 | 0.0376 | 0.153 | 0.0351 |
| Sens 2 | 80% | nd | 80% | 82% | 88% | 83% | 82% | 86% | 82% |
| Spec 2 | 29% | nd | 27% | 10% | 26% | 9% | 7% | 23% | 7% |
| Cutoff 3 | 0.0351 | nd | 0.0351 | 0.0319 | 0.0830 | 0.00312 | 0.0124 | 0.0319 | 0.0124 |
| Sens 3 | 92% | nd | 92% | 91% | 100% | 93% | 94% | 100% | 94% |
| Spec 3 | 7% | nd | 7% | 6% | 16% | 1% | 3% | 7% | 2% |
| Cutoff 4 | 5.48 | nd | 5.57 | 5.48 | 5.13 | 5.57 | 5.48 | 5.13 | 5.57 |
| Sens 4 | 24% | nd | 20% | 30% | 50% | 24% | 6% | 0% | 18% |
| Spec 4 | 70% | nd | 70% | 70% | 70% | 70% | 70% | 70% | 70% |
| Cutoff 5 | 5.80 | nd | 5.80 | 5.80 | 5.80 | 5.80 | 5.80 | 5.80 | 5.80 |
| Sens 5 | 12% | nd | 12% | 6% | 0% | 7% | 0% | 0% | 0% |
| Spec 5 | 94% | nd | 94% | 94% | 94% | 94% | 94% | 94% | 94% |
| Cutoff 6 | 5.80 | nd | 5.80 | 5.80 | 5.80 | 5.80 | 5.80 | 5.80 | 5.80 |
| Sens 6 | 12% | nd | 12% | 6% | 0% | 7% | 0% | 0% | 0% |
| Spec 6 | 94% | nd | 94% | 94% | 94% | 94% | 94% | 94% | 94% |
| OR Quart 2 | 1.8 | nd | 0.99 | 0.19 | 2.0 | 0.66 | 4.2 | >2.0 | 2.1 |
| p Value | 0.37 | nd | 0.99 | 0.033 | 0.57 | 0.53 | 0.21 | <0.56 | 0.41 |
| 95% CI of | 0.51 | nd | 0.28 | 0.040 | 0.18 | 0.18 | 0.46 | >0.18 | 0.37 |
| OR Quart2 | 6.3 | nd | 3.5 | 0.88 | 22 | 2.4 | 38 | na | 12 |
| OR Quart 3 | 2.6 | nd | 2.6 | 0.89 | 2.0 | 1.4 | 4.1 | >3.1 | 1.5 |
| p Value | 0.11 | nd | 0.084 | 0.81 | 0.57 | 0.58 | 0.21 | <0.33 | 0.65 |
| 95% CI of | 0.80 | nd | 0.88 | 0.35 | 0.18 | 0.45 | 0.45 | >0.32 | 0.25 |
| OR Quart3 | 8.7 | nd | 7.7 | 2.3 | 22 | 4.1 | 37 | na | 9.3 |
| OR Quart 4 | 0.99 | nd | 0.58 | 1.2 | 3.0 | 2.0 | 8.6 | >2.0 | 4.3 |
| p Value | 0.99 | nd | 0.47 | 0.64 | 0.34 | 0.20 | 0.044 | <0.56 | 0.069 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | | | | | | | |
|---|---|---|---|---|---|---|---|---|---|
| 95% CI of | 0.24 | nd | 0.13 | 0.51 | 0.31 | 0.70 | 1.1 | >0.18 | 0.89 |
| OR Quart4 | 4.1 | nd | 2.5 | 3.0 | 29 | 5.5 | 70 | na | 21 |

C-X-C motif chemokine 2

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.485 | 1.87 | 0.485 | 6.90 | 0.485 | 0.889 |
| Average | 8.64 | 16.6 | 8.64 | 23.6 | 8.64 | 5.37 |
| Stdev | 24.6 | 39.6 | 24.6 | 44.3 | 24.6 | 7.31 |
| p(t-test) | | 0.066 | | 1.4E-4 | | 0.48 |
| Min | 0.00804 | 0.0260 | 0.00804 | 0.0260 | 0.00804 | 0.0260 |
| Max | 266 | 217 | 266 | 217 | 266 | 20.9 |
| n (Samp) | 690 | 37 | 690 | 48 | 690 | 28 |
| n (Patient) | 279 | 37 | 279 | 48 | 279 | 28 |
| sCr only | | | | | | |
| Median | 0.687 | 11.6 | 0.687 | 15.2 | 0.687 | 3.34 |
| Average | 8.64 | 42.0 | 8.64 | 33.1 | 8.64 | 10.1 |
| Stdev | 24.0 | 69.5 | 24.0 | 58.6 | 24.0 | 12.5 |
| p(t-test) | | 6.6E-5 | | 4.4E-4 | | 0.83 |
| Min | 0.00804 | 0.0260 | 0.00804 | 0.0260 | 0.00804 | 0.0260 |
| Max | 266 | 217 | 266 | 217 | 266 | 31.3 |
| n (Samp) | 899 | 9 | 899 | 13 | 899 | 13 |
| n (Patient) | 335 | 9 | 335 | 13 | 335 | 13 |
| UO only | | | | | | |
| Median | 0.671 | 1.65 | 0.671 | 6.97 | 0.671 | 2.64 |
| Average | 9.13 | 16.4 | 9.13 | 25.2 | 9.13 | 5.99 |
| Stdev | 24.9 | 40.7 | 24.9 | 46.4 | 24.9 | 7.43 |
| p(t-test) | | 0.11 | | 1.7E-4 | | 0.53 |
| Min | 0.00804 | 0.0260 | 0.00804 | 0.0260 | 0.00804 | 0.0260 |
| Max | 266 | 217 | 266 | 217 | 266 | 20.9 |
| n (Samp) | 578 | 35 | 578 | 43 | 578 | 25 |
| n (Patient) | 205 | 35 | 205 | 43 | 205 | 25 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.58 | 0.72 | 0.55 | 0.68 | 0.73 | 0.68 | 0.52 | 0.58 | 0.55 |
| SE | 0.050 | 0.097 | 0.051 | 0.044 | 0.080 | 0.046 | 0.056 | 0.083 | 0.060 |
| p | 0.12 | 0.025 | 0.35 | 3.3E-5 | 0.0045 | 1.1E-4 | 0.73 | 0.34 | 0.38 |
| nCohort 1 | 690 | 899 | 578 | 690 | 899 | 578 | 690 | 899 | 578 |
| nCohort 2 | 37 | 9 | 35 | 48 | 13 | 43 | 28 | 13 | 25 |
| Cutoff 1 | 0.00804 | 1.86 | 0.00804 | 1.45 | 5.86 | 1.45 | 0.00804 | 0.00804 | 0.00804 |
| Sens 1 | 100% | 78% | 100% | 71% | 77% | 72% | 100% | 100% | 100% |
| Spec 1 | 0% | 57% | 0% | 57% | 73% | 54% | 0% | 0% | 0% |
| Cutoff 2 | 0.00804 | 0.00804 | 0.00804 | 0.121 | 0.00804 | 0.299 | 0.00804 | 0.00804 | 0.00804 |
| Sens 2 | 100% | 100% | 100% | 81% | 100% | 81% | 100% | 100% | 100% |
| Spec 2 | 0% | 0% | 0% | 45% | 0% | 46% | 0% | 0% | 0% |
| Cutoff 3 | 0.00804 | 0.00804 | 0.00804 | 0.00804 | 0.00804 | 0.00804 | 0.00804 | 0.00804 | 0.00804 |
| Sens 3 | 100% | 100% | 100% | 100% | 100% | 100% | 100% | 100% | 100% |
| Spec 3 | 0% | 0% | 0% | 0% | 0% | 0% | 0% | 0% | 0% |
| Cutoff 4 | 4.12 | 4.66 | 4.76 | 4.12 | 4.66 | 4.76 | 4.12 | 4.66 | 4.76 |
| Sens 4 | 38% | 67% | 34% | 56% | 77% | 56% | 36% | 46% | 40% |
| Spec 4 | 70% | 70% | 70% | 70% | 70% | 70% | 70% | 70% | 70% |
| Cutoff 5 | 8.05 | 8.68 | 8.50 | 8.05 | 8.68 | 8.50 | 8.05 | 8.68 | 8.50 |
| Sens 5 | 32% | 56% | 29% | 48% | 62% | 49% | 29% | 46% | 28% |
| Spec 5 | 80% | 80% | 80% | 80% | 80% | 80% | 80% | 80% | 80% |
| Cutoff 6 | 19.6 | 19.7 | 21.7 | 19.6 | 19.7 | 21.7 | 19.6 | 19.7 | 21.7 |
| Sens 6 | 16% | 44% | 14% | 31% | 46% | 30% | 4% | 23% | 0% |
| Spec 6 | 90% | 90% | 90% | 90% | 90% | 90% | 90% | 90% | 90% |
| OR Quart 2 | 0.16 | 0 | >15 | >14 | 0 | >12 | 0.16 | 0 | 0.24 |
| p Value | 0.016 | na | <0.0087 | <0.012 | na | <0.019 | 0.016 | na | 0.073 |
| 95% CI of | 0.035 | na | >2.0 | >1.8 | na | >1.5 | 0.034 | na | 0.050 |
| OR Quart2 | 0.71 | na | na | na | na | na | 0.71 | na | 1.1 |
| OR Quart 3 | 0.82 | 0.50 | >11 | >11 | 0.66 | >12 | 0.48 | 0.39 | 0.99 |
| p Value | 0.65 | 0.57 | <0.025 | <0.025 | 0.66 | <0.019 | 0.15 | 0.27 | 0.99 |
| 95% CI of | 0.34 | 0.045 | >1.4 | >1.3 | 0.11 | >1.5 | 0.18 | 0.076 | 0.36 |
| OR Quart3 | 1.9 | 5.5 | na | na | 4.0 | na | 1.3 | 2.1 | 2.7 |
| OR Quart 4 | 1.1 | 3.1 | >12 | >29 | 2.7 | >24 | 0.65 | 1.2 | 0.86 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | | | | | | | |
|---|---|---|---|---|---|---|---|---|---|
| p Value | 0.85 | 0.17 | <0.019 | <0.0011 | 0.14 | <0.0020 | 0.35 | 0.76 | 0.78 |
| 95% CI of | 0.48 | 0.61 | >1.5 | >3.9 | 0.71 | >3.2 | 0.26 | 0.36 | 0.30 |
| OR Quart4 | 2.4 | 15 | na | na | 10 | na | 1.6 | 4.0 | 2.4 |

Renin

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | Cohort 1 | Cohort 2 | Cohort 1 | Cohort 2 | Cohort 1 | Cohort 2 |
|---|---|---|---|---|---|---|
| Median | 343 | 669 | 343 | 1180 | 343 | 380 |
| Average | 808 | 1130 | 808 | 2210 | 808 | 1220 |
| Stdev | 1290 | 1140 | 1290 | 3740 | 1290 | 1780 |
| p(t-test) | | 0.25 | | 3.1E−5 | | 0.23 |
| Min | 1.00E−9 | 18.7 | 1.00E−9 | 1.00E−9 | 1.00E−9 | 1.00E−9 |
| Max | 9810 | 4050 | 9810 | 21100 | 9810 | 5550 |
| n (Samp) | 239 | 22 | 239 | 32 | 239 | 16 |
| n (Patient) | 157 | 22 | 157 | 32 | 157 | 16 | sCr only

| | Cohort 1 | Cohort 2 | Cohort 1 | Cohort 2 | Cohort 1 | Cohort 2 |
|---|---|---|---|---|---|---|
| Median | nd | nd | 394 | 1010 | 394 | 2150 |
| Average | nd | nd | 954 | 1350 | 954 | 2600 |
| Stdev | nd | nd | 1740 | 1410 | 1740 | 2150 |
| p(t-test) | nd | nd | | 0.58 | | 0.014 |
| Min | nd | nd | 1.00E−9 | 1.00E−9 | 1.00E−9 | 1.00E−9 |
| Max | nd | nd | 21100 | 3390 | 21100 | 5380 |
| n (Samp) | nd | nd | 305 | 6 | 305 | 7 |
| n (Patient) | nd | nd | 184 | 6 | 184 | 7 |

UO only

| | Cohort 1 | Cohort 2 | Cohort 1 | Cohort 2 | Cohort 1 | Cohort 2 |
|---|---|---|---|---|---|---|
| Median | 346 | 699 | 346 | 1180 | 346 | 435 |
| Average | 847 | 1160 | 847 | 2270 | 847 | 1220 |
| Stdev | 1350 | 1120 | 1350 | 3900 | 1350 | 1790 |
| p(t-test) | | 0.30 | | 1.3E−4 | | 0.31 |
| Min | 1.00E−9 | 18.7 | 1.00E−9 | 1.00E−9 | 1.00E−9 | 1.00E−9 |
| Max | 9810 | 4050 | 9810 | 21100 | 9810 | 5550 |
| n (Samp) | 207 | 22 | 207 | 29 | 207 | 15 |
| n (Patient) | 130 | 22 | 130 | 29 | 130 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.64 | nd | 0.64 | 0.70 | 0.58 | 0.71 | 0.52 | 0.68 | 0.54 |
| SE | 0.066 | nd | 0.066 | 0.054 | 0.12 | 0.057 | 0.075 | 0.11 | 0.079 |
| p | 0.033 | nd | 0.030 | 1.6E−4 | 0.50 | 2.3E−4 | 0.82 | 0.10 | 0.63 |
| nCohort 1 | 239 | nd | 207 | 239 | 305 | 207 | 239 | 305 | 207 |
| nCohort 2 | 22 | nd | 22 | 32 | 6 | 29 | 16 | 7 | 15 |
| Cutoff 1 | 337 | nd | 397 | 453 | 38.3 | 397 | 88.6 | 2070 | 134 |
| Sens 1 | 73% | nd | 73% | 72% | 83% | 72% | 75% | 71% | 73% |
| Spec 1 | 50% | nd | 55% | 57% | 16% | 55% | 24% | 88% | 28% |
| Cutoff 2 | 266 | nd | 266 | 380 | 38.3 | 310 | 69.5 | 0 | 118 |
| Sens 2 | 82% | nd | 82% | 81% | 83% | 83% | 81% | 100% | 80% |
| Spec 2 | 44% | nd | 43% | 52% | 16% | 48% | 23% | 0% | 25% |
| Cutoff 3 | 69.5 | nd | 69.5 | 96.1 | 0 | 125 | 0 | 0 | 69.5 |
| Sens 3 | 91% | nd | 91% | 91% | 100% | 93% | 100% | 100% | 93% |
| Spec 3 | 23% | nd | 21% | 25% | 0% | 26% | 0% | 0% | 21% |
| Cutoff 4 | 730 | nd | 743 | 730 | 879 | 743 | 730 | 879 | 743 |
| Sens 4 | 45% | nd | 45% | 66% | 50% | 66% | 38% | 71% | 33% |
| Spec 4 | 70% | nd | 70% | 70% | 70% | 70% | 70% | 70% | 70% |
| Cutoff 5 | 1280 | nd | 1410 | 1280 | 1590 | 1410 | 1280 | 1590 | 1410 |
| Sens 5 | 32% | nd | 32% | 47% | 33% | 45% | 38% | 71% | 27% |
| Spec 5 | 80% | nd | 80% | 80% | 80% | 80% | 80% | 80% | 80% |
| Cutoff 6 | 2070 | nd | 2140 | 2070 | 2390 | 2140 | 2070 | 2390 | 2140 |
| Sens 6 | 18% | nd | 18% | 38% | 33% | 38% | 19% | 43% | 13% |
| Spec 6 | 90% | nd | 90% | 90% | 90% | 90% | 90% | 90% | 90% |
| OR Quart 2 | 1.4 | nd | 1.0 | 0.73 | 0 | 1.4 | 0.57 | 0 | 1.3 |
| p Value | 0.70 | nd | 1.0 | 0.68 | na | 0.70 | 0.46 | na | 0.72 |
| 95% CI of | 0.29 | nd | 0.19 | 0.16 | na | 0.29 | 0.13 | na | 0.28 |
| OR Quart2 | 6.3 | nd | 5.2 | 3.4 | na | 6.3 | 2.5 | na | 6.3 |
| OR Quart 3 | 2.5 | nd | 2.9 | 2.1 | 0.49 | 3.4 | 0.37 | 0 | 1.0 |
| p Value | 0.20 | nd | 0.13 | 0.25 | 0.56 | 0.081 | 0.25 | na | 1.0 |
| 95% CI of | 0.62 | nd | 0.74 | 0.60 | 0.043 | 0.86 | 0.070 | na | 0.19 |
| OR Quart3 | 10 | nd | 12 | 7.3 | 5.5 | 13 | 2.0 | na | 5.2 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | | | | | | | |
|---|---|---|---|---|---|---|---|---|---|
| OR Quart 4 | 2.9 | nd | 2.9 | 5.2 | 1.5 | 5.3 | 1.2 | 2.6 | 1.7 |
| p Value | 0.14 | nd | 0.13 | 0.0047 | 0.66 | 0.013 | 0.77 | 0.26 | 0.48 |
| 95% CI of | 0.72 | nd | 0.72 | 1.7 | 0.24 | 1.4 | 0.35 | 0.49 | 0.39 |
| OR Quart4 | 11 | nd | 11 | 17 | 9.2 | 20 | 4.2 | 14 | 7.5 |

Cathepsin B

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | | | | | | |
|---|---|---|---|---|---|---|
| Median | 0.661 | 0.911 | 0.661 | 1.10 | 0.661 | 0.312 |
| Average | 2.94 | 1.16 | 2.94 | 5.27 | 2.94 | 1.34 |
| Stdev | 9.10 | 1.30 | 9.10 | 12.7 | 9.10 | 1.86 |
| p(t-test) | | 0.36 | | 0.19 | | 0.48 |
| Min | 1.00E−9 | 1.00E−9 | 1.00E−9 | 1.00E−9 | 1.00E−9 | 1.00E−9 |
| Max | 78.1 | 5.47 | 78.1 | 64.9 | 78.1 | 4.98 |
| n (Samp) | 256 | 22 | 256 | 32 | 256 | 16 |
| n (Patient) | 163 | 22 | 163 | 32 | 163 | 16 | sCr only

| | | | | | | |
|---|---|---|---|---|---|---|
| Median | nd | nd | 0.648 | 1.62 | 0.648 | 2.27 |
| Average | nd | nd | 2.81 | 6.92 | 2.81 | 5.45 |
| Stdev | nd | nd | 8.88 | 9.65 | 8.88 | 10.8 |
| p(t-test) | nd | nd | | 0.26 | | 0.44 |
| Min | nd | nd | 1.00E−9 | 0.593 | 1.00E−9 | 0.0682 |
| Max | nd | nd | 78.1 | 24.2 | 78.1 | 29.7 |
| n (Samp) | nd | nd | 322 | 6 | 322 | 7 |
| n (Patient) | nd | nd | 190 | 6 | 190 | 7 |

UO only

| | | | | | | |
|---|---|---|---|---|---|---|
| Median | 0.768 | 0.911 | 0.768 | 1.20 | 0.768 | 0.605 |
| Average | 3.26 | 1.14 | 3.26 | 5.03 | 3.26 | 2.90 |
| Stdev | 9.69 | 1.27 | 9.69 | 12.8 | 9.69 | 6.17 |
| p(t-test) | | 0.31 | | 0.38 | | 0.89 |
| Min | 1.00E−9 | 1.00E−9 | 1.00E−9 | 1.00E−9 | 1.00E−9 | 1.00E−9 |
| Max | 78.1 | 5.29 | 78.1 | 64.9 | 78.1 | 24.2 |
| n (Samp) | 222 | 22 | 222 | 29 | 222 | 15 |
| n (Patient) | 135 | 22 | 135 | 29 | 135 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.50 | nd | 0.47 | 0.62 | 0.73 | 0.59 | 0.42 | 0.60 | 0.44 |
| SE | 0.064 | nd | 0.066 | 0.056 | 0.12 | 0.059 | 0.077 | 0.11 | 0.079 |
| p | 0.96 | nd | 0.62 | 0.032 | 0.056 | 0.14 | 0.30 | 0.37 | 0.46 |
| nCohort 1 | 256 | nd | 222 | 256 | 322 | 222 | 256 | 322 | 222 |
| nCohort 2 | 22 | nd | 22 | 32 | 6 | 29 | 16 | 7 | 15 |
| Cutoff 1 | 0.296 | nd | 0.296 | 0.572 | 0.797 | 0.522 | 0.0513 | 0.319 | 0.158 |
| Sens 1 | 73% | nd | 73% | 72% | 83% | 72% | 75% | 71% | 73% |
| Spec 1 | 32% | nd | 29% | 48% | 55% | 39% | 13% | 34% | 18% |
| Cutoff 2 | 0.140 | nd | 0.140 | 0.463 | 0.797 | 0.460 | 0 | 0.309 | 0 |
| Sens 2 | 82% | nd | 82% | 81% | 83% | 83% | 100% | 86% | 100% |
| Spec 2 | 19% | nd | 17% | 40% | 55% | 35% | 0% | 33% | 0% |
| Cutoff 3 | 1.00E−9 | nd | 1.00E−9 | 0.290 | 0.572 | 0.236 | 0 | 0.0513 | 0 |
| Sens 3 | 91% | nd | 91% | 91% | 100% | 93% | 100% | 100% | 100% |
| Spec 3 | 12% | nd | 10% | 31% | 48% | 23% | 0% | 14% | 0% |
| Cutoff 4 | 1.46 | nd | 1.64 | 1.46 | 1.41 | 1.64 | 1.46 | 1.41 | 1.64 |
| Sens 4 | 27% | nd | 23% | 38% | 50% | 38% | 31% | 57% | 33% |
| Spec 4 | 70% | nd | 70% | 70% | 70% | 70% | 70% | 70% | 70% |
| Cutoff 5 | 2.37 | nd | 2.74 | 2.37 | 2.37 | 2.74 | 2.37 | 2.37 | 2.74 |
| Sens 5 | 14% | nd | 9% | 25% | 33% | 28% | 25% | 43% | 27% |
| Spec 5 | 80% | nd | 80% | 80% | 80% | 80% | 80% | 80% | 80% |
| Cutoff 6 | 5.61 | nd | 6.20 | 5.61 | 4.86 | 6.20 | 5.61 | 4.86 | 6.20 |
| Sens 6 | 0% | nd | 0% | 16% | 33% | 14% | 0% | 14% | 7% |
| Spec 6 | 90% | nd | 90% | 90% | 90% | 90% | 90% | 90% | 90% |
| OR Quart 2 | 1.7 | nd | 3.3 | 2.9 | >1.0 | 2.9 | 0.19 | 2.0 | 0 |
| p Value | 0.37 | nd | 0.082 | 0.13 | <0.99 | 0.13 | 0.13 | 0.57 | na |
| 95% CI of | 0.53 | nd | 0.86 | 0.73 | >0.062 | 0.72 | 0.021 | 0.18 | na |
| OR Quart2 | 5.5 | nd | 13 | 11 | na | 11 | 1.7 | 23 | na |
| OR Quart 3 | 0.79 | nd | 1.7 | 3.7 | >2.0 | 2.9 | 0.79 | 0 | 0.80 |
| p Value | 0.73 | nd | 0.47 | 0.054 | <0.56 | 0.13 | 0.73 | na | 0.75 |
| 95% CI of | 0.20 | nd | 0.39 | 0.98 | >0.18 | 0.72 | 0.20 | na | 0.20 |

TABLE 2-continued

Comparison of marker levels in urine samples collected from Cohort 1 (patients that
did not progress beyond RIFLE stage 0 or R) and in urine samples collected from subjects
at 0, 24 hours, and 48 hours prior to reaching stage I or F in Cohort 2.

| | | | | | | | | | |
|---|---|---|---|---|---|---|---|---|---|
| OR Quart3 | 3.1 | nd | 7.6 | 14 | na | 11 | 3.1 | na | 3.1 |
| OR Quart 4 | 1.0 | nd | 1.7 | 4.1 | >3.1 | 3.7 | 1.2 | 4.1 | 1.2 |
| p Value | 0.98 | nd | 0.47 | 0.035 | <0.33 | 0.056 | 0.75 | 0.21 | 0.73 |
| 95% CI of | 0.28 | nd | 0.39 | 1.1 | >0.32 | 0.97 | 0.35 | 0.45 | 0.36 |
| OR Quart4 | 3.7 | nd | 7.6 | 16 | na | 14 | 4.2 | 38 | 4.3 |

Dipeptidyl peptidase IV

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | | | | | | |
|---|---|---|---|---|---|---|
| Median | 157 | 473 | 157 | 662 | 157 | 455 |
| Average | 4080 | 1160 | 4080 | 1750 | 4080 | 758 |
| Stdev | 47500 | 1640 | 47500 | 3170 | 47500 | 826 |
| p(t-test) | | 0.81 | | 0.83 | | 0.82 |
| Min | 0.200 | 7.95 | 0.200 | 10.1 | 0.200 | 17.0 |
| Max | 677000 | 5420 | 677000 | 12500 | 677000 | 2280 |
| n (Samp) | 203 | 16 | 203 | 19 | 203 | 11 |
| n (Patient) | 135 | 16 | 203 | 19 | 135 | 11 |

UO only

| | | | | | | |
|---|---|---|---|---|---|---|
| Median | 151 | 603 | 151 | 639 | 151 | 556 |
| Average | 619 | 1230 | 619 | 1480 | 619 | 836 |
| Stdev | 1350 | 1630 | 1350 | 2970 | 1350 | 777 |
| p(t-test) | | 0.091 | | 0.028 | | 0.60 |
| Min | 0.200 | 7.95 | 0.200 | 10.1 | 0.200 | 17.0 |
| Max | 11000 | 5420 | 11000 | 12500 | 11000 | 2280 |
| n (Samp) | 174 | 16 | 174 | 18 | 174 | 11 |
| n (Patient) | 114 | 16 | 114 | 18 | 114 | 11 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.61 | nd | 0.63 | 0.66 | nd | 0.65 | 0.61 | nd | 0.68 |
| SE | 0.077 | nd | 0.078 | 0.071 | nd | 0.073 | 0.093 | nd | 0.092 |
| p | 0.14 | nd | 0.086 | 0.028 | nd | 0.039 | 0.24 | nd | 0.055 |
| nCohort 1 | 203 | nd | 174 | 203 | nd | 174 | 203 | nd | 174 |
| nCohort 2 | 16 | nd | 16 | 19 | nd | 18 | 11 | nd | 11 |
| Cutoff 1 | 63.4 | nd | 52.3 | 294 | nd | 294 | 161 | nd | 407 |
| Sens 1 | 75% | nd | 75% | 74% | nd | 72% | 73% | nd | 73% |
| Spec 1 | 33% | nd | 32% | 60% | nd | 61% | 51% | nd | 65% |
| Cutoff 2 | 52.3 | nd | 31.7 | 48.0 | nd | 48.0 | 52.3 | nd | 161 |
| Sens 2 | 81% | nd | 81% | 84% | nd | 83% | 82% | nd | 82% |
| Spec 2 | 31% | nd | 25% | 29% | nd | 29% | 31% | nd | 52% |
| Cutoff 3 | 18.2 | nd | 18.2 | 18.2 | nd | 18.2 | 39.0 | nd | 39.0 |
| Sens 3 | 94% | nd | 94% | 95% | nd | 94% | 91% | nd | 91% |
| Spec 3 | 19% | nd | 20% | 19% | nd | 20% | 27% | nd | 27% |
| Cutoff 4 | 560 | nd | 529 | 560 | nd | 529 | 560 | nd | 529 |
| Sens 4 | 44% | nd | 50% | 58% | nd | 61% | 36% | nd | 55% |
| Spec 4 | 70% | nd | 70% | 70% | nd | 70% | 70% | nd | 70% |
| Cutoff 5 | 1010 | nd | 889 | 1010 | nd | 889 | 1010 | nd | 889 |
| Sens 5 | 25% | nd | 31% | 26% | nd | 33% | 36% | nd | 36% |
| Spec 5 | 80% | nd | 80% | 80% | nd | 80% | 80% | nd | 80% |
| Cutoff 6 | 1560 | nd | 1530 | 1560 | nd | 1530 | 1560 | nd | 1530 |
| Sens 6 | 25% | nd | 31% | 16% | nd | 11% | 18% | nd | 18% |
| Spec 6 | 90% | nd | 90% | 90% | nd | 90% | 90% | nd | 90% |
| OR Quart 2 | 0.64 | nd | 0.64 | 0.64 | nd | 0.65 | 3.1 | nd | 1.0 |
| p Value | 0.63 | nd | 0.63 | 0.63 | nd | 0.65 | 0.34 | nd | 1.0 |
| 95% CI of | 0.10 | nd | 0.10 | 0.10 | nd | 0.10 | 0.31 | nd | 0.061 |
| OR Quart2 | 4.0 | nd | 4.0 | 4.0 | nd | 4.1 | 30 | nd | 16 |
| OR Quart 3 | 2.1 | nd | 1.4 | 2.5 | nd | 1.7 | 3.1 | nd | 4.3 |
| p Value | 0.32 | nd | 0.70 | 0.20 | nd | 0.46 | 0.33 | nd | 0.20 |
| 95% CI of | 0.49 | nd | 0.29 | 0.62 | nd | 0.39 | 0.31 | nd | 0.46 |
| OR Quart3 | 8.8 | nd | 6.5 | 10 | nd | 7.7 | 31 | nd | 40 |
| OR Quart 4 | 1.7 | nd | 2.5 | 2.5 | nd | 3.0 | 4.2 | nd | 5.4 |
| p Value | 0.48 | nd | 0.20 | 0.21 | nd | 0.12 | 0.21 | nd | 0.13 |
| 95% CI of | 0.39 | nd | 0.61 | 0.61 | nd | 0.74 | 0.45 | nd | 0.60 |
| OR Quart4 | 7.5 | nd | 10 | 10 | nd | 12 | 39 | nd | 48 |

TABLE 3

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| | Beta-2-microglobulin | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| | sCr or UO | | | | | |
| Median | 4.78 | 2.99 | 4.78 | 3.49 | 4.78 | 2.99 |
| Average | 3.59 | 2.92 | 3.59 | 3.09 | 3.59 | 2.83 |
| Stdev | 2.43 | 2.66 | 2.43 | 2.64 | 2.43 | 2.50 |
| p(t-test) | | 0.31 | | 0.46 | | 0.40 |
| Min | 0.00270 | 0.00133 | 0.00270 | 0.00133 | 0.00270 | 0.0324 |
| Max | 6.10 | 5.80 | 6.10 | 5.80 | 6.10 | 5.80 |
| n (Samp) | 103 | 16 | 103 | 15 | 103 | 8 |
| n (Patient) | 103 | 16 | 103 | 15 | 103 | 8 |
| | sCr only | | | | | |
| Median | 4.50 | 5.24 | 4.50 | 5.16 | nd | nd |
| Average | 3.52 | 3.82 | 3.52 | 3.80 | nd | nd |
| Stdev | 2.47 | 2.57 | 2.47 | 2.55 | nd | nd |
| p(t-test) | | 0.74 | | 0.75 | nd | nd |
| Min | 0.00270 | 0.00133 | 0.00270 | 0.00133 | nd | nd |
| Max | 6.10 | 5.80 | 6.10 | 5.80 | nd | nd |
| n (Samp) | 170 | 8 | 170 | 8 | nd | nd |
| n (Patient) | 170 | 8 | 170 | 8 | nd | nd |
| | UO only | | | | | |
| Median | 4.20 | 0.348 | 4.20 | 0.480 | 4.20 | 1.83 |
| Average | 3.52 | 2.21 | 3.52 | 2.43 | 3.52 | 2.57 |
| Stdev | 2.42 | 2.68 | 2.42 | 2.74 | 2.42 | 2.82 |
| p(t-test) | | 0.11 | | 0.21 | | 0.36 |
| Min | 0.00270 | 0.0324 | 0.00270 | 0.0324 | 0.00270 | 0.0324 |
| Max | 6.10 | 5.80 | 6.10 | 5.80 | 6.10 | 5.80 |
| n (Samp) | 87 | 10 | 87 | 9 | 87 | 6 |
| n (Patient) | 87 | 10 | 87 | 9 | 87 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.41 | 0.49 | 0.32 | 0.41 | 0.47 | 0.35 | 0.38 | nd | 0.36 |
| SE | 0.080 | 0.11 | 0.098 | 0.082 | 0.11 | 0.10 | 0.11 | nd | 0.13 |
| p | 0.24 | 0.95 | 0.073 | 0.29 | 0.81 | 0.14 | 0.28 | nd | 0.25 |
| nCohort 1 | 103 | 170 | 87 | 103 | 170 | 87 | 103 | nd | 87 |
| nCohort 2 | 16 | 8 | 10 | 15 | 8 | 9 | 8 | nd | 6 |
| Cutoff 1 | 0.170 | 2.39 | 0.170 | 0.170 | 2.39 | 0.152 | 0.170 | nd | 0.0851 |
| Sens 1 | 75% | 75% | 70% | 73% | 75% | 78% | 75% | nd | 83% |
| Spec 1 | 13% | 38% | 10% | 13% | 38% | 9% | 13% | nd | 9% |
| Cutoff 2 | 0.152 | 0.152 | 0.152 | 0.152 | 0.152 | 0.0851 | 0.0851 | nd | 0.0851 |
| Sens 2 | 81% | 88% | 80% | 80% | 88% | 89% | 88% | nd | 83% |
| Spec 2 | 12% | 13% | 9% | 12% | 13% | 9% | 12% | nd | 9% |
| Cutoff 3 | 0.0319 | 0 | 0.0851 | 0.0319 | 0 | 0.0273 | 0.0319 | nd | 0.0273 |
| Sens 3 | 94% | 100% | 90% | 93% | 100% | 100% | 100% | nd | 100% |
| Spec 3 | 6% | 0% | 9% | 6% | 0% | 5% | 6% | nd | 5% |
| Cutoff 4 | 5.80 | 5.80 | 5.80 | 5.80 | 5.80 | 5.80 | 5.80 | nd | 5.80 |
| Sens 4 | 0% | 0% | 0% | 0% | 0% | 0% | 0% | nd | 0% |
| Spec 4 | 89% | 88% | 86% | 89% | 88% | 86% | 89% | nd | 86% |
| Cutoff 5 | 5.80 | 5.80 | 5.80 | 5.80 | 5.80 | 5.80 | 5.80 | nd | 5.80 |
| Sens 5 | 0% | 0% | 0% | 0% | 0% | 0% | 0% | nd | 0% |
| Spec 5 | 89% | 88% | 86% | 89% | 88% | 86% | 89% | nd | 86% |
| Cutoff 6 | 5.84 | 6.10 | 6.10 | 5.84 | 6.10 | 6.10 | 5.84 | nd | 6.10 |
| Sens 6 | 0% | 0% | 0% | 0% | 0% | 0% | 0% | nd | 0% |
| Spec 6 | 90% | 100% | 100% | 90% | 100% | 100% | 90% | nd | 100% |
| OR Quart 2 | >9.1 | >5.8 | >3.6 | >9.5 | >5.8 | >3.4 | >3.4 | nd | 1.0 |
| p Value | <0.045 | <0.12 | <0.29 | <0.041 | <0.12 | <0.30 | <0.31 | nd | 0.98 |
| 95% CI of | >1.0 | >0.65 | >0.35 | >1.1 | >0.65 | >0.33 | >0.33 | nd | 0.062 |
| OR Quart2 | na | na | na | na | na | na | na | nd | 18 |
| OR Quart 3 | >2.1 | >1.0 | >1.1 | >2.1 | >1.0 | >1.0 | >2.2 | nd | 1.0 |
| p Value | <0.54 | <0.99 | <0.95 | <0.54 | <0.99 | <0.98 | <0.54 | nd | 0.98 |
| 95% CI of | >0.18 | >0.062 | >0.064 | >0.18 | >0.062 | >0.062 | >0.18 | nd | 0.062 |
| OR Quart3 | na | na | na | na | na | na | na | nd | 18 |
| OR Quart 4 | >9.5 | >2.1 | >8.3 | >7.8 | >2.1 | >6.3 | >3.5 | nd | 3.4 |
| p Value | <0.041 | <0.54 | <0.059 | <0.065 | <0.54 | <0.11 | <0.29 | nd | 0.30 |

TABLE 3-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| 95% CI of | >1.1 | >0.19 | >0.92 | >0.88 | >0.19 | >0.68 | >0.34 | nd | 0.33 |
|---|---|---|---|---|---|---|---|---|---|
| OR Quart4 | na | na | na | na | na | na | na | nd | 36 |

C-X-C motif chemokine 2

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | Cohort 1 | Cohort 2 | Cohort 1 | Cohort 2 | Cohort 1 | Cohort 2 |
|---|---|---|---|---|---|---|
| Median | 1.04 | 28.7 | 1.04 | 27.8 | 1.04 | 3.34 |
| Average | 9.16 | 42.4 | 9.16 | 37.7 | 9.16 | 12.4 |
| Stdev | 30.2 | 57.0 | 30.2 | 56.5 | 30.2 | 14.7 |
| p(t-test) | | 2.7E−5 | | 2.9E−4 | | 0.73 |
| Min | 0.00804 | 0.0260 | 0.00804 | 0.0260 | 0.00804 | 0.0260 |
| Max | 266 | 217 | 266 | 217 | 266 | 36.2 |
| n (Samp) | 190 | 21 | 190 | 21 | 190 | 11 |
| n (Patient) | 190 | 21 | 190 | 21 | 190 | 11 | sCr only

| | Cohort 1 | Cohort 2 | Cohort 1 | Cohort 2 | Cohort 1 | Cohort 2 |
|---|---|---|---|---|---|---|
| Median | 1.90 | 27.8 | 1.90 | 27.8 | 1.90 | 6.02 |
| Average | 13.1 | 38.9 | 13.1 | 38.9 | 13.1 | 11.5 |
| Stdev | 33.8 | 63.2 | 33.8 | 63.2 | 33.8 | 13.5 |
| p(t-test) | | 0.017 | | 0.017 | | 0.91 |
| Min | 0.00804 | 0.0260 | 0.00804 | 0.0260 | 0.00804 | 0.135 |
| Max | 266 | 217 | 266 | 217 | 266 | 31.3 |
| n (Samp) | 295 | 11 | 295 | 11 | 295 | 6 |
| n (Patient) | 295 | 11 | 295 | 11 | 295 | 6 |

UO only

| | Cohort 1 | Cohort 2 | Cohort 1 | Cohort 2 | Cohort 1 | Cohort 2 |
|---|---|---|---|---|---|---|
| Median | 1.60 | 35.3 | 1.60 | 29.0 | 1.60 | 3.34 |
| Average | 9.22 | 53.2 | 9.22 | 46.6 | 9.22 | 14.0 |
| Stdev | 29.8 | 64.3 | 29.8 | 64.7 | 29.8 | 15.7 |
| p(t-test) | | 6.7E−6 | | 1.2E−4 | | 0.64 |
| Min | 0.00804 | 0.534 | 0.00804 | 0.534 | 0.00804 | 0.0260 |
| Max | 266 | 217 | 266 | 217 | 266 | 36.2 |
| n (Samp) | 134 | 15 | 134 | 15 | 134 | 9 |
| n (Patient) | 134 | 15 | 134 | 15 | 134 | 9 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.79 | 0.70 | 0.81 | 0.79 | 0.70 | 0.80 | 0.68 | 0.65 | 0.67 |
| SE | 0.061 | 0.089 | 0.070 | 0.061 | 0.089 | 0.070 | 0.091 | 0.12 | 0.10 |
| p | 1.9E−6 | 0.022 | 1.0E−5 | 2.7E−6 | 0.023 | 1.5E−5 | 0.042 | 0.23 | 0.089 |
| nCohort 1 | 190 | 295 | 134 | 190 | 295 | 134 | 190 | 295 | 134 |
| nCohort 2 | 21 | 11 | 15 | 21 | 11 | 15 | 11 | 6 | 9 |
| Cutoff 1 | 3.33 | 1.95 | 3.33 | 3.33 | 1.95 | 3.33 | 1.52 | 0.570 | 1.52 |
| Sens 1 | 71% | 73% | 73% | 71% | 73% | 73% | 73% | 83% | 78% |
| Spec 1 | 65% | 51% | 60% | 65% | 51% | 60% | 54% | 41% | 49% |
| Cutoff 2 | 1.52 | 0.570 | 1.95 | 1.52 | 0.570 | 1.95 | 0.541 | 0.570 | 0.544 |
| Sens 2 | 81% | 82% | 80% | 81% | 82% | 80% | 82% | 83% | 89% |
| Spec 2 | 54% | 41% | 56% | 54% | 41% | 56% | 48% | 41% | 45% |
| Cutoff 3 | 0.371 | 0.134 | 0.544 | 0.371 | 0.134 | 0.544 | 0.134 | 0.134 | 0.00804 |
| Sens 3 | 90% | 91% | 93% | 90% | 91% | 93% | 91% | 100% | 100% |
| Spec 3 | 48% | 37% | 45% | 48% | 37% | 45% | 45% | 37% | 1% |
| Cutoff 4 | 4.12 | 6.43 | 4.69 | 4.12 | 6.43 | 4.69 | 4.12 | 6.43 | 4.69 |
| Sens 4 | 67% | 64% | 67% | 67% | 55% | 67% | 45% | 50% | 44% |
| Spec 4 | 70% | 70% | 70% | 70% | 70% | 70% | 70% | 70% | 70% |
| Cutoff 5 | 6.66 | 11.6 | 8.08 | 6.66 | 11.6 | 8.08 | 6.66 | 11.6 | 8.08 |
| Sens 5 | 62% | 55% | 67% | 62% | 55% | 67% | 45% | 33% | 44% |
| Spec 5 | 80% | 80% | 81% | 80% | 80% | 81% | 80% | 80% | 81% |
| Cutoff 6 | 14.8 | 28.5 | 14.8 | 14.8 | 28.5 | 14.8 | 14.8 | 28.5 | 14.8 |
| Sens 6 | 57% | 45% | 60% | 57% | 45% | 60% | 36% | 17% | 44% |
| Spec 6 | 90% | 90% | 90% | 90% | 90% | 90% | 90% | 90% | 90% |
| OR Quart 2 | >4.2 | 2.0 | >3.3 | >4.2 | 2.0 | >3.3 | >3.2 | >2.1 | >3.2 |
| p Value | <0.20 | 0.57 | <0.32 | <0.20 | 0.57 | <0.32 | <0.32 | <0.56 | <0.33 |
| 95% CI of | >0.46 | 0.18 | >0.32 | >0.46 | 0.18 | >0.32 | >0.32 | >0.18 | >0.31 |
| OR Quart2 | na | 23 | na | na | 23 | na | na | na | na |
| OR Quart 3 | >4.2 | 2.0 | >2.1 | >4.2 | 2.0 | >2.1 | >3.2 | >1.0 | >2.1 |
| p Value | <0.20 | 0.57 | <0.55 | <0.20 | 0.57 | <0.55 | <0.32 | <0.99 | <0.56 |
| 95% CI of | >0.46 | 0.18 | >0.18 | >0.46 | 0.18 | >0.18 | >0.32 | >0.062 | >0.18 |
| OR Quart3 | na | 23 | na | na | 23 | na | na | na | na |
| OR Quart 4 | >17 | 6.3 | >13 | >17 | 6.3 | >13 | >5.4 | >3.1 | >4.4 |

TABLE 3-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| | | | | | | | | | |
|---|---|---|---|---|---|---|---|---|---|
| p Value | <0.0076 | 0.091 | <0.017 | <0.0076 | 0.091 | <0.017 | <0.13 | <0.33 | <0.20 |
| 95% CI of | >2.1 | 0.74 | >1.6 | >2.1 | 0.74 | >1.6 | >0.61 | >0.31 | >0.46 |
| OR Quart4 | na | 54 | na | na | 54 | na | na | na | na |

Renin

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | Cohort 1 | Cohort 2 | Cohort 1 | Cohort 2 | Cohort 1 | Cohort 2 |
|---|---|---|---|---|---|---|
| Median | 382 | 3580 | 382 | 3580 | 382 | 2150 |
| Average | 828 | 5520 | 828 | 4430 | 828 | 2820 |
| Stdev | 1360 | 6880 | 1360 | 5560 | 1360 | 1670 |
| p(t-test) | | 2.4E-8 | | 4.5E-7 | | 3.6E-4 |
| Min | 1.00E-9 | 99.0 | 1.00E-9 | 99.0 | 1.00E-9 | 326 |
| Max | 9810 | 21100 | 9810 | 21100 | 9810 | 5370 |
| n (Samp) | 98 | 12 | 98 | 12 | 98 | 7 |
| n (Patient) | 98 | 12 | 98 | 12 | 98 | 7 | sCr only

| | Cohort 1 | Cohort 2 | Cohort 1 | Cohort 2 | Cohort 1 | Cohort 2 |
|---|---|---|---|---|---|---|
| Median | 494 | 3030 | 494 | 3030 | nd | nd |
| Average | 1230 | 5100 | 1230 | 5100 | nd | nd |
| Stdev | 2230 | 6800 | 2230 | 6800 | nd | nd |
| p(t-test) | | 2.6E-4 | | 2.6E-4 | nd | nd |
| Min | 1.00E-9 | 99.0 | 1.00E-9 | 99.0 | nd | nd |
| Max | 21100 | 18400 | 21100 | 18400 | nd | nd |
| n (Samp) | 159 | 6 | 159 | 6 | nd | nd |
| n (Patient) | 159 | 6 | 159 | 6 | nd | nd |

UO only

| | Cohort 1 | Cohort 2 | Cohort 1 | Cohort 2 | Cohort 1 | Cohort 2 |
|---|---|---|---|---|---|---|
| Median | 371 | 4150 | 371 | 4150 | 371 | 2930 |
| Average | 873 | 7420 | 873 | 5790 | 873 | 2930 |
| Stdev | 1480 | 7810 | 1480 | 6420 | 1480 | 1810 |
| p(t-test) | | 1.5E-9 | | 1.1E-7 | | 0.0016 |
| Min | 1.00E-9 | 326 | 1.00E-9 | 326 | 1.00E-9 | 326 |
| Max | 9810 | 21100 | 9810 | 21100 | 9810 | 5370 |
| n (Samp) | 82 | 8 | 82 | 8 | 82 | 6 |
| n (Patient) | 82 | 8 | 82 | 8 | 82 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.84 | 0.75 | 0.90 | 0.84 | 0.75 | 0.90 | 0.87 | nd | 0.85 |
| SE | 0.073 | 0.12 | 0.074 | 0.074 | 0.12 | 0.075 | 0.088 | nd | 0.10 |
| p | 3.6E-6 | 0.030 | 7.6E-8 | 4.4E-6 | 0.030 | 1.4E-7 | 2.9E-5 | nd | 5.0E-4 |
| nCohort 1 | 98 | 159 | 82 | 98 | 159 | 82 | 98 | nd | 82 |
| nCohort 2 | 12 | 6 | 8 | 12 | 6 | 8 | 7 | nd | 6 |
| Cutoff 1 | 2070 | 606 | 3280 | 2070 | 606 | 3280 | 2070 | nd | 1840 |
| Sens 1 | 75% | 83% | 75% | 75% | 83% | 75% | 71% | nd | 83% |
| Spec 1 | 91% | 58% | 95% | 91% | 58% | 95% | 91% | nd | 87% |
| Cutoff 2 | 606 | 606 | 2070 | 606 | 606 | 2070 | 1990 | nd | 1840 |
| Sens 2 | 83% | 83% | 88% | 83% | 83% | 88% | 86% | nd | 83% |
| Spec 2 | 68% | 58% | 89% | 68% | 58% | 89% | 89% | nd | 87% |
| Cutoff 3 | 310 | 88.6 | 310 | 310 | 88.6 | 310 | 310 | nd | 310 |
| Sens 3 | 92% | 100% | 100% | 92% | 100% | 100% | 100% | nd | 100% |
| Spec 3 | 45% | 18% | 46% | 45% | 18% | 46% | 45% | nd | 46% |
| Cutoff 4 | 730 | 1150 | 695 | 730 | 1150 | 695 | 730 | nd | 695 |
| Sens 4 | 75% | 67% | 88% | 75% | 67% | 88% | 86% | nd | 83% |
| Spec 4 | 70% | 70% | 71% | 70% | 70% | 71% | 70% | nd | 71% |
| Cutoff 5 | 1280 | 1840 | 1280 | 1280 | 1840 | 1280 | 1280 | nd | 1280 |
| Sens 5 | 75% | 67% | 88% | 75% | 67% | 88% | 86% | nd | 83% |
| Spec 5 | 81% | 81% | 80% | 81% | 81% | 80% | 81% | nd | 80% |
| Cutoff 6 | 2070 | 3280 | 2140 | 2070 | 3280 | 2140 | 2070 | nd | 2140 |
| Sens 6 | 75% | 50% | 75% | 75% | 50% | 75% | 71% | nd | 50% |
| Spec 6 | 91% | 91% | 90% | 91% | 91% | 90% | 91% | nd | 90% |
| OR Quart 2 | 0.96 | 0 | >1.0 | 0.96 | 0 | >1.0 | >1.0 | nd | >1.0 |
| p Value | 0.98 | na | <1.0 | 0.98 | na | <1.0 | <0.98 | nd | <0.97 |
| 95% CI of | 0.057 | na | >0.059 | 0.057 | na | >0.059 | >0.062 | nd | >0.061 |
| OR Quart2 | 16 | na | na | 16 | na | na | na | nd | na |
| OR Quart 3 | 1.0 | 1.0 | >0 | 1.0 | 1.0 | >0 | >0 | nd | >0 |
| p Value | 1.0 | 1.0 | <na | 1.0 | 1.0 | <na | <na | nd | <na |
| 95% CI of | 0.059 | 0.060 | >na | 0.059 | 0.060 | >na | >na | nd | >na |
| OR Quart3 | 17 | 17 | na | 17 | 17 | na | na | nd | na |

TABLE 3-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| | | | | | | | | | |
|---|---|---|---|---|---|---|---|---|---|
| OR Quart 4 | 12 | 4.2 | >9.6 | 12 | 4.2 | >9.6 | >7.4 | nd | >6.5 |
| p Value | 0.022 | 0.21 | <0.043 | 0.022 | 0.21 | <0.043 | <0.073 | nd | <0.10 |
| 95% CI of | 1.4 | 0.45 | >1.1 | 1.4 | 0.45 | >1.1 | >0.83 | nd | >0.69 |
| OR Quart4 | 110 | 39 | na | 110 | 39 | na | na | nd | na |

Cathepsin B

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | Cohort 1 | Cohort 2 | Cohort 1 | Cohort 2 | Cohort 1 | Cohort 2 |
|---|---|---|---|---|---|---|
| Median | 0.556 | 4.74 | 0.556 | 4.74 | 0.556 | 2.27 |
| Average | 2.13 | 12.7 | 2.13 | 12.7 | 2.13 | 2.62 |
| Stdev | 7.41 | 19.1 | 7.41 | 19.1 | 7.41 | 2.21 |
| p(t-test) | | 2.7E−4 | | 2.7E−4 | | 0.86 |
| Min | 1.00E−9 | 0.310 | 1.00E−9 | 0.310 | 1.00E−9 | 0.310 |
| Max | 72.4 | 64.9 | 72.4 | 64.9 | 72.4 | 6.19 |
| n (Samp) | 102 | 12 | 102 | 12 | 102 | 7 |
| n (Patient) | 102 | 12 | 102 | 12 | 102 | 7 | sCr only

| | Cohort 1 | Cohort 2 | Cohort 1 | Cohort 2 | Cohort 1 | Cohort 2 |
|---|---|---|---|---|---|---|
| Median | 0.897 | 9.47 | 0.897 | 9.47 | nd | nd |
| Average | 3.16 | 12.6 | 3.16 | 12.6 | nd | nd |
| Stdev | 9.92 | 12.0 | 9.92 | 12.0 | nd | nd |
| p(t-test) | | 0.025 | | 0.025 | nd | nd |
| Min | 1.00E−9 | 0.405 | 1.00E−9 | 0.405 | nd | nd |
| Max | 78.1 | 29.7 | 78.1 | 29.7 | nd | nd |
| n (Samp) | 162 | 6 | 162 | 6 | nd | nd |
| n (Patient) | 162 | 6 | 162 | 6 | nd | nd |

UO only

| | Cohort 1 | Cohort 2 | Cohort 1 | Cohort 2 | Cohort 1 | Cohort 2 |
|---|---|---|---|---|---|---|
| Median | 0.677 | 4.74 | 0.677 | 4.74 | 0.677 | 2.13 |
| Average | 2.26 | 14.2 | 2.26 | 14.2 | 2.26 | 2.68 |
| Stdev | 7.97 | 22.7 | 7.97 | 22.7 | 7.97 | 2.42 |
| p(t-test) | | 0.0015 | | 0.0015 | | 0.90 |
| Min | 1.00E−9 | 0.310 | 1.00E−9 | 0.310 | 1.00E−9 | 0.310 |
| Max | 72.4 | 64.9 | 72.4 | 64.9 | 72.4 | 6.19 |
| n (Samp) | 87 | 8 | 87 | 8 | 87 | 6 |
| n (Patient) | 87 | 8 | 87 | 8 | 87 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.79 | 0.82 | 0.77 | 0.79 | 0.82 | 0.77 | 0.71 | nd | 0.69 |
| SE | 0.081 | 0.11 | 0.10 | 0.081 | 0.11 | 0.10 | 0.11 | nd | 0.12 |
| p | 4.2E−4 | 0.0030 | 0.0064 | 4.2E−4 | 0.0030 | 0.0064 | 0.059 | nd | 0.13 |
| nCohort 1 | 102 | 162 | 87 | 102 | 162 | 87 | 102 | nd | 87 |
| nCohort 2 | 12 | 6 | 8 | 12 | 6 | 8 | 7 | nd | 6 |
| Cutoff 1 | 0.949 | 2.16 | 0.949 | 0.949 | 2.16 | 0.949 | 0.888 | nd | 0.604 |
| Sens 1 | 75% | 83% | 75% | 75% | 83% | 75% | 71% | nd | 83% |
| Spec 1 | 58% | 77% | 56% | 58% | 77% | 56% | 58% | nd | 49% |
| Cutoff 2 | 0.888 | 2.16 | 0.888 | 0.888 | 2.16 | 0.888 | 0.604 | nd | 0.604 |
| Sens 2 | 83% | 83% | 88% | 83% | 83% | 88% | 86% | nd | 83% |
| Spec 2 | 58% | 77% | 56% | 58% | 77% | 56% | 53% | nd | 49% |
| Cutoff 3 | 0.397 | 0.397 | 0.309 | 0.397 | 0.397 | 0.309 | 0.309 | nd | 0.309 |
| Sens 3 | 92% | 100% | 100% | 92% | 100% | 100% | 100% | nd | 100% |
| Spec 3 | 40% | 31% | 31% | 40% | 31% | 31% | 32% | nd | 31% |
| Cutoff 4 | 1.42 | 1.67 | 1.49 | 1.42 | 1.67 | 1.49 | 1.42 | nd | 1.49 |
| Sens 4 | 67% | 83% | 62% | 67% | 83% | 62% | 57% | nd | 50% |
| Spec 4 | 71% | 70% | 70% | 71% | 70% | 70% | 71% | nd | 70% |
| Cutoff 5 | 2.04 | 2.74 | 2.04 | 2.04 | 2.74 | 2.04 | 2.04 | nd | 2.04 |
| Sens 5 | 67% | 67% | 62% | 67% | 67% | 62% | 57% | nd | 50% |
| Spec 5 | 80% | 80% | 80% | 80% | 80% | 80% | 80% | nd | 80% |
| Cutoff 6 | 3.88 | 5.61 | 3.76 | 3.88 | 5.61 | 3.76 | 3.88 | nd | 3.76 |
| Sens 6 | 50% | 67% | 50% | 50% | 67% | 50% | 29% | nd | 33% |
| Spec 6 | 90% | 90% | 91% | 90% | 90% | 91% | 90% | nd | 91% |
| OR Quart 2 | >2.1 | >1.0 | >1.0 | >2.1 | >1.0 | >1.0 | >1.0 | nd | >2.2 |
| p Value | <0.56 | <0.99 | <1.0 | <0.56 | <0.99 | <1.0 | <0.98 | nd | <0.53 |
| 95% CI of | >0.18 | >0.062 | >0.059 | >0.18 | >0.062 | >0.059 | >0.062 | nd | >0.18 |
| OR Quart2 | na | na | na | na | na | na | na | nd | na |
| OR Quart 3 | >2.2 | >1.0 | >2.1 | >2.2 | >1.0 | >2.1 | >2.2 | nd | >1.0 |
| p Value | <0.54 | <0.99 | <0.56 | <0.54 | <0.99 | <0.56 | <0.54 | nd | <0.98 |
| 95% CI of | >0.18 | >0.062 | >0.18 | >0.18 | >0.062 | >0.18 | >0.18 | nd | >0.062 |

TABLE 3-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| | | | | | | | | | |
|---|---|---|---|---|---|---|---|---|---|
| OR Quart3 | na | na | na | na | na | na | na | nd | na |
| OR Quart 4 | >11 | >4.4 | >6.1 | >11 | >4.4 | >6.1 | >4.5 | nd | >3.3 |
| p Value | <0.031 | <0.19 | <0.11 | <0.031 | <0.19 | <0.11 | <0.19 | nd | <0.32 |
| 95% CI of | >1.2 | >0.47 | >0.65 | >1.2 | >0.47 | >0.65 | >0.47 | nd | >0.32 |
| OR Quart4 | na | na | na | na | na | na | na | nd | na |

Dipeptidyl peptidase IV

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | Cohort 1 | Cohort 2 | Cohort 1 | Cohort 2 | Cohort 1 | Cohort 2 |
|---|---|---|---|---|---|---|
| Median | 143 | 2270 | 143 | 2270 | 143 | 2270 |
| Average | 9210 | 2860 | 9210 | 2860 | 9210 | 2490 |
| Stdev | 74700 | 2490 | 74700 | 2490 | 74700 | 2330 |
| p(t-test) | | 0.79 | | 0.79 | | 0.83 |
| Min | 0.200 | 0.651 | 0.200 | 0.651 | 0.200 | 10.1 |
| Max | 677000 | 7150 | 677000 | 7150 | 677000 | 5420 |
| n (Samp) | 82 | 10 | 82 | 10 | 82 | 6 |
| n (Patient) | 82 | 10 | 82 | 10 | 82 | 6 |

UO only

| | Cohort 1 | Cohort 2 | Cohort 1 | Cohort 2 | Cohort 1 | Cohort 2 |
|---|---|---|---|---|---|---|
| Median | 103 | 2270 | 103 | 2270 | nd | nd |
| Average | 604 | 2720 | 604 | 2720 | nd | nd |
| Stdev | 1400 | 2100 | 1400 | 2100 | nd | nd |
| p(t-test) | | 1.0E−3 | | 1.0E−3 | nd | nd |
| Min | 0.200 | 10.1 | 0.200 | 10.1 | nd | nd |
| Max | 9980 | 5420 | 9980 | 5420 | nd | nd |
| n (Samp) | 71 | 6 | 71 | 6 | nd | nd |
| n (Patient) | 71 | 6 | 71 | 6 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.74 | nd | 0.81 | 0.74 | nd | 0.81 | 0.68 | nd | nd |
| SE | 0.094 | nd | 0.11 | 0.094 | nd | 0.11 | 0.12 | nd | nd |
| p | 0.012 | nd | 0.0037 | 0.012 | nd | 0.0037 | 0.15 | nd | nd |
| nCohort 1 | 82 | nd | 71 | 82 | nd | 71 | 82 | nd | nd |
| nCohort 2 | 10 | nd | 6 | 10 | nd | 6 | 6 | nd | nd |
| Cutoff 1 | 1210 | nd | 1190 | 1210 | nd | 1190 | 12.4 | nd | nd |
| Sens 1 | 70% | nd | 83% | 70% | nd | 83% | 83% | nd | nd |
| Spec 1 | 82% | nd | 86% | 82% | nd | 86% | 18% | nd | nd |
| Cutoff 2 | 659 | nd | 1190 | 659 | nd | 1190 | 12.4 | nd | nd |
| Sens 2 | 80% | nd | 83% | 80% | nd | 83% | 83% | nd | nd |
| Spec 2 | 73% | nd | 86% | 73% | nd | 86% | 18% | nd | nd |
| Cutoff 3 | 9.55 | nd | 9.55 | 9.55 | nd | 9.55 | 9.55 | nd | nd |
| Sens 3 | 90% | nd | 100% | 90% | nd | 100% | 100% | nd | nd |
| Spec 3 | 15% | nd | 17% | 15% | nd | 17% | 15% | nd | nd |
| Cutoff 4 | 545 | nd | 407 | 545 | nd | 407 | 545 | nd | nd |
| Sens 4 | 80% | nd | 83% | 80% | nd | 83% | 67% | nd | nd |
| Spec 4 | 71% | nd | 70% | 71% | nd | 70% | 71% | nd | nd |
| Cutoff 5 | 1190 | nd | 942 | 1190 | nd | 942 | 1190 | nd | nd |
| Sens 5 | 70% | nd | 83% | 70% | nd | 83% | 67% | nd | nd |
| Spec 5 | 80% | nd | 80% | 80% | nd | 80% | 80% | nd | nd |
| Cutoff 6 | 2020 | nd | 1810 | 2020 | nd | 1810 | 2020 | nd | nd |
| Sens 6 | 50% | nd | 67% | 50% | nd | 67% | 50% | nd | nd |
| Spec 6 | 90% | nd | 90% | 90% | nd | 90% | 90% | nd | nd |
| OR Quart 2 | 0 | nd | 0 | 0 | nd | 0 | 0 | nd | nd |
| p Value | na | nd | na | na | nd | na | na | nd | nd |
| 95% CI of | na | nd | na | na | nd | na | na | nd | nd |
| OR Quart2 | na | nd | na | na | nd | na | na | nd | nd |
| OR Quart 3 | 0.48 | nd | 0 | 0.48 | nd | 0 | 0 | nd | nd |
| p Value | 0.56 | nd | na | 0.56 | nd | na | na | nd | nd |
| 95% CI of | 0.040 | nd | na | 0.040 | nd | na | na | nd | nd |
| OR Quart3 | 5.7 | nd | na | 5.7 | nd | na | na | nd | nd |
| OR Quart 4 | 4.6 | nd | 6.0 | 4.6 | nd | 6.0 | 2.2 | nd | nd |
| p Value | 0.079 | nd | 0.12 | 0.079 | nd | 0.12 | 0.39 | nd | nd |
| 95% CI of | 0.84 | nd | 0.63 | 0.84 | nd | 0.63 | 0.36 | nd | nd |
| OR Quart4 | 25 | nd | 57 | 25 | nd | 57 | 14 | nd | nd |

TABLE 4

Comparison of marker levels in EDTA samples collected from Cohort 1 (patients that did not progress beyond RIFLE stage 0) and in EDTA samples collected from subjects at 0, 24 hours, and 48 hours prior to reaching stage R, I or F in Cohort 2.

| | Beta-2-microglobulin | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| | sCr or UO | | | | | |
| Median | 2.38 | 2.60 | 2.38 | 2.37 | 2.38 | 2.46 |
| Average | 2.90 | 3.66 | 2.90 | 3.86 | 2.90 | 3.17 |
| Stdev | 1.90 | 3.11 | 1.90 | 3.82 | 1.90 | 2.08 |
| p(t-test) | | 0.020 | | 0.0058 | | 0.49 |
| Min | 0.850 | 0.759 | 0.850 | 1.14 | 0.850 | 1.04 |
| Max | 12.1 | 16.2 | 12.1 | 22.7 | 12.1 | 9.51 |
| n (Samp) | 263 | 51 | 263 | 56 | 263 | 26 |
| n (Patient) | 111 | 51 | 111 | 56 | 111 | 26 |
| | sCr only | | | | | |
| Median | 2.38 | 4.85 | 2.38 | 4.23 | 2.38 | 4.37 |
| Average | 2.98 | 5.96 | 2.98 | 5.76 | 2.98 | 4.24 |
| Stdev | 2.03 | 4.33 | 2.03 | 5.04 | 2.03 | 2.01 |
| p(t-test) | | 1.4E−8 | | 3.7E−8 | | 0.027 |
| Min | 0.729 | 0.759 | 0.729 | 1.51 | 0.729 | 1.54 |
| Max | 16.7 | 16.2 | 16.7 | 22.7 | 16.7 | 7.60 |
| n (Samp) | 466 | 18 | 466 | 21 | 466 | 13 |
| n (Patient) | 180 | 18 | 180 | 21 | 180 | 13 |
| | UO only | | | | | |
| Median | 2.46 | 3.00 | 2.46 | 2.54 | 2.46 | 2.45 |
| Average | 2.96 | 3.80 | 2.96 | 3.78 | 2.96 | 3.41 |
| Stdev | 1.87 | 2.87 | 1.87 | 3.19 | 1.87 | 3.29 |
| p(t-test) | | 0.011 | | 0.016 | | 0.32 |
| Min | 0.899 | 1.00 | 0.899 | 1.14 | 0.899 | 1.04 |
| Max | 12.1 | 14.6 | 12.1 | 16.5 | 12.1 | 16.2 |
| n (Samp) | 221 | 50 | 221 | 52 | 221 | 23 |
| n (Patient) | 91 | 50 | 91 | 52 | 91 | 23 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.57 | 0.74 | 0.59 | 0.55 | 0.72 | 0.55 | 0.55 | 0.71 | 0.52 |
| SE | 0.045 | 0.068 | 0.046 | 0.043 | 0.064 | 0.045 | 0.061 | 0.082 | 0.064 |
| p | 0.14 | 4.4E−4 | 0.051 | 0.24 | 7.0E−4 | 0.22 | 0.45 | 0.0093 | 0.81 |
| nCohort 1 | 263 | 466 | 221 | 263 | 466 | 221 | 263 | 466 | 221 |
| nCohort 2 | 51 | 18 | 50 | 56 | 21 | 52 | 26 | 13 | 23 |
| Cutoff 1 | 1.93 | 2.86 | 2.08 | 1.80 | 2.73 | 1.88 | 2.10 | 2.45 | 1.66 |
| Sens 1 | 71% | 72% | 70% | 71% | 71% | 71% | 73% | 77% | 74% |
| Spec 1 | 37% | 62% | 38% | 32% | 60% | 33% | 41% | 52% | 27% |
| Cutoff 2 | 1.70 | 2.13 | 1.74 | 1.62 | 1.88 | 1.62 | 1.59 | 2.19 | 1.54 |
| Sens 2 | 82% | 83% | 80% | 80% | 81% | 81% | 81% | 85% | 83% |
| Spec 2 | 29% | 42% | 29% | 26% | 33% | 26% | 25% | 44% | 23% |
| Cutoff 3 | 1.40 | 1.70 | 1.59 | 1.46 | 1.76 | 1.43 | 1.37 | 1.88 | 1.37 |
| Sens 3 | 90% | 94% | 90% | 91% | 90% | 90% | 92% | 92% | 91% |
| Spec 3 | 19% | 27% | 25% | 20% | 30% | 19% | 18% | 33% | 19% |
| Cutoff 4 | 3.23 | 3.27 | 3.43 | 3.23 | 3.27 | 3.43 | 3.23 | 3.27 | 3.43 |
| Sens 4 | 37% | 67% | 40% | 32% | 67% | 35% | 35% | 62% | 35% |
| Spec 4 | 70% | 70% | 71% | 70% | 70% | 71% | 70% | 70% | 71% |
| Cutoff 5 | 3.85 | 4.11 | 4.15 | 3.85 | 4.11 | 4.15 | 3.85 | 4.11 | 4.15 |
| Sens 5 | 29% | 61% | 28% | 29% | 57% | 27% | 23% | 62% | 13% |
| Spec 5 | 80% | 80% | 80% | 80% | 80% | 80% | 80% | 80% | 80% |
| Cutoff 6 | 5.37 | 5.50 | 5.50 | 5.37 | 5.50 | 5.50 | 5.37 | 5.50 | 5.50 |
| Sens 6 | 18% | 44% | 16% | 18% | 29% | 19% | 12% | 23% | 9% |
| Spec 6 | 90% | 90% | 90% | 90% | 90% | 90% | 90% | 90% | 90% |
| OR Quart 2 | 2.4 | 3.1 | 1.8 | 1.7 | 1.5 | 1.3 | 1.2 | 2.0 | 1.5 |
| p Value | 0.077 | 0.34 | 0.23 | 0.23 | 0.66 | 0.51 | 0.75 | 0.57 | 0.54 |
| 95% CI of OR Quart2 | 0.91 | 0.31 | 0.68 | 0.73 | 0.25 | 0.56 | 0.35 | 0.18 | 0.43 |
| | 6.2 | 30 | 5.0 | 3.8 | 9.1 | 3.2 | 4.2 | 22 | 4.9 |
| OR Quart 3 | 2.0 | 2.0 | 2.4 | 0.99 | 0.99 | 0.89 | 1.2 | 2.0 | 1.0 |
| p Value | 0.16 | 0.57 | 0.073 | 0.97 | 0.99 | 0.81 | 0.75 | 0.57 | 1.0 |
| 95% CI of OR Quart3 | 0.76 | 0.18 | 0.92 | 0.40 | 0.14 | 0.35 | 0.35 | 0.18 | 0.27 |
| | 5.4 | 23 | 6.4 | 2.4 | 7.2 | 2.3 | 4.2 | 22 | 3.6 |
| OR Quart 4 | 2.6 | 13 | 2.6 | 1.7 | 7.7 | 1.7 | 1.9 | 8.4 | 1.2 |
| p Value | 0.051 | 0.014 | 0.048 | 0.23 | 0.0078 | 0.22 | 0.28 | 0.046 | 0.75 |

TABLE 4-continued

Comparison of marker levels in EDTA samples collected from Cohort 1 (patients that did not progress beyond RIFLE stage 0) and in EDTA samples collected from subjects at 0, 24 hours, and 48 hours prior to reaching stage R, I or F in Cohort 2.

| | | | | | | | | | |
|---|---|---|---|---|---|---|---|---|---|
| 95% CI of | 1.00 | 1.7 | 1.0 | 0.73 | 1.7 | 0.73 | 0.60 | 1.0 | 0.35 |
| OR Quart4 | 6.7 | 100 | 6.9 | 3.8 | 35 | 3.9 | 5.9 | 68 | 4.2 |

Renin

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | Cohort 1 | Cohort 2 | Cohort 1 | Cohort 2 | Cohort 1 | Cohort 2 |
|---|---|---|---|---|---|---|
| Median | 3630 | 3850 | 3630 | 3360 | 3630 | 4440 |
| Average | 3940 | 4030 | 3940 | 4520 | 3940 | 4580 |
| Stdev | 1330 | 1360 | 1330 | 4260 | 1330 | 2250 |
| p(t-test) | | 0.81 | | 0.37 | | 0.26 |
| Min | 1700 | 1120 | 1700 | 2100 | 1700 | 1870 |
| Max | 7950 | 6070 | 7950 | 23300 | 7950 | 8860 |
| n (Samp) | 55 | 16 | 55 | 24 | 55 | 8 |
| n (Patient) | 54 | 16 | 54 | 24 | 54 | 8 |

UO only

| | Cohort 1 | Cohort 2 | Cohort 1 | Cohort 2 | Cohort 1 | Cohort 2 |
|---|---|---|---|---|---|---|
| Median | 4180 | 3800 | 4180 | 3360 | 4180 | 4410 |
| Average | 4290 | 4040 | 4290 | 4510 | 4290 | 3960 |
| Stdev | 1610 | 1490 | 1610 | 4260 | 1610 | 1550 |
| p(t-test) | | 0.61 | | 0.75 | | 0.62 |
| Min | 1700 | 1120 | 1700 | 2100 | 1700 | 1870 |
| Max | 9230 | 6070 | 9230 | 23300 | 9230 | 6200 |
| n (Samp) | 49 | 14 | 49 | 24 | 49 | 7 |
| n (Patient) | 45 | 14 | 45 | 24 | 45 | 7 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.55 | nd | 0.48 | 0.46 | nd | 0.41 | 0.60 | nd | 0.49 |
| SE | 0.084 | nd | 0.089 | 0.072 | nd | 0.073 | 0.11 | nd | 0.12 |
| p | 0.57 | nd | 0.79 | 0.54 | nd | 0.24 | 0.36 | nd | 0.91 |
| nCohort 1 | 55 | nd | 49 | 55 | nd | 49 | 55 | nd | 49 |
| nCohort 2 | 16 | nd | 14 | 24 | nd | 24 | 8 | nd | 7 |
| Cutoff 1 | 3490 | nd | 3310 | 2630 | nd | 2630 | 3630 | nd | 3630 |
| Sens 1 | 75% | nd | 71% | 71% | nd | 71% | 75% | nd | 71% |
| Spec 1 | 45% | nd | 33% | 11% | nd | 12% | 51% | nd | 37% |
| Cutoff 2 | 2770 | nd | 2510 | 2110 | nd | 2110 | 1900 | nd | 1900 |
| Sens 2 | 81% | nd | 86% | 83% | nd | 83% | 88% | nd | 86% |
| Spec 2 | 13% | nd | 12% | 5% | nd | 6% | 5% | nd | 6% |
| Cutoff 3 | 2240 | nd | 2240 | 2100 | nd | 2100 | 1840 | nd | 1840 |
| Sens 3 | 94% | nd | 93% | 92% | nd | 92% | 100% | nd | 100% |
| Spec 3 | 9% | nd | 10% | 5% | nd | 6% | 4% | nd | 4% |
| Cutoff 4 | 4320 | nd | 4690 | 4320 | nd | 4690 | 4320 | nd | 4690 |
| Sens 4 | 44% | nd | 36% | 38% | nd | 29% | 62% | nd | 29% |
| Spec 4 | 71% | nd | 71% | 71% | nd | 71% | 71% | nd | 71% |
| Cutoff 5 | 4690 | nd | 5460 | 4690 | nd | 5460 | 4690 | nd | 5460 |
| Sens 5 | 38% | nd | 29% | 29% | nd | 21% | 38% | nd | 14% |
| Spec 5 | 80% | nd | 82% | 80% | nd | 82% | 80% | nd | 82% |
| Cutoff 6 | 5580 | nd | 6490 | 5580 | nd | 6490 | 5580 | nd | 6490 |
| Sens 6 | 12% | nd | 0% | 17% | nd | 4% | 25% | nd | 0% |
| Spec 6 | 91% | nd | 92% | 91% | nd | 92% | 91% | nd | 92% |
| OR Quart 2 | 0.65 | nd | 0.43 | 0.17 | nd | 0.43 | 0.43 | nd | 1.0 |
| p Value | 0.61 | nd | 0.37 | 0.040 | nd | 0.30 | 0.51 | nd | 1.0 |
| 95% CI of | 0.12 | nd | 0.066 | 0.030 | nd | 0.090 | 0.035 | nd | 0.12 |
| OR Quart2 | 3.5 | nd | 2.8 | 0.92 | nd | 2.1 | 5.3 | nd | 8.3 |
| OR Quart 3 | 0.65 | nd | 1.0 | 0.64 | nd | 0.83 | 0.93 | nd | 0.46 |
| p Value | 0.61 | nd | 1.0 | 0.51 | nd | 0.80 | 0.94 | nd | 0.55 |
| 95% CI of | 0.12 | nd | 0.20 | 0.17 | nd | 0.20 | 0.11 | nd | 0.037 |
| OR Quart3 | 3.5 | nd | 5.0 | 2.4 | nd | 3.4 | 7.6 | nd | 5.8 |
| OR Quart 4 | 1.6 | nd | 1.1 | 1.1 | nd | 2.7 | 1.5 | nd | 1.0 |
| p Value | 0.52 | nd | 0.92 | 0.89 | nd | 0.15 | 0.68 | nd | 1.0 |
| 95% CI of | 0.37 | nd | 0.22 | 0.30 | nd | 0.71 | 0.21 | nd | 0.12 |
| OR Quart4 | 7.2 | nd | 5.5 | 3.9 | nd | 10 | 11 | nd | 8.3 |

TABLE 4-continued

Comparison of marker levels in EDTA samples collected from Cohort 1 (patients that did not progress beyond RIFLE stage 0) and in EDTA samples collected from subjects at 0, 24 hours, and 48 hours prior to reaching stage R, I or F in Cohort 2.

Neprilysin

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.689 | 0.927 | 0.689 | 0.827 | 0.689 | 0.605 |
| Average | 1.18 | 1.27 | 1.18 | 1.20 | 1.18 | 0.816 |
| Stdev | 1.12 | 0.993 | 1.12 | 1.10 | 1.12 | 0.785 |
| p(t-test) | | 0.76 | | 0.93 | | 0.38 |
| Min | 0.0870 | 0.183 | 0.0870 | 0.191 | 0.0870 | 0.244 |
| Max | 4.92 | 3.50 | 4.92 | 4.43 | 4.92 | 2.73 |
| n (Samp) | 53 | 16 | 53 | 24 | 53 | 8 |
| n (Patient) | 52 | 16 | 52 | 24 | 52 | 8 |
| UO only | | | | | | |
| Median | 0.830 | 0.839 | 0.830 | 0.771 | 0.830 | 0.604 |
| Average | 1.35 | 1.12 | 1.35 | 1.11 | 1.35 | 0.542 |
| Stdev | 1.17 | 0.997 | 1.17 | 1.06 | 1.17 | 0.148 |
| p(t-test) | | 0.51 | | 0.40 | | 0.076 |
| Min | 0.0870 | 0.183 | 0.0870 | 0.191 | 0.0870 | 0.244 |
| Max | 4.92 | 3.50 | 4.92 | 4.43 | 4.92 | 0.684 |
| n (Samp) | 48 | 14 | 48 | 24 | 48 | 7 |
| n (Patient) | 44 | 14 | 44 | 24 | 44 | 7 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.55 | nd | 0.44 | 0.52 | nd | 0.45 | 0.40 | nd | 0.29 |
| SE | 0.084 | nd | 0.089 | 0.072 | nd | 0.073 | 0.11 | nd | 0.12 |
| p | 0.57 | nd | 0.53 | 0.80 | nd | 0.45 | 0.37 | nd | 0.063 |
| nCohort 1 | 53 | nd | 48 | 53 | nd | 48 | 53 | nd | 48 |
| nCohort 2 | 16 | nd | 14 | 24 | nd | 24 | 8 | nd | 7 |
| Cutoff 1 | 0.658 | nd | 0.510 | 0.540 | nd | 0.540 | 0.540 | nd | 0.540 |
| Sens 1 | 75% | nd | 71% | 71% | nd | 71% | 75% | nd | 71% |
| Spec 1 | 45% | nd | 27% | 36% | nd | 31% | 36% | nd | 31% |
| Cutoff 2 | 0.510 | nd | 0.308 | 0.340 | nd | 0.340 | 0.454 | nd | 0.454 |
| Sens 2 | 81% | nd | 86% | 83% | nd | 83% | 88% | nd | 86% |
| Spec 2 | 32% | nd | 6% | 19% | nd | 12% | 28% | nd | 25% |
| Cutoff 3 | 0.183 | nd | 0.183 | 0.319 | nd | 0.308 | 0.236 | nd | 0.0870 |
| Sens 3 | 94% | nd | 93% | 92% | nd | 92% | 100% | nd | 100% |
| Spec 3 | 2% | nd | 2% | 13% | nd | 6% | 6% | nd | 2% |
| Cutoff 4 | 1.22 | nd | 1.67 | 1.22 | nd | 1.67 | 1.22 | nd | 1.67 |
| Sens 4 | 31% | nd | 21% | 29% | nd | 21% | 12% | nd | 0% |
| Spec 4 | 72% | nd | 71% | 72% | nd | 71% | 72% | nd | 71% |
| Cutoff 5 | 1.82 | nd | 2.14 | 1.82 | nd | 2.14 | 1.82 | nd | 2.14 |
| Sens 5 | 25% | nd | 21% | 25% | nd | 12% | 12% | nd | 0% |
| Spec 5 | 81% | nd | 81% | 81% | nd | 81% | 81% | nd | 81% |
| Cutoff 6 | 3.14 | nd | 3.57 | 3.14 | nd | 3.57 | 3.14 | nd | 3.57 |
| Sens 6 | 6% | nd | 0% | 8% | nd | 4% | 0% | nd | 0% |
| Spec 6 | 91% | nd | 92% | 91% | nd | 92% | 91% | nd | 92% |
| OR Quart 2 | 1.4 | nd | 1.6 | 1.3 | nd | 1.3 | 1.1 | nd | >0 |
| p Value | 0.67 | nd | 0.60 | 0.72 | nd | 0.72 | 0.96 | nd | <na |
| 95% CI of | 0.27 | nd | 0.29 | 0.32 | nd | 0.31 | 0.061 | nd | >na |
| OR Quart2 | 7.7 | nd | 8.6 | 5.3 | nd | 5.4 | 19 | nd | na |
| OR Quart 3 | 1.4 | nd | 1.4 | 1.6 | nd | 2.1 | 7.5 | nd | >10 |
| p Value | 0.67 | nd | 0.67 | 0.49 | nd | 0.30 | 0.085 | nd | <0.044 |
| 95% CI of | 0.27 | nd | 0.27 | 0.41 | nd | 0.52 | 0.76 | nd | >1.1 |
| OR Quart3 | 7.7 | nd | 7.8 | 6.5 | nd | 8.3 | 74 | nd | na |
| OR Quart 4 | 1.8 | nd | 1.1 | 1.2 | nd | 1.0 | 1.1 | nd | >1.2 |
| p Value | 0.48 | nd | 0.93 | 0.80 | nd | 1.0 | 0.96 | nd | <0.92 |
| 95% CI of | 0.36 | nd | 0.18 | 0.30 | nd | 0.23 | 0.061 | nd | >0.066 |
| OR Quart4 | 9.1 | nd | 6.4 | 4.9 | nd | 4.3 | 19 | nd | na |

TABLE 4-continued

Comparison of marker levels in EDTA samples collected from Cohort 1 (patients that did not progress beyond RIFLE stage 0) and in EDTA samples collected from subjects at 0, 24 hours, and 48 hours prior to reaching stage R, I or F in Cohort 2.

Carbonic anhydrase IX

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 | sCr or UO

| | | | | | | |
|---|---|---|---|---|---|---|
| Median | 0.115 | 0.121 | 0.115 | 0.107 | 0.115 | 0.141 |
| Average | 0.155 | 0.126 | 0.155 | 0.209 | 0.155 | 0.146 |
| Stdev | 0.139 | 0.0833 | 0.139 | 0.374 | 0.139 | 0.0668 |
| p(t-test) | | 0.44 | | 0.35 | | 0.86 |
| Min | 0.0145 | 0.00992 | 0.0145 | 0.0142 | 0.0145 | 0.0579 |
| Max | 0.796 | 0.310 | 0.796 | 1.90 | 0.796 | 0.246 |
| n (Samp) | 55 | 16 | 55 | 24 | 55 | 8 |
| n (Patient) | 54 | 16 | 54 | 24 | 54 | 8 |

UO only

| | | | | | | |
|---|---|---|---|---|---|---|
| Median | 0.124 | 0.156 | 0.124 | 0.117 | 0.124 | 0.135 |
| Average | 0.170 | 0.148 | 0.170 | 0.214 | 0.170 | 0.134 |
| Stdev | 0.158 | 0.0908 | 0.158 | 0.373 | 0.158 | 0.0629 |
| p(t-test) | | 0.61 | | 0.48 | | 0.56 |
| Min | 0.0145 | 0.00992 | 0.0145 | 0.0142 | 0.0145 | 0.0579 |
| Max | 0.796 | 0.310 | 0.796 | 1.90 | 0.796 | 0.246 |
| n (Samp) | 49 | 14 | 49 | 24 | 49 | 7 |
| n (Patient) | 45 | 14 | 45 | 24 | 45 | 7 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.47 | nd | 0.51 | 0.48 | nd | 0.48 | 0.57 | nd | 0.51 |
| SE | 0.083 | nd | 0.089 | 0.071 | nd | 0.073 | 0.11 | nd | 0.12 |
| p | 0.72 | nd | 0.88 | 0.78 | nd | 0.76 | 0.56 | nd | 0.93 |
| nCohort 1 | 55 | nd | 49 | 55 | nd | 49 | 55 | nd | 49 |
| nCohort 2 | 16 | nd | 14 | 24 | nd | 24 | 8 | nd | 7 |
| Cutoff 1 | 0.0795 | nd | 0.0877 | 0.0780 | nd | 0.0780 | 0.0919 | nd | 0.0901 |
| Sens 1 | 75% | nd | 71% | 71% | nd | 71% | 75% | nd | 71% |
| Spec 1 | 27% | nd | 33% | 25% | nd | 24% | 36% | nd | 35% |
| Cutoff 2 | 0.0577 | nd | 0.0577 | 0.0665 | nd | 0.0635 | 0.0877 | nd | 0.0877 |
| Sens 2 | 81% | nd | 86% | 83% | nd | 83% | 88% | nd | 86% |
| Spec 2 | 18% | nd | 18% | 24% | nd | 20% | 33% | nd | 33% |
| Cutoff 3 | 0.0156 | nd | 0.0156 | 0.0467 | nd | 0.0467 | 0.0577 | nd | 0.0577 |
| Sens 3 | 94% | nd | 93% | 92% | nd | 92% | 100% | nd | 100% |
| Spec 3 | 4% | nd | 4% | 15% | nd | 12% | 18% | nd | 18% |
| Cutoff 4 | 0.166 | nd | 0.212 | 0.166 | nd | 0.212 | 0.166 | nd | 0.212 |
| Sens 4 | 31% | nd | 21% | 29% | nd | 29% | 38% | nd | 14% |
| Spec 4 | 71% | nd | 71% | 71% | nd | 71% | 71% | nd | 71% |
| Cutoff 5 | 0.231 | nd | 0.238 | 0.231 | nd | 0.238 | 0.231 | nd | 0.238 |
| Sens 5 | 12% | nd | 21% | 29% | nd | 25% | 12% | nd | 14% |
| Spec 5 | 80% | nd | 82% | 80% | nd | 82% | 80% | nd | 82% |
| Cutoff 6 | 0.325 | nd | 0.392 | 0.325 | nd | 0.392 | 0.325 | nd | 0.392 |
| Sens 6 | 0% | nd | 0% | 8% | nd | 8% | 0% | nd | 0% |
| Spec 6 | 91% | nd | 92% | 91% | nd | 92% | 91% | nd | 92% |
| OR Quart 2 | 1.9 | nd | 0.92 | 0.62 | nd | 0.49 | 2.0 | nd | 2.2 |
| p Value | 0.43 | nd | 0.93 | 0.49 | nd | 0.33 | 0.59 | nd | 0.55 |
| 95% CI of | 0.38 | nd | 0.16 | 0.16 | nd | 0.11 | 0.16 | nd | 0.17 |
| OR Quart2 | 9.6 | nd | 5.5 | 2.4 | nd | 2.1 | 25 | nd | 27 |
| OR Quart 3 | 1.4 | nd | 1.8 | 1.0 | nd | 1.1 | 3.2 | nd | 3.5 |
| p Value | 0.67 | nd | 0.48 | 1.0 | nd | 0.90 | 0.34 | nd | 0.30 |
| 95% CI of | 0.27 | nd | 0.35 | 0.27 | nd | 0.29 | 0.30 | nd | 0.32 |
| OR Quart3 | 7.5 | nd | 9.5 | 3.7 | nd | 4.1 | 35 | nd | 39 |
| OR Quart 4 | 1.5 | nd | 0.92 | 0.66 | nd | 0.86 | 2.0 | nd | 1.0 |
| p Value | 0.61 | nd | 0.93 | 0.56 | nd | 0.82 | 0.59 | nd | 1.0 |
| 95% CI of | 0.29 | nd | 0.16 | 0.17 | nd | 0.22 | 0.16 | nd | 0.056 |
| OR Quart4 | 8.2 | nd | 5.5 | 2.6 | nd | 3.3 | 25 | nd | 18 |

TABLE 5

Comparison of marker levels in EDTA samples collected from
Cohort 1 (patients that did not progress beyond RIFLE stage 0 or R) and in EDTA
samples collected from subjects at 0, 24 hours, and 48 hours prior to reaching stage I or F in Cohort 2.
Beta-2-microglobulin

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| Median | 2.35 | 3.84 | 2.35 | 3.30 | 2.35 | 3.65 |
| Average | 2.95 | 4.81 | 2.95 | 4.65 | 2.95 | 4.18 |
| Stdev | 2.08 | 3.91 | 2.08 | 4.22 | 2.08 | 2.85 |
| p(t-test) |  | 4.1E−5 |  | 4.8E−5 |  | 0.019 |
| Min | 0.759 | 0.780 | 0.759 | 1.12 | 0.759 | 0.945 |
| Max | 16.5 | 16.7 | 16.5 | 22.7 | 16.5 | 11.3 |
| n (Samp) | 437 | 26 | 437 | 33 | 437 | 17 |
| n (Patient) | 174 | 26 | 174 | 33 | 174 | 17 |
| sCr only | | | | | | |
| Median | 2.46 | 6.68 | 2.46 | 4.26 | 2.46 | 4.60 |
| Average | 3.12 | 5.93 | 3.12 | 7.26 | 3.12 | 5.82 |
| Stdev | 2.23 | 2.51 | 2.23 | 7.08 | 2.23 | 3.55 |
| p(t-test) |  | 0.0023 |  | 2.9E−7 |  | 0.0017 |
| Min | 0.729 | 2.87 | 0.729 | 1.84 | 0.729 | 1.90 |
| Max | 16.7 | 8.27 | 16.7 | 22.7 | 16.7 | 10.6 |
| n (Samp) | 535 | 6 | 535 | 9 | 535 | 7 |
| n (Patient) | 207 | 6 | 207 | 9 | 207 | 7 |
| UO only | | | | | | |
| Median | 2.41 | 3.84 | 2.41 | 3.30 | 2.41 | 3.65 |
| Average | 3.03 | 4.81 | 3.03 | 4.24 | 3.03 | 4.32 |
| Stdev | 2.17 | 3.87 | 2.17 | 2.81 | 2.17 | 2.90 |
| p(t-test) |  | 1.7E−4 |  | 0.0039 |  | 0.019 |
| Min | 0.899 | 0.780 | 0.899 | 1.12 | 0.899 | 0.945 |
| Max | 16.5 | 16.7 | 16.5 | 11.9 | 16.5 | 11.3 |
| n (Samp) | 362 | 26 | 362 | 31 | 362 | 17 |
| n (Patient) | 140 | 26 | 140 | 31 | 140 | 17 |

|  | 0 hr prior to AKI stage | | | 24 hr prior to AKI stage | | | 48 hr prior to AKI stage | | |
| --- | --- | --- | --- | --- | --- | --- | --- | --- | --- |
|  | sCr or UO | sCr only | UO only | sCr or UO | sCr only | UO only | sCr or UO | sCr only | UO only |
| AUC | 0.69 | 0.83 | 0.69 | 0.65 | 0.72 | 0.65 | 0.65 | 0.75 | 0.66 |
| SE | 0.059 | 0.10 | 0.059 | 0.053 | 0.097 | 0.055 | 0.074 | 0.11 | 0.074 |
| P | 0.0014 | 0.0011 | 0.0017 | 0.0052 | 0.024 | 0.0056 | 0.048 | 0.018 | 0.033 |
| nCohort 1 | 437 | 535 | 362 | 437 | 535 | 362 | 437 | 535 | 362 |
| nCohort 2 | 26 | 6 | 26 | 33 | 9 | 31 | 17 | 7 | 17 |
| Cutoff 1 | 2.60 | 2.93 | 2.60 | 2.10 | 2.27 | 2.52 | 2.33 | 4.35 | 2.45 |
| Sens 1 | 73% | 83% | 73% | 73% | 78% | 71% | 71% | 71% | 71% |
| Spec 1 | 56% | 60% | 55% | 41% | 44% | 53% | 50% | 81% | 52% |
| Cutoff 2 | 2.38 | 2.93 | 2.38 | 1.88 | 1.88 | 1.96 | 1.88 | 2.19 | 2.27 |
| Sens 2 | 81% | 83% | 81% | 82% | 89% | 81% | 82% | 86% | 82% |
| Spec 2 | 50% | 60% | 49% | 33% | 31% | 36% | 33% | 42% | 45% |
| Cutoff 3 | 1.47 | 2.86 | 1.47 | 1.56 | 1.83 | 1.56 | 1.43 | 1.88 | 1.43 |
| Sens 3 | 92% | 100% | 92% | 91% | 100% | 90% | 94% | 100% | 94% |
| Spec 3 | 18% | 59% | 18% | 22% | 30% | 21% | 16% | 31% | 17% |
| Cutoff 4 | 3.17 | 3.47 | 3.31 | 3.17 | 3.47 | 3.31 | 3.17 | 3.47 | 3.31 |
| Sens 4 | 58% | 67% | 62% | 55% | 67% | 48% | 59% | 71% | 59% |
| Spec 4 | 70% | 70% | 70% | 70% | 70% | 70% | 70% | 70% | 70% |
| Cutoff 5 | 3.83 | 4.30 | 3.95 | 3.83 | 4.30 | 3.95 | 3.83 | 4.30 | 3.95 |
| Sens 5 | 50% | 67% | 42% | 45% | 44% | 45% | 41% | 71% | 35% |
| Spec 5 | 80% | 80% | 80% | 80% | 80% | 80% | 80% | 80% | 80% |
| Cutoff 6 | 5.37 | 5.58 | 5.50 | 5.37 | 5.58 | 5.50 | 5.37 | 5.58 | 5.50 |
| Sens 6 | 23% | 67% | 19% | 27% | 33% | 26% | 24% | 43% | 24% |
| Spec 6 | 90% | 90% | 90% | 90% | 90% | 90% | 90% | 90% | 90% |
| OR Quart 2 | 0.99 | >0 | 1.0 | 2.1 | >3.1 | 1.3 | 0.99 | >2.0 | 0.65 |
| p Value | 0.99 | <na | 1.0 | 0.25 | <0.33 | 0.73 | 0.99 | <0.57 | 0.64 |
| 95% CI of | 0.20 | >na | 0.20 | 0.60 | >0.32 | 0.33 | 0.20 | >0.18 | 0.11 |
| OR Quart2 | 5.0 | na | 5.1 | 7.0 | na | 4.9 | 5.0 | na | 4.0 |
| OR Quart 3 | 2.0 | >2.0 | 1.7 | 1.3 | >0 | 2.1 | 0.33 | >0 | 0.99 |
| p Value | 0.32 | <0.57 | 0.47 | 0.73 | <na | 0.24 | 0.34 | <na | 0.99 |
| 95% CI of | 0.50 | >0.18 | 0.40 | 0.33 | >na | 0.61 | 0.034 | >na | 0.19 |
| OR Quart3 | 8.3 | na | 7.3 | 4.8 | na | 7.2 | 3.2 | na | 5.0 |
| OR Quart 4 | 5.1 | >4.1 | 5.7 | 4.4 | >6.3 | 3.9 | 3.5 | >5.2 | 3.2 |
| p Value | 0.012 | <0.21 | 0.0073 | 0.0097 | <0.091 | 0.021 | 0.061 | <0.14 | 0.091 |
| 95% CI of | 1.4 | >0.45 | 1.6 | 1.4 | >0.75 | 1.2 | 0.94 | >0.59 | 0.83 |
| OR Quart4 | 18 | na | 21 | 14 | na | 12 | 13 | na | 12 |

TABLE 5-continued

Comparison of marker levels in EDTA samples collected from
Cohort 1 (patients that did not progress beyond RIFLE stage 0 or R) and in EDTA
samples collected from subjects at 0, 24 hours, and 48 hours prior to reaching stage I or F in Cohort 2.
Beta-2-microglobulin

| | Renin | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | nd | nd | 3740 | 4690 | nd | nd |
| Average | nd | nd | 4070 | 6680 | nd | nd |
| Stdev | nd | nd | 1650 | 6470 | nd | nd |
| p(t-test) | nd | nd | | 0.0015 | nd | nd |
| Min | nd | nd | 1120 | 2100 | nd | nd |
| Max | nd | nd | 10400 | 23300 | nd | nd |
| n (Samp) | nd | nd | 113 | 9 | nd | nd |
| n (Patient) | nd | nd | 92 | 9 | nd | nd |
| UO only | | | | | | |
| Median | nd | nd | 3980 | 4690 | nd | nd |
| Average | nd | nd | 4160 | 6680 | nd | nd |
| Stdev | nd | nd | 1700 | 6470 | nd | nd |
| p(t-test) | nd | nd | | 0.0035 | nd | nd |
| Min | nd | nd | 1120 | 2100 | nd | nd |
| Max | nd | nd | 10400 | 23300 | nd | nd |
| n (Samp) | nd | nd | 99 | 9 | nd | nd |
| n (Patient) | nd | nd | 77 | 9 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | nd | nd | nd | 0.64 | nd | 0.62 | nd | nd | nd |
| SE | nd | nd | nd | 0.10 | nd | 0.10 | nd | nd | nd |
| p | nd | nd | nd | 0.17 | nd | 0.25 | nd | nd | nd |
| nCohort 1 | nd | nd | nd | 113 | nd | 99 | nd | nd | nd |
| nCohort 2 | nd | nd | nd | 9 | nd | 9 | nd | nd | nd |
| Cutoff 1 | nd | nd | nd | 3620 | nd | 3580 | nd | nd | nd |
| Sens 1 | nd | nd | nd | 78% | nd | 78% | nd | nd | nd |
| Spec 1 | nd | nd | nd | 47% | nd | 41% | nd | nd | nd |
| Cutoff 2 | nd | nd | nd | 3360 | nd | 3340 | nd | nd | nd |
| Sens 2 | nd | nd | nd | 89% | nd | 89% | nd | nd | nd |
| Spec 2 | nd | nd | nd | 41% | nd | 38% | nd | nd | nd |
| Cutoff 3 | nd | nd | nd | 2100 | nd | 2100 | nd | nd | nd |
| Sens 3 | nd | nd | nd | 100% | nd | 100% | nd | nd | nd |
| Spec 3 | nd | nd | nd | 5% | nd | 6% | nd | nd | nd |
| Cutoff 4 | nd | nd | nd | 4690 | nd | 4900 | nd | nd | nd |
| Sens 4 | nd | nd | nd | 56% | nd | 33% | nd | nd | nd |
| Spec 4 | nd | nd | nd | 71% | nd | 71% | nd | nd | nd |
| Cutoff 5 | nd | nd | nd | 5340 | nd | 5480 | nd | nd | nd |
| Sens 5 | nd | nd | nd | 33% | nd | 33% | nd | nd | nd |
| Spec 5 | nd | nd | nd | 81% | nd | 81% | nd | nd | nd |
| Cutoff 6 | nd | nd | nd | 6200 | nd | 6380 | nd | nd | nd |
| Sens 6 | nd | nd | nd | 33% | nd | 22% | nd | nd | nd |
| Spec 6 | nd | nd | nd | 90% | nd | 91% | nd | nd | nd |
| OR Quart 2 | nd | nd | nd | 2.0 | nd | 3.2 | nd | nd | nd |
| p Value | nd | nd | nd | 0.58 | nd | 0.32 | nd | nd | nd |
| 95% CI of | nd | nd | nd | 0.17 | nd | 0.32 | nd | nd | nd |
| OR Quart2 | nd | nd | nd | 23 | nd | 33 | nd | nd | nd |
| OR Quart 3 | nd | nd | nd | 3.2 | nd | 2.1 | nd | nd | nd |
| p Value | nd | nd | nd | 0.32 | nd | 0.56 | nd | nd | nd |
| 95% CI of | nd | nd | nd | 0.32 | nd | 0.18 | nd | nd | nd |
| OR Quart3 | nd | nd | nd | 33 | nd | 24 | nd | nd | nd |
| OR Quart 4 | nd | nd | nd | 3.1 | nd | 3.2 | nd | nd | nd |
| p Value | nd | nd | nd | 0.34 | nd | 0.32 | nd | nd | nd |
| 95% CI of | nd | nd | nd | 0.30 | nd | 0.32 | nd | nd | nd |
| OR Quart4 | nd | nd | nd | 32 | nd | 33 | nd | nd | nd |

TABLE 6

Comparison of the maximum marker levels in EDTA samples collected from Cohort 1 (patients that did not progress beyond RIFLE stage 0) and the maximum values in EDTA samples collected from subjects between enrollment and 0, 24 hours, and 48 hours prior to reaching stage F in Cohort 2.
Beta-2-microglobulin

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| Median | 2.63 | 7.26 | 2.63 | 6.24 | 2.63 | 5.57 |
| Average | 3.24 | 8.21 | 3.24 | 7.37 | 3.24 | 5.98 |
| Stdev | 2.18 | 5.22 | 2.18 | 5.28 | 2.18 | 3.16 |
| p(t-test) |  | 3.7E−10 |  | 1.1E−7 |  | 0.0012 |
| Min | 0.951 | 2.40 | 0.951 | 2.19 | 0.951 | 2.34 |
| Max | 12.1 | 22.7 | 12.1 | 22.7 | 12.1 | 11.3 |
| n (Samp) | 111 | 16 | 111 | 16 | 111 | 8 |
| n (Patient) | 111 | 16 | 111 | 16 | 111 | 8 |
| sCr only | | | | | | |
| Median | 2.62 | 8.11 | 2.62 | 6.44 | nd | nd |
| Average | 3.34 | 9.20 | 3.34 | 8.54 | nd | nd |
| Stdev | 2.33 | 6.94 | 2.33 | 7.37 | nd | nd |
| p(t-test) |  | 5.7E−9 |  | 2.7E−7 | nd | nd |
| Min | 0.951 | 2.40 | 0.951 | 2.19 | nd | nd |
| Max | 16.7 | 22.7 | 16.7 | 22.7 | nd | nd |
| n (Samp) | 180 | 8 | 180 | 8 | nd | nd |
| n (Patient) | 180 | 8 | 180 | 8 | nd | nd |
| UO only | | | | | | |
| Median | 2.66 | 7.62 | 2.66 | 6.90 | 2.66 | 5.57 |
| Average | 3.09 | 8.36 | 3.09 | 7.55 | 3.09 | 6.46 |
| Stdev | 1.97 | 3.54 | 1.97 | 3.23 | 1.97 | 3.33 |
| p(t-test) |  | 6.8E−11 |  | 7.4E−9 |  | 2.0E−4 |
| Min | 0.951 | 3.32 | 0.951 | 2.34 | 0.951 | 2.34 |
| Max | 12.1 | 14.6 | 12.1 | 11.9 | 12.1 | 11.3 |
| n (Samp) | 91 | 10 | 91 | 10 | 91 | 6 |
| n (Patient) | 91 | 10 | 91 | 10 | 91 | 6 |

|  | 0 hr prior to AKI stage | | | 24 hr prior to AKI stage | | | 48 hr prior to AKI stage | | |
| --- | --- | --- | --- | --- | --- | --- | --- | --- | --- |
|  | sCr or UO | sCr only | UO only | sCr or UO | sCr only | UO only | sCr or UO | sCr only | UO only |
| AUC | 0.86 | 0.82 | 0.93 | 0.80 | 0.74 | 0.89 | 0.79 | nd | 0.83 |
| SE | 0.060 | 0.092 | 0.058 | 0.069 | 0.10 | 0.069 | 0.098 | nd | 0.11 |
| p | 1.6E−9 | 4.2E−4 | 1.5E−13 | 1.5E−5 | 0.018 | 2.2E−8 | 0.0035 | nd | 0.0018 |
| nCohort 1 | 111 | 180 | 91 | 111 | 180 | 91 | 111 | nd | 91 |
| nCohort 2 | 16 | 8 | 10 | 16 | 8 | 10 | 8 | nd | 6 |
| Cutoff 1 | 4.35 | 3.32 | 6.82 | 4.16 | 2.38 | 5.62 | 4.35 | nd | 4.35 |
| Sens 1 | 75% | 75% | 70% | 75% | 75% | 70% | 75% | nd | 83% |
| Spec 1 | 77% | 66% | 97% | 76% | 44% | 88% | 77% | nd | 81% |
| Cutoff 2 | 3.32 | 2.93 | 5.62 | 2.38 | 2.27 | 5.39 | 2.38 | nd | 4.35 |
| Sens 2 | 81% | 88% | 80% | 81% | 88% | 80% | 88% | nd | 83% |
| Spec 2 | 67% | 57% | 88% | 46% | 41% | 87% | 46% | nd | 81% |
| Cutoff 3 | 2.93 | 2.38 | 4.35 | 2.26 | 2.17 | 4.35 | 2.30 | nd | 2.30 |
| Sens 3 | 94% | 100% | 90% | 94% | 100% | 90% | 100% | nd | 100% |
| Spec 3 | 59% | 44% | 81% | 42% | 37% | 81% | 44% | nd | 43% |
| Cutoff 4 | 3.61 | 3.62 | 3.43 | 3.61 | 3.62 | 3.43 | 3.61 | nd | 3.43 |
| Sens 4 | 75% | 62% | 90% | 75% | 62% | 90% | 75% | nd | 83% |
| Spec 4 | 70% | 70% | 70% | 70% | 70% | 70% | 70% | nd | 70% |
| Cutoff 5 | 4.76 | 4.76 | 4.31 | 4.76 | 4.76 | 4.31 | 4.76 | nd | 4.31 |
| Sens 5 | 69% | 62% | 90% | 62% | 50% | 90% | 62% | nd | 83% |
| Spec 5 | 81% | 80% | 80% | 81% | 80% | 80% | 81% | nd | 80% |
| Cutoff 6 | 6.14 | 6.17 | 6.04 | 6.14 | 6.17 | 6.04 | 6.14 | nd | 6.04 |
| Sens 6 | 62% | 62% | 70% | 50% | 50% | 60% | 38% | nd | 33% |
| Spec 6 | 90% | 90% | 90% | 90% | 90% | 90% | 90% | nd | 90% |
| OR Quart 2 | >1.0 | >1.0 | >0 | >4.4 | >3.2 | >1.0 | >2.1 | nd | >1.0 |
| p Value | <1.0 | <0.99 | <na | <0.19 | <0.32 | <0.98 | <0.56 | nd | <0.98 |
| 95% CI of | >0.060 | >0.062 | >na | >0.47 | >0.32 | >0.062 | >0.18 | nd | >0.062 |
| OR Quart2 | na | na | na | na | na | na | na | nd | na |
| OR Quart 3 | >4.4 | >2.1 | >1.0 | >2.1 | >1.0 | >0 | >1.0 | nd | >0 |
| p Value | <0.19 | <0.55 | <0.98 | <0.56 | <0.99 | <na | <1.0 | nd | <na |
| 95% CI of | >0.47 | >0.18 | >0.062 | >0.18 | >0.062 | >na | >0.060 | nd | >na |
| OR Quart3 | na | na | na | na | na | na | na | nd | na |
| OR Quart 4 | >16 | >5.6 | >13 | >14 | >4.4 | >13 | >5.8 | nd | >6.0 |
| p Value | <0.0100 | <0.12 | <0.019 | <0.015 | <0.19 | <0.019 | <0.12 | nd | <0.11 |

TABLE 6-continued

Comparison of the maximum marker levels in EDTA samples
collected from Cohort 1 (patients that did not progress beyond RIFLE stage 0) and the
maximum values in EDTA samples collected from subjects between enrollment and 0, 24
hours, and 48 hours prior to reaching stage F in Cohort 2.
Beta-2-microglobulin

| | | | | | | | | | |
|---|---|---|---|---|---|---|---|---|---|
| 95% CI of | >1.9 | >0.63 | >1.5 | >1.7 | >0.47 | >1.5 | >0.63 | nd | >0.65 |
| OR Quart4 | na | na | na | na | na | na | na | nd | na |

TABLE 7

Comparison of marker levels in urine samples collected from Cohort
1 (patients that did not progress beyond RIFLE stage 0, R, or I) and in urine samples
collected from Cohort 2 (subjects who progress to RIFLE stage F) at 0, 24 hours, and 48
hours prior to the subject reaching RIFLE stage I.

Beta-2-microglobulin

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 1.51 | 0.990 | 1.51 | 0.202 | nd | nd |
| Average | 2.57 | 2.02 | 2.57 | 1.80 | nd | nd |
| Stdev | 2.44 | 2.22 | 2.44 | 2.59 | nd | nd |
| p(t-test) | | 0.48 | | 0.30 | nd | nd |
| Min | 0.00152 | 0.00133 | 0.00152 | 0.00212 | nd | nd |
| Max | 6.10 | 5.64 | 6.10 | 5.80 | nd | nd |
| n (Samp) | 534 | 10 | 534 | 11 | nd | nd |
| n (Patient) | 204 | 10 | 204 | 11 | nd | nd |
| UO only | | | | | | |
| Median | 1.60 | 0.480 | 1.60 | 0.163 | nd | nd |
| Average | 2.61 | 1.86 | 2.61 | 0.998 | nd | nd |
| Stdev | 2.44 | 2.11 | 2.44 | 1.98 | nd | nd |
| p(t-test) | | 0.42 | | 0.064 | nd | nd |
| Min | 0.00152 | 0.00403 | 0.00152 | 0.00212 | nd | nd |
| Max | 6.10 | 4.76 | 6.10 | 5.80 | nd | nd |
| n (Samp) | 454 | 7 | 454 | 8 | nd | nd |
| n (Patient) | 168 | 7 | 168 | 8 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.40 | nd | 0.38 | 0.40 | nd | 0.29 | nd | nd | nd |
| SE | 0.096 | nd | 0.11 | 0.091 | nd | 0.10 | nd | nd | nd |
| p | 0.29 | nd | 0.31 | 0.25 | nd | 0.044 | nd | nd | nd |
| nCohort 1 | 534 | nd | 454 | 534 | nd | 454 | nd | nd | nd |
| nCohort 2 | 10 | nd | 7 | 11 | nd | 8 | nd | nd | nd |
| Cutoff 1 | 0.260 | nd | 0.214 | 0.153 | nd | 0.0999 | nd | nd | nd |
| Sens 1 | 70% | nd | 71% | 73% | nd | 75% | nd | nd | nd |
| Spec 1 | 28% | nd | 25% | 22% | nd | 17% | nd | nd | nd |
| Cutoff 2 | 0.0899 | nd | 0.0899 | 0.100 | nd | 0.0301 | nd | nd | nd |
| Sens 2 | 80% | nd | 86% | 82% | nd | 88% | nd | nd | nd |
| Spec 2 | 17% | nd | 16% | 18% | nd | 7% | nd | nd | nd |
| Cutoff 3 | 0.00347 | nd | 0.00347 | 0.0319 | nd | 0.00181 | nd | nd | nd |
| Sens 3 | 90% | nd | 100% | 91% | nd | 100% | nd | nd | nd |
| Spec 3 | 1% | nd | 1% | 7% | nd | 0% | nd | nd | nd |
| Cutoff 4 | 5.13 | nd | 5.20 | 5.13 | nd | 5.20 | nd | nd | nd |
| Sens 4 | 10% | nd | 0% | 27% | nd | 12% | nd | nd | nd |
| Spec 4 | 70% | nd | 70% | 70% | nd | 70% | nd | nd | nd |
| Cutoff 5 | 5.80 | nd | 5.80 | 5.80 | nd | 5.80 | nd | nd | nd |
| Sens 5 | 0% | nd | 0% | 0% | nd | 0% | nd | nd | nd |
| Spec 5 | 95% | nd | 94% | 95% | nd | 94% | nd | nd | nd |
| Cutoff 6 | 5.80 | nd | 5.80 | 5.80 | nd | 5.80 | nd | nd | nd |
| Sens 6 | 0% | nd | 0% | 0% | nd | 0% | nd | nd | nd |
| Spec 6 | 95% | nd | 94% | 95% | nd | 94% | nd | nd | nd |
| OR Quart 2 | >5.2 | nd | >3.1 | 0 | nd | 0 | nd | nd | nd |
| p Value | <0.14 | nd | <0.33 | na | nd | na | nd | nd | nd |
| 95% CI of | >0.60 | nd | >0.32 | na | nd | na | nd | nd | nd |
| OR Quart2 | na | nd | na | na | nd | na | nd | nd | nd |
| OR Quart 3 | >2.0 | nd | >1.0 | 1.0 | nd | 2.0 | nd | nd | nd |
| p Value | <0.57 | nd | <0.99 | 0.99 | nd | 0.57 | nd | nd | nd |
| 95% CI of | >0.18 | nd | >0.063 | 0.20 | nd | 0.18 | nd | nd | nd |

TABLE 7-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | | | | | | | | | |
|---|---|---|---|---|---|---|---|---|---|
| OR Quart3 | na | nd | na | 5.1 | nd | 23 | nd | nd | nd |
| OR Quart 4 | >3.1 | nd | >3.1 | 1.7 | nd | 5.2 | nd | nd | nd |
| p Value | <0.33 | nd | <0.33 | 0.47 | nd | 0.13 | nd | nd | nd |
| 95% CI of | >0.32 | nd | >0.32 | 0.40 | nd | 0.60 | nd | nd | nd |
| OR Quart4 | na | nd | na | 7.3 | nd | 45 | nd | nd | nd |

C-X-C motif chemokine 2

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.689 | 11.6 | 0.689 | 27.9 | 0.689 | 3.59 |
| Average | 8.05 | 33.9 | 8.05 | 45.6 | 8.05 | 7.16 |
| Stdev | 22.2 | 60.3 | 22.2 | 62.5 | 22.2 | 8.31 |
| p(t-test) | | 6.7E-5 | | 3.2E-10 | | 0.92 |
| Min | 0.00804 | 0.0260 | 0.00804 | 0.534 | 0.00804 | 0.0260 |
| Max | 266 | 217 | 266 | 217 | 266 | 18.5 |
| n (Samp) | 932 | 13 | 932 | 16 | 932 | 7 |
| n (Patient) | 343 | 13 | 343 | 16 | 343 | 7 |
| sCr only | | | | | | |
| Median | 0.895 | 27.8 | nd | nd | nd | nd |
| Average | 8.75 | 52.6 | nd | nd | nd | nd |
| Stdev | 23.4 | 76.5 | nd | nd | nd | nd |
| p(t-test) | | 2.0E-6 | nd | nd | nd | nd |
| Min | 0.00804 | 0.0260 | nd | nd | nd | nd |
| Max | 266 | 217 | nd | nd | nd | nd |
| n (Samp) | 969 | 7 | nd | nd | nd | nd |
| n (Patient) | 353 | 7 | nd | nd | nd | nd |
| UO only | | | | | | |
| Median | 0.805 | 9.01 | 0.805 | 28.6 | nd | nd |
| Average | 8.30 | 46.4 | 8.30 | 49.6 | nd | nd |
| Stdev | 22.4 | 75.1 | 22.4 | 66.0 | nd | nd |
| p(t-test) | | 4.9E-6 | | 1.8E-10 | nd | nd |
| Min | 0.00804 | 0.0260 | 0.00804 | 0.534 | nd | nd |
| Max | 266 | 217 | 266 | 217 | nd | nd |
| n (Samp) | 797 | 8 | 797 | 14 | nd | nd |
| n (Patient) | 260 | 8 | 260 | 14 | nd | nd |

| | 0 hr prior to AKI stage | | | 24hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.63 | 0.73 | 0.62 | 0.83 | nd | 0.82 | 0.59 | nd | nd |
| SE | 0.084 | 0.11 | 0.11 | 0.064 | nd | 0.069 | 0.11 | nd | nd |
| p | 0.13 | 0.039 | 0.25 | 2.1E-7 | nd | 2.6E-6 | 0.44 | nd | nd |
| nCohort 1 | 932 | 969 | 797 | 932 | nd | 797 | 932 | nd | nd |
| nCohort 2 | 13 | 7 | 8 | 16 | nd | 14 | 7 | nd | nd |
| Cutoff 1 | 0.00804 | 11.6 | 0.00804 | 6.36 | nd | 11.6 | 0.135 | nd | nd |
| Sens 1 | 100% | 71% | 100% | 75% | nd | 71% | 71% | nd | nd |
| Spec 1 | 0% | 82% | 0% | 75% | nd | 83% | 43% | nd | nd |
| Cutoff 2 | 0.00804 | 0.00804 | 0.00804 | 1.64 | nd | 1.54 | 0.00804 | nd | nd |
| Sens 2 | 100% | 100% | 100% | 81% | nd | 86% | 100% | nd | nd |
| Spec 2 | 0% | 0% | 0% | 56% | nd | 54% | 0% | nd | nd |
| Cutoff 3 | 0.00804 | 0.00804 | 0.00804 | 1.45 | nd | 1.45 | 0.00804 | nd | nd |
| Sens 3 | 100% | 100% | 100% | 94% | nd | 93% | 100% | nd | nd |
| Spec 3 | 0% | 0% | 0% | 54% | nd | 53% | 0% | nd | nd |
| Cutoff 4 | 4.46 | 5.17 | 4.82 | 4.46 | nd | 4.82 | 4.46 | nd | nd |
| Sens 4 | 54% | 71% | 50% | 75% | nd | 71% | 43% | nd | nd |
| Spec 4 | 70% | 70% | 70% | 70% | nd | 70% | 70% | nd | nd |
| Cutoff 5 | 8.41 | 9.64 | 8.68 | 8.41 | nd | 8.68 | 8.41 | nd | nd |
| Sens 5 | 54% | 71% | 50% | 69% | nd | 71% | 43% | nd | nd |
| Spec 5 | 80% | 80% | 80% | 80% | nd | 80% | 80% | nd | nd |
| Cutoff 6 | 19.3 | 20.9 | 20.1 | 19.3 | nd | 20.1 | 19.3 | nd | nd |
| Sens 6 | 38% | 57% | 38% | 62% | nd | 64% | 0% | nd | nd |
| Spec 6 | 90% | 90% | 90% | 90% | nd | 90% | 90% | nd | nd |
| OR Quart 2 | 0 | >2.0 | >3.0 | >1.0 | nd | >1.0 | 0.50 | nd | nd |
| p Value | na | <0.57 | <0.34 | <1.00 | nd | <1.0 | 0.57 | nd | nd |
| 95% CI of | na | >0.18 | >0.31 | >0.062 | nd | >0.062 | 0.045 | nd | nd |
| OR Quart2 | na | na | na | na | nd | na | 5.5 | nd | nd |
| OR Quart 3 | 0.20 | >0 | >1.0 | >4.1 | nd | >3.0 | 0.50 | nd | nd |

TABLE 7-continued

Comparison of marker levels in urine samples collected from Cohort
1 (patients that did not progress beyond RIFLE stage 0, R, or I) and in urine samples
collected from Cohort 2 (subjects who progress to RIFLE stage F) at 0, 24 hours, and 48
hours prior to the subject reaching RIFLE stage I.

| | | | | | | | | | |
|---|---|---|---|---|---|---|---|---|---|
| p Value | 0.14 | <na | <1.00 | <0.21 | nd | <0.34 | 0.57 | nd | nd |
| 95% CI of | 0.023 | >na | >0.062 | >0.45 | nd | >0.31 | 0.045 | nd | nd |
| OR Quart3 | 1.7 | na | na | na | nd | na | 5.5 | nd | nd |
| OR Quart 4 | 1.4 | >5.1 | >4.1 | >12 | nd | >10 | 1.5 | nd | nd |
| p Value | 0.57 | <0.14 | <0.21 | <0.020 | nd | <0.026 | 0.66 | nd | nd |
| 95% CI of | 0.44 | >0.59 | >0.45 | >1.5 | nd | >1.3 | 0.25 | nd | nd |
| OR Quart4 | 4.5 | na | na | na | nd | na | 9.1 | nd | nd |

Renin

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 384 | 670 | 384 | 3140 | nd | nd |
| Average | 850 | 1270 | 850 | 4360 | nd | nd |
| Stdev | 1270 | 1520 | 1270 | 6140 | nd | nd |
| p(t-test) | | 0.39 | | 6.2E−11 | nd | nd |
| Min | 1.00E−9 | 78.9 | 1.00E−9 | 226 | nd | nd |
| Max | 9810 | 4050 | 9810 | 21100 | nd | nd |
| n (Samp) | 322 | 7 | 322 | 10 | nd | nd |
| n (Patient) | 188 | 7 | 188 | 10 | nd | nd |
| UO only | | | | | | |
| Median | nd | nd | 396 | 3330 | nd | nd |
| Average | nd | nd | 905 | 4940 | nd | nd |
| Stdev | nd | nd | 1320 | 6790 | nd | nd |
| p(t-test) | nd | nd | | 1.3E−10 | nd | nd |
| Min | nd | nd | 1.00E−9 | 226 | nd | nd |
| Max | nd | nd | 9810 | 21100 | nd | nd |
| n (Samp) | nd | nd | 280 | 8 | nd | nd |
| n (Patient) | nd | nd | 157 | 8 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.60 | nd | nd | 0.82 | nd | 0.81 | nd | nd | nd |
| SE | 0.11 | nd | nd | 0.083 | nd | 0.093 | nd | nd | nd |
| p | 0.38 | nd | nd | 1.3E−4 | nd | 8.4E−4 | nd | nd | nd |
| nCohort 1 | 322 | nd | nd | 322 | nd | 280 | nd | nd | nd |
| nCohort 2 | 7 | nd | nd | 10 | nd | 8 | nd | nd | nd |
| Cutoff 1 | 310 | nd | nd | 1480 | nd | 1480 | nd | nd | nd |
| Sens 1 | 71% | nd | nd | 70% | nd | 75% | nd | nd | nd |
| Spec 1 | 46% | nd | nd | 81% | nd | 80% | nd | nd | nd |
| Cutoff 2 | 97.3 | nd | nd | 667 | nd | 407 | nd | nd | nd |
| Sens 2 | 86% | nd | nd | 80% | nd | 88% | nd | nd | nd |
| Spec 2 | 24% | nd | nd | 66% | nd | 51% | nd | nd | nd |
| Cutoff 3 | 69.5 | nd | nd | 407 | nd | 225 | nd | nd | nd |
| Sens 3 | 100% | nd | nd | 90% | nd | 100% | nd | nd | nd |
| Spec 3 | 22% | nd | nd | 53% | nd | 34% | nd | nd | nd |
| Cutoff 4 | 804 | nd | nd | 804 | nd | 865 | nd | nd | nd |
| Sens 4 | 43% | nd | nd | 70% | nd | 75% | nd | nd | nd |
| Spec 4 | 70% | nd | nd | 70% | nd | 70% | nd | nd | nd |
| Cutoff 5 | 1440 | nd | nd | 1440 | nd | 1520 | nd | nd | nd |
| Sens 5 | 29% | nd | nd | 70% | nd | 62% | nd | nd | nd |
| Spec 5 | 80% | nd | nd | 80% | nd | 80% | nd | nd | nd |
| Cutoff 6 | 2280 | nd | nd | 2280 | nd | 2350 | nd | nd | nd |
| Sens 6 | 29% | nd | nd | 60% | nd | 62% | nd | nd | nd |
| Spec 6 | 90% | nd | nd | 90% | nd | 90% | nd | nd | nd |
| OR Quart 2 | 0.49 | nd | nd | >1.0 | nd | >2.1 | nd | nd | nd |
| p Value | 0.57 | nd | nd | <0.99 | nd | <0.56 | nd | nd | nd |
| 95% CI of | 0.044 | nd | nd | >0.062 | nd | >0.18 | nd | nd | nd |
| OR Quart2 | 5.6 | nd | nd | na | nd | na | nd | nd | nd |
| OR Quart 3 | 1.0 | nd | nd | >2.0 | nd | >0 | nd | nd | nd |
| p Value | 1.0 | nd | nd | <0.56 | nd | <na | nd | nd | nd |
| 95% CI of | 0.14 | nd | nd | >0.18 | nd | >na | nd | nd | nd |
| OR Quart3 | 7.3 | nd | nd | na | nd | na | nd | nd | nd |
| OR Quart 4 | 0.99 | nd | nd | >7.6 | nd | >6.5 | nd | nd | nd |
| p Value | 0.99 | nd | nd | <0.060 | nd | <0.086 | nd | nd | nd |
| 95% CI of | 0.14 | nd | nd | >0.92 | nd | >0.77 | nd | nd | nd |
| OR Quart4 | 7.2 | nd | nd | na | nd | na | nd | nd | nd |

TABLE 7-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | Cathepsin B | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 0.632 | 1.86 | 0.632 | 2.76 | nd | nd |
| Average | 2.59 | 3.31 | 2.59 | 13.5 | nd | nd |
| Stdev | 8.00 | 4.58 | 8.00 | 20.9 | nd | nd |
| p(t-test) | | 0.81 | | 9.4E−5 | nd | nd |
| Min | 1.00E−9 | 1.00E−9 | 1.00E−9 | 1.00E−9 | nd | nd |
| Max | 78.1 | 12.7 | 78.1 | 64.9 | nd | nd |
| n (Samp) | 339 | 7 | 339 | 10 | nd | nd |
| n (Patient) | 194 | 7 | 194 | 10 | nd | nd |
| UO only | | | | | | |
| Median | nd | nd | 0.726 | 2.35 | nd | nd |
| Average | nd | nd | 2.90 | 13.5 | nd | nd |
| Stdev | nd | nd | 8.59 | 23.0 | nd | nd |
| p(t-test) | nd | nd | | 0.0014 | nd | nd |
| Min | nd | nd | 1.00E−9 | 1.00E−9 | nd | nd |
| Max | nd | nd | 78.1 | 64.9 | nd | nd |
| n (Samp) | nd | nd | 295 | 8 | nd | nd |
| n (Patient) | nd | nd | 162 | 8 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.58 | nd | nd | 0.75 | nd | 0.70 | nd | nd | nd |
| SE | 0.11 | nd | nd | 0.091 | nd | 0.11 | nd | nd | nd |
| p | 0.51 | nd | nd | 0.0065 | nd | 0.059 | nd | nd | nd |
| nCohort 1 | 339 | nd | nd | 339 | nd | 295 | nd | nd | nd |
| nCohort 2 | 7 | nd | nd | 10 | nd | 8 | nd | nd | nd |
| Cutoff 1 | 0.397 | nd | nd | 1.39 | nd | 0.973 | nd | nd | nd |
| Sens 1 | 71% | nd | nd | 70% | nd | 75% | nd | nd | nd |
| Spec 1 | 38% | nd | nd | 70% | nd | 58% | nd | nd | nd |
| Cutoff 2 | 0.0840 | nd | nd | 0.973 | nd | 0.924 | nd | nd | nd |
| Sens 2 | 86% | nd | nd | 80% | nd | 88% | nd | nd | nd |
| Spec 2 | 15% | nd | nd | 60% | nd | 57% | nd | nd | nd |
| Cutoff 3 | 0 | nd | nd | 0.924 | nd | 0 | nd | nd | nd |
| Sens 3 | 100% | nd | nd | 90% | nd | 100% | nd | nd | nd |
| Spec 3 | 0% | nd | nd | 59% | nd | 0% | nd | nd | nd |
| Cutoff 4 | 1.41 | nd | nd | 1.41 | nd | 1.57 | nd | nd | nd |
| Sens 4 | 57% | nd | nd | 60% | nd | 50% | nd | nd | nd |
| Spec 4 | 70% | nd | nd | 70% | nd | 70% | nd | nd | nd |
| Cutoff 5 | 2.48 | nd | nd | 2.48 | nd | 2.74 | nd | nd | nd |
| Sens 5 | 43% | nd | nd | 50% | nd | 50% | nd | nd | nd |
| Spec 5 | 80% | nd | nd | 80% | nd | 80% | nd | nd | nd |
| Cutoff 6 | 5.07 | nd | nd | 5.07 | nd | 5.47 | nd | nd | nd |
| Sens 6 | 29% | nd | nd | 40% | nd | 38% | nd | nd | nd |
| Spec 6 | 90% | nd | nd | 90% | nd | 90% | nd | nd | nd |
| OR Quart 2 | 0.49 | nd | nd | 0 | nd | 0 | nd | nd | nd |
| p Value | 0.56 | nd | nd | na | nd | na | nd | nd | nd |
| 95% CI of | 0.043 | nd | nd | na | nd | na | nd | nd | nd |
| OR Quart2 | 5.5 | nd | nd | na | nd | na | nd | nd | nd |
| OR Quart 3 | 0.49 | nd | nd | 3.1 | nd | 3.0 | nd | nd | nd |
| p Value | 0.57 | nd | nd | 0.34 | nd | 0.34 | nd | nd | nd |
| 95% CI of | 0.044 | nd | nd | 0.31 | nd | 0.31 | nd | nd | nd |
| OR Quart3 | 5.6 | nd | nd | 30 | nd | 30 | nd | nd | nd |
| OR Quart 4 | 1.5 | nd | nd | 6.3 | nd | 4.1 | nd | nd | nd |
| p Value | 0.66 | nd | nd | 0.092 | nd | 0.21 | nd | nd | nd |
| 95% CI of | 0.24 | nd | nd | 0.74 | nd | 0.45 | nd | nd | nd |
| OR Quart4 | 9.2 | nd | nd | 53 | nd | 38 | nd | nd | nd |

TABLE 7-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | Dipeptidyl peptidase IV | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 197 | 1310 | 197 | 1010 | nd | nd |
| Average | 3440 | 2090 | 3440 | 2020 | nd | nd |
| Stdev | 42400 | 2430 | 42400 | 2600 | nd | nd |
| p(t-test) | | 0.94 | | 0.92 | nd | nd |
| Min | 0.200 | 0.651 | 0.200 | 10.1 | nd | nd |
| Max | 677000 | 5420 | 677000 | 7150 | nd | nd |
| n (Samp) | 255 | 6 | 255 | 8 | nd | nd |
| n (Patient) | 158 | 6 | 158 | 8 | nd | nd |
| UO only | | | | | | |
| Median | nd | nd | 197 | 847 | nd | nd |
| Average | nd | nd | 706 | 1390 | nd | nd |
| Stdev | nd | nd | 1510 | 1830 | nd | nd |
| p(t-test) | nd | nd | | 0.28 | nd | nd |
| Min | nd | nd | 0.200 | 10.1 | nd | nd |
| Max | nd | nd | 12500 | 4950 | nd | nd |
| n (Samp) | nd | nd | 221 | 6 | nd | nd |
| n (Patient) | nd | nd | 134 | 6 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.59 | nd | nd | 0.71 | nd | 0.67 | nd | nd | nd |
| SE | 0.12 | nd | nd | 0.10 | nd | 0.12 | nd | nd | nd |
| p | 0.49 | nd | nd | 0.049 | nd | 0.18 | nd | nd | nd |
| nCohort 1 | 255 | nd | nd | 255 | nd | 221 | nd | nd | nd |
| nCohort 2 | 6 | nd | nd | 8 | nd | 6 | nd | nd | nd |
| Cutoff 1 | 52.3 | nd | nd | 337 | nd | 294 | nd | nd | nd |
| Sens 1 | 83% | nd | nd | 75% | nd | 83% | nd | nd | nd |
| Spec 1 | 29% | nd | nd | 58% | nd | 57% | nd | nd | nd |
| Cutoff 2 | 52.3 | nd | nd | 294 | nd | 294 | nd | nd | nd |
| Sens 2 | 83% | nd | nd | 88% | nd | 83% | nd | nd | nd |
| Spec 2 | 29% | nd | nd | 56% | nd | 57% | nd | nd | nd |
| Cutoff 3 | 0.202 | nd | nd | 9.55 | nd | 9.55 | nd | nd | nd |
| Sens 3 | 100% | nd | nd | 100% | nd | 100% | nd | nd | nd |
| Spec 3 | 1% | nd | nd | 11% | nd | 12% | nd | nd | nd |
| Cutoff 4 | 623 | nd | nd | 623 | nd | 623 | nd | nd | nd |
| Sens 4 | 50% | nd | nd | 62% | nd | 50% | nd | nd | nd |
| Spec 4 | 70% | nd | nd | 70% | nd | 70% | nd | nd | nd |
| Cutoff 5 | 1020 | nd | nd | 1020 | nd | 942 | nd | nd | nd |
| Sens 5 | 50% | nd | nd | 50% | nd | 50% | nd | nd | nd |
| Spec 5 | 80% | nd | nd | 80% | nd | 80% | nd | nd | nd |
| Cutoff 6 | 1810 | nd | nd | 1810 | nd | 1580 | nd | nd | nd |
| Sens 6 | 50% | nd | nd | 25% | nd | 17% | nd | nd | nd |
| Spec 6 | 90% | nd | nd | 90% | nd | 90% | nd | nd | nd |
| OR Quart 2 | 2.0 | nd | nd | 0 | nd | 0 | nd | nd | nd |
| p Value | 0.57 | nd | nd | na | nd | na | nd | nd | nd |
| 95% CI of | 0.18 | nd | nd | na | nd | na | nd | nd | nd |
| OR Quart2 | 23 | nd | nd | na | nd | na | nd | nd | nd |
| OR Quart 3 | 0 | nd | nd | 3.0 | nd | 2.0 | nd | nd | nd |
| p Value | na | nd | nd | 0.34 | nd | 0.58 | nd | nd | nd |
| 95% CI of | na | nd | nd | 0.31 | nd | 0.18 | nd | nd | nd |
| OR Quart3 | na | nd | nd | 30 | nd | 23 | nd | nd | nd |
| OR Quart 4 | 3.0 | nd | nd | 4.1 | nd | 3.1 | nd | nd | nd |
| p Value | 0.34 | nd | nd | 0.21 | nd | 0.34 | nd | nd | nd |
| 95% CI of | 0.31 | nd | nd | 0.45 | nd | 0.31 | nd | nd | nd |
| OR Quart4 | 30 | nd | nd | 38 | nd | 30 | nd | nd | nd |

TABLE 8

Comparison of marker levels in EDTA samples collected from Cohort 1 (patients that did not progress beyond RIFLE stage 0, R, or I) and in EDTA samples collected from Cohort 2 (subjects who progress to RIFLE stage F) at 0, 24 hours, and 48 hours prior to the subject reaching RIFLE stage I.
Beta-2-microglobulin

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| Median | 2.46 | 5.00 | 2.46 | 5.64 | nd | nd |
| Average | 3.12 | 6.46 | 3.12 | 7.49 | nd | nd |
| Stdev | 2.19 | 3.84 | 2.19 | 6.07 | nd | nd |
| p(t-test) |  | 3.9E−7 |  | 1.0E−9 | nd | nd |
| Min | 0.729 | 2.19 | 0.729 | 1.52 | nd | nd |
| Max | 16.7 | 14.6 | 16.7 | 22.7 | nd | nd |
| n (Samp) | 551 | 12 | 551 | 11 | nd | nd |
| n (Patient) | 213 | 12 | 213 | 11 | nd | nd |
| UO only | | | | | | |
| Median | 2.54 | 6.19 | 2.54 | 5.64 | nd | nd |
| Average | 3.15 | 7.19 | 3.15 | 6.53 | nd | nd |
| Stdev | 2.22 | 3.93 | 2.22 | 3.65 | nd | nd |
| p(t-test) |  | 7.7E−7 |  | 1.1E−5 | nd | nd |
| Min | 0.729 | 3.32 | 0.729 | 1.52 | nd | nd |
| Max | 16.7 | 14.6 | 16.7 | 11.9 | nd | nd |
| n (Samp) | 464 | 8 | 464 | 9 | nd | nd |
| n (Patient) | 173 | 8 | 173 | 9 | nd | nd |

|  | 0 hr prior to AKI stage | | | 24 hr prior to AKI stage | | | 48 hr prior to AKI stage | | |
| --- | --- | --- | --- | --- | --- | --- | --- | --- | --- |
|  | sCr or UO | sCr only | UO only | sCr or UO | sCr only | UO only | sCr or UO | sCr only | UO only |
| AUC | 0.82 | nd | 0.88 | 0.78 | nd | 0.79 | nd | nd | nd |
| SE | 0.075 | nd | 0.079 | 0.083 | nd | 0.090 | nd | nd | nd |
| p | 1.7E−5 | nd | 1.8E−6 | 6.7E−4 | nd | 0.0011 | nd | nd | nd |
| nCohort 1 | 551 | nd | 464 | 551 | nd | 464 | nd | nd | nd |
| nCohort 2 | 12 | nd | 8 | 11 | nd | 9 | nd | nd | nd |
| Cutoff 1 | 3.81 | nd | 4.59 | 4.43 | nd | 4.43 | nd | nd | nd |
| Sens 1 | 75% | nd | 75% | 73% | nd | 78% | nd | nd | nd |
| Spec 1 | 75% | nd | 83% | 82% | nd | 82% | nd | nd | nd |
| Cutoff 2 | 3.31 | nd | 3.81 | 2.31 | nd | 2.31 | nd | nd | nd |
| Sens 2 | 83% | nd | 88% | 82% | nd | 89% | nd | nd | nd |
| Spec 2 | 68% | nd | 74% | 46% | nd | 44% | nd | nd | nd |
| Cutoff 3 | 2.93 | nd | 3.31 | 2.27 | nd | 1.51 | nd | nd | nd |
| Sens 3 | 92% | nd | 100% | 91% | nd | 100% | nd | nd | nd |
| Spec 3 | 60% | nd | 67% | 44% | nd | 18% | nd | nd | nd |
| Cutoff 4 | 3.48 | nd | 3.58 | 3.48 | nd | 3.58 | nd | nd | nd |
| Sens 4 | 75% | nd | 88% | 73% | nd | 78% | nd | nd | nd |
| Spec 4 | 70% | nd | 70% | 70% | nd | 70% | nd | nd | nd |
| Cutoff 5 | 4.31 | nd | 4.35 | 4.31 | nd | 4.35 | nd | nd | nd |
| Sens 5 | 58% | nd | 75% | 73% | nd | 78% | nd | nd | nd |
| Spec 5 | 80% | nd | 80% | 80% | nd | 80% | nd | nd | nd |
| Cutoff 6 | 5.57 | nd | 5.57 | 5.57 | nd | 5.57 | nd | nd | nd |
| Sens 6 | 42% | nd | 50% | 55% | nd | 56% | nd | nd | nd |
| Spec 6 | 90% | nd | 90% | 90% | nd | 90% | nd | nd | nd |
| OR Quart 2 | >1.0 | nd | >0 | 2.0 | nd | 1.0 | nd | nd | nd |
| p Value | <1.0 | nd | <na | 0.57 | nd | 1.0 | nd | nd | nd |
| 95% CI of | >0.062 | nd | >na | 0.18 | nd | 0.062 | nd | nd | nd |
| OR Quart2 | na | nd | na | 22 | nd | 16 | nd | nd | nd |
| OR Quart 3 | >3.0 | nd | >2.0 | 0 | nd | 0 | nd | nd | nd |
| p Value | <0.34 | nd | <0.56 | na | nd | na | nd | nd | nd |
| 95% CI of | >0.31 | nd | >0.18 | na | nd | na | nd | nd | nd |
| OR Quart3 | na | nd | na | na | nd | na | nd | nd | nd |
| OR Quart 4 | >8.4 | nd | >6.3 | 8.4 | nd | 7.3 | nd | nd | nd |
| p Value | <0.046 | nd | <0.090 | 0.047 | nd | 0.065 | nd | nd | nd |
| 95% CI of | >1.0 | nd | >0.75 | 1.0 | nd | 0.89 | nd | nd | nd |
| OR Quart4 | na | nd | na | 68 | nd | 60 | nd | nd | nd |

TABLE 9

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

Beta-2-microglobulin

|  | sCr or UO | | sCr only | | UO only | |
| --- | --- | --- | --- | --- | --- | --- |
|  | Cohort 1 | Cohort 2 | Cohort 1 | Cohort 2 | Cohort 1 | Cohort 2 |
| Median | 1.58 | 0.320 | 1.10 | 0.745 | 1.48 | 0.289 |
| Average | 2.51 | 1.59 | 2.33 | 2.38 | 2.49 | 1.43 |
| Stdev | 2.46 | 2.27 | 2.44 | 2.80 | 2.47 | 2.15 |
| p(t-test) |  | 0.046 |  | 0.95 |  | 0.034 |
| Min | 0.00152 | 0.00133 | 0.00152 | 0.00133 | 0.00152 | 0.00212 |
| Max | 6.10 | 6.07 | 6.10 | 5.80 | 6.10 | 6.07 |
| n (Samp) | 138 | 35 | 164 | 8 | 111 | 30 |
| n (Patient) | 138 | 35 | 164 | 8 | 111 | 30 |

At Enrollment

|  | sCr or UO | sCr only | UO only |
| --- | --- | --- | --- |
| AUC | 0.37 | 0.49 | 0.35 |
| SE | 0.055 | 0.11 | 0.060 |
| p | 0.017 | 0.93 | 0.014 |
| nCohort 1 | 138 | 164 | 111 |
| nCohort 2 | 35 | 8 | 30 |
| Cutoff 1 | 0.0372 | 0.255 | 0.0372 |
| Sens 1 | 71% | 75% | 70% |
| Spec 1 | 10% | 35% | 11% |
| Cutoff 2 | 0.0182 | 0.0627 | 0.0182 |
| Sens 2 | 80% | 88% | 80% |
| Spec 2 | 5% | 19% | 5% |
| Cutoff 3 | 0.00270 | 0 | 0.00408 |
| Sens 3 | 91% | 100% | 90% |
| Spec 3 | 1% | 0% | 3% |
| Cutoff 4 | 5.08 | 4.82 | 5.08 |
| Sens 4 | 20% | 38% | 17% |
| Spec 4 | 70% | 70% | 70% |
| Cutoff 5 | 5.80 | 5.80 | 5.80 |
| Sens 5 | 3% | 0% | 3% |
| Spec 5 | 95% | 95% | 95% |
| Cutoff 6 | 5.80 | 5.80 | 5.80 |
| Sens 6 | 3% | 0% | 3% |
| Spec 6 | 95% | 95% | 95% |
| OR Quart 2 | 0.70 | 0 | 1.3 |
| p Value | 0.56 | na | 0.71 |
| 95% CI of | 0.20 | na | 0.35 |
| OR Quart2 | 2.4 | na | 4.7 |
| OR Quart 3 | 1.6 | 1.0 | 1.8 |
| p Value | 0.39 | 1.0 | 0.33 |
| 95% CI of | 0.55 | 0.19 | 0.54 |
| OR Quart3 | 4.7 | 5.3 | 6.3 |
| OR Quart 4 | 2.3 | 0.65 | 2.8 |
| p Value | 0.12 | 0.65 | 0.084 |
| 95% CI of | 0.81 | 0.10 | 0.87 |
| OR Quart4 | 6.5 | 4.1 | 9.3 |

C-X-C motif chemokine 2

|  | sCr or UO | | sCr only | | UO only | |
| --- | --- | --- | --- | --- | --- | --- |
|  | Cohort 1 | Cohort 2 | Cohort 1 | Cohort 2 | Cohort 1 | Cohort 2 |
| Median | 0.129 | 5.17 | 0.279 | 17.3 | 0.137 | 4.46 |
| Average | 8.07 | 22.1 | 9.66 | 35.0 | 8.19 | 23.9 |
| Stdev | 26.5 | 45.2 | 29.3 | 59.8 | 26.5 | 47.2 |
| p(t-test) |  | 0.0012 |  | 0.0052 |  | 0.0013 |
| Min | 0.00804 | 0.0260 | 0.00804 | 0.0260 | 0.00804 | 0.0260 |
| Max | 266 | 217 | 266 | 217 | 266 | 217 |
| n (Samp) | 292 | 61 | 338 | 12 | 211 | 55 |
| n (Patient) | 292 | 61 | 338 | 12 | 211 | 55 |

TABLE 9-continued

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

|  | At Enrollment | | |
| --- | --- | --- | --- |
|  | sCr or UO | sCr only | UO only |
| AUC | 0.66 | 0.77 | 0.66 |
| SE | 0.041 | 0.081 | 0.044 |
| p | 7.9E-5 | 9.7E-4 | 1.8E-4 |
| nCohort 1 | 292 | 338 | 211 |
| nCohort 2 | 61 | 12 | 55 |
| Cutoff 1 | 0.297 | 6.27 | 0.297 |
| Sens 1 | 70% | 75% | 71% |
| Spec 1 | 54% | 75% | 54% |
| Cutoff 2 | 0.00804 | 5.62 | 0.00804 |
| Sens 2 | 100% | 83% | 100% |
| Spec 2 | 0% | 72% | 0% |
| Cutoff 3 | 0.00804 | 0.00804 | 0.00804 |
| Sens 3 | 100% | 100% | 100% |
| Spec 3 | 0% | 0% | 0% |
| Cutoff 4 | 3.89 | 4.33 | 3.95 |
| Sens 4 | 52% | 83% | 51% |
| Spec 4 | 70% | 70% | 70% |
| Cutoff 5 | 6.98 | 8.37 | 7.79 |
| Sens 5 | 43% | 67% | 44% |
| Spec 5 | 80% | 80% | 80% |
| Cutoff 6 | 16.4 | 20.5 | 14.8 |
| Sens 6 | 30% | 50% | 36% |
| Spec 6 | 90% | 90% | 90% |
| OR Quart 2 | 0.16 | 0 | 0.17 |
| p Value | 0.0046 | na | 0.0084 |
| 95% CI of | 0.044 | na | 0.047 |
| OR Quart 2 | 0.57 | na | 0.64 |
| OR Quart 3 | 0.85 | 1.0 | 1.0 |
| p Value | 0.69 | 1.0 | 1.0 |
| 95% CI of | 0.39 | 0.14 | 0.43 |
| OR Quart 3 | 1.9 | 7.3 | 2.3 |
| OR Quart 4 | 2.1 | 4.2 | 2.1 |
| p Value | 0.043 | 0.073 | 0.065 |
| 95% CI of | 1.0 | 0.88 | 0.96 |
| OR Quart 4 | 4.2 | 21 | 4.5 |

| Renin | | | | | | |
| --- | --- | --- | --- | --- | --- | --- |
|  | sCr or UO | | sCr only | | UO only | |
|  | Cohort 1 | Cohort 2 | Cohort 1 | Cohort 2 | Cohort 1 | Cohort 2 |
| Median | 346 | 1010 | nd | nd | 344 | 1250 |
| Average | 771 | 2410 | nd | nd | 800 | 2590 |
| Stdev | 1050 | 4300 | nd | nd | 1090 | 4450 |
| p(t-test) |  | 5.2E-4 | nd | nd |  | 7.8E-4 |
| Min | 1.00E-9 | 92.1 | nd | nd | 1.00E-9 | 92.1 |
| Max | 4830 | 21100 | nd | nd | 4830 | 21100 |
| n (Samp) | 109 | 24 | nd | nd | 90 | 22 |
| n (Patient) | 109 | 24 | nd | nd | 90 | 22 |

|  | At Enrollment | | |
| --- | --- | --- | --- |
|  | sCr or UO | sCr only | UO only |
| AUC | 0.70 | nd | 0.72 |
| SE | 0.064 | nd | 0.066 |
| p | 0.0018 | nd | 0.0012 |
| nCohort 1 | 109 | nd | 90 |
| nCohort 2 | 24 | nd | 22 |
| Cutoff 1 | 394 | nd | 394 |
| Sens 1 | 71% | nd | 73% |
| Spec 1 | 52% | nd | 52% |
| Cutoff 2 | 310 | nd | 346 |
| Sens 2 | 83% | nd | 82% |
| Spec 2 | 48% | nd | 51% |
| Cutoff 3 | 97.3 | nd | 114 |
| Sens 3 | 92% | nd | 91% |
| Spec 3 | 27% | nd | 28% |
| Cutoff 4 | 730 | nd | 730 |
| Sens 4 | 58% | nd | 64% |

TABLE 9-continued

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

| | | | |
|---|---|---|---|
| Spec 4 | 71% | nd | 70% |
| Cutoff 5 | 1440 | nd | 1440 |
| Sens 5 | 42% | nd | 45% |
| Spec 5 | 81% | nd | 80% |
| Cutoff 6 | 2150 | nd | 2150 |
| Sens 6 | 38% | nd | 41% |
| Spec 6 | 91% | nd | 90% |
| OR Quart 2 | 1.8 | nd | 1.8 |
| p Value | 0.46 | nd | 0.45 |
| 95% CI of | 0.39 | nd | 0.39 |
| OR Quart2 | 8.2 | nd | 8.4 |
| OR Quart 3 | 2.2 | nd | 1.4 |
| p Value | 0.29 | nd | 0.69 |
| 95% CI of | 0.51 | nd | 0.28 |
| OR Quart3 | 9.8 | nd | 6.9 |
| OR Quart 4 | 4.2 | nd | 4.6 |
| p Value | 0.045 | nd | 0.035 |
| 95% CI of | 1.0 | nd | 1.1 |
| OR Quart4 | 17 | nd | 19 |

Cathepsin B

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 0.640 | 1.39 | nd | nd | 0.760 | 1.39 |
| Average | 2.41 | 7.35 | nd | nd | 2.72 | 6.90 |
| Stdev | 5.89 | 14.4 | nd | nd | 6.66 | 14.6 |
| p(t-test) | | 0.0073 | nd | nd | | 0.046 |
| Min | 1.00E−9 | 1.00E−9 | nd | nd | 1.00E−9 | 1.00E−9 |
| Max | 51.8 | 64.9 | nd | nd | 51.8 | 64.9 |
| n (Samp) | 110 | 24 | nd | nd | 91 | 22 |
| n (Patient) | 110 | 24 | nd | nd | 91 | 22 |

At Enrollment

| | sCr or UO | sCr only | UO only |
|---|---|---|---|
| AUC | 0.64 | nd | 0.63 |
| SE | 0.066 | nd | 0.069 |
| p | 0.029 | nd | 0.061 |
| nCohort 1 | 110 | nd | 91 |
| nCohort 2 | 24 | nd | 22 |
| Cutoff 1 | 0.604 | nd | 0.604 |
| Sens 1 | 71% | nd | 73% |
| Spec 1 | 50% | nd | 47% |
| Cutoff 2 | 0.388 | nd | 0.460 |
| Sens 2 | 83% | nd | 82% |
| Spec 2 | 37% | nd | 37% |
| Cutoff 3 | 0.148 | nd | 0.148 |
| Sens 3 | 92% | nd | 91% |
| Spec 3 | 18% | nd | 18% |
| Cutoff 4 | 1.29 | nd | 1.29 |
| Sens 4 | 54% | nd | 55% |
| Spec 4 | 70% | nd | 70% |
| Cutoff 5 | 2.34 | nd | 2.34 |
| Sens 5 | 42% | nd | 41% |
| Spec 5 | 80% | nd | 80% |
| Cutoff 6 | 5.45 | nd | 7.18 |
| Sens 6 | 25% | nd | 23% |
| Spec 6 | 90% | nd | 90% |
| OR Quart 2 | 1.2 | nd | 1.0 |
| p Value | 0.76 | nd | 1.0 |
| 95% CI of | 0.30 | nd | 0.22 |
| OR Quart2 | 5.1 | nd | 4.5 |
| OR Quart 3 | 1.3 | nd | 1.3 |
| p Value | 0.72 | nd | 0.72 |
| 95% CI of | 0.31 | nd | 0.31 |
| OR Quart3 | 5.3 | nd | 5.5 |
| OR Quart 4 | 3.0 | nd | 2.7 |
| p Value | 0.090 | nd | 0.14 |
| 95% CI of | 0.84 | nd | 0.72 |
| OR Quart4 | 11 | nd | 10 |

TABLE 9-continued

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

| Neprilysin | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 1.28 | 1.52 | nd | nd | 1.28 | 1.32 |
| Average | 6.20 | 17.1 | nd | nd | 5.94 | 19.1 |
| Stdev | 16.9 | 25.3 | nd | nd | 17.0 | 26.3 |
| p(t-test) | | 0.11 | nd | nd | | 0.074 |
| Min | 0.0869 | 0.0203 | nd | nd | 0.0869 | 0.0203 |
| Max | 98.9 | 64.3 | nd | nd | 98.9 | 64.3 |
| n (Samp) | 50 | 9 | nd | nd | 42 | 8 |
| n (Patient) | 50 | 9 | nd | nd | 42 | 8 |

| | At Enrollment | | |
|---|---|---|---|
| | sCr or UO | sCr only | UO only |
| AUC | 0.57 | nd | 0.57 |
| SE | 0.11 | nd | 0.11 |
| p | 0.51 | nd | 0.53 |
| nCohort 1 | 50 | nd | 42 |
| nCohort 2 | 9 | nd | 8 |
| Cutoff 1 | 0.820 | nd | 0.820 |
| Sens 1 | 78% | nd | 75% |
| Spec 1 | 40% | nd | 43% |
| Cutoff 2 | 0.238 | nd | 0.238 |
| Sens 2 | 89% | nd | 88% |
| Spec 2 | 10% | nd | 10% |
| Cutoff 3 | 0 | nd | 0 |
| Sens 3 | 100% | nd | 100% |
| Spec 3 | 0% | nd | 0% |
| Cutoff 4 | 1.68 | nd | 1.68 |
| Sens 4 | 33% | nd | 38% |
| Spec 4 | 70% | nd | 71% |
| Cutoff 5 | 3.30 | nd | 3.50 |
| Sens 5 | 33% | nd | 38% |
| Spec 5 | 80% | nd | 81% |
| Cutoff 6 | 10.8 | nd | 10.8 |
| Sens 6 | 33% | nd | 38% |
| Spec 6 | 90% | nd | 90% |
| OR Quart 2 | 0.92 | nd | 0.91 |
| p Value | 0.94 | nd | 0.93 |
| 95% CI of | 0.11 | nd | 0.11 |
| OR Quart2 | 7.6 | nd | 7.7 |
| OR Quart 3 | 0.92 | nd | 0.45 |
| p Value | 0.94 | nd | 0.54 |
| 95% CI of | 0.11 | nd | 0.036 |
| OR Quart3 | 7.6 | nd | 5.8 |
| OR Quart 4 | 1.5 | nd | 1.5 |
| p Value | 0.69 | nd | 0.69 |
| 95% CI of | 0.21 | nd | 0.20 |
| OR Quart4 | 11 | nd | 11 |

| Carbonic anhydrase IX | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 0.0111 | 0.0219 | nd | nd | 0.0113 | 0.0232 |
| Average | 0.0193 | 0.114 | nd | nd | 0.0192 | 0.126 |
| Stdev | 0.0252 | 0.280 | nd | nd | 0.0259 | 0.297 |
| p(t-test) | | 0.018 | nd | nd | | 0.021 |
| Min | 0.000386 | 0.00345 | nd | nd | 0.00102 | 0.00345 |
| Max | 0.119 | 0.859 | nd | nd | 0.119 | 0.859 |
| n (Samp) | 50 | 9 | nd | nd | 42 | 8 |
| n (Patient) | 50 | 9 | nd | nd | 42 | 8 |

TABLE 9-continued

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

|  | At Enrollment | | |
|---|---|---|---|
|  | sCr or UO | sCr only | UO only |
| AUC | 0.70 | nd | 0.71 |
| SE | 0.10 | nd | 0.11 |
| p | 0.054 | nd | 0.058 |
| nCohort 1 | 50 | nd | 42 |
| nCohort 2 | 9 | nd | 8 |
| Cutoff 1 | 0.0179 | nd | 0.0179 |
| Sens 1 | 78% | nd | 75% |
| Spec 1 | 68% | nd | 69% |
| Cutoff 2 | 0.0121 | nd | 0.0121 |
| Sens 2 | 89% | nd | 88% |
| Spec 2 | 58% | nd | 57% |
| Cutoff 3 | 0.00296 | nd | 0.00296 |
| Sens 3 | 100% | nd | 100% |
| Spec 3 | 26% | nd | 24% |
| Cutoff 4 | 0.0205 | nd | 0.0205 |
| Sens 4 | 56% | nd | 50% |
| Spec 4 | 70% | nd | 71% |
| Cutoff 5 | 0.0284 | nd | 0.0274 |
| Sens 5 | 22% | nd | 38% |
| Spec 5 | 80% | nd | 81% |
| Cutoff 6 | 0.0421 | nd | 0.0358 |
| Sens 6 | 11% | nd | 12% |
| Spec 6 | 90% | nd | 90% |
| OR Quart 2 | 0 | nd | 0 |
| p Value | na | nd | na |
| 95% CI of | na | nd | na |
| OR Quart2 | na | nd | na |
| OR Quart 3 | 6.5 | nd | 3.7 |
| p Value | 0.11 | nd | 0.29 |
| 95% CI of | 0.65 | nd | 0.32 |
| OR Quart3 | 65 | nd | 42 |
| OR Quart 4 | 3.2 | nd | 4.9 |
| p Value | 0.33 | nd | 0.19 |
| 95% CI of | 0.30 | nd | 0.46 |
| OR Quart4 | 36 | nd | 52 |

| Dipeptidyl peptidase IV | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 130 | 793 | nd | nd | 129 | 1050 |
| Average | 513 | 1820 | nd | nd | 486 | 2010 |
| Stdev | 904 | 3030 | nd | nd | 840 | 3170 |
| p(t-test) |  | 8.5E-4 | nd | nd |  | 4.7E-4 |
| Min | 0.924 | 0.651 | nd | nd | 0.924 | 10.1 |
| Max | 5010 | 12500 | nd | nd | 5010 | 12500 |
| n (Samp) | 89 | 18 | nd | nd | 74 | 16 |
| n (Patient) | 89 | 18 | nd | nd | 74 | 16 |

|  | At Enrollment | | |
|---|---|---|---|
|  | sCr or UO | sCr only | UO only |
| AUC | 0.67 | nd | 0.71 |
| SE | 0.075 | nd | 0.078 |
| p | 0.027 | nd | 0.0079 |
| nCohort 1 | 89 | nd | 74 |
| nCohort 2 | 18 | nd | 16 |
| Cutoff 1 | 173 | nd | 161 |
| Sens 1 | 72% | nd | 75% |
| Spec 1 | 56% | nd | 57% |
| Cutoff 2 | 18.2 | nd | 48.0 |
| Sens 2 | 83% | nd | 81% |
| Spec 2 | 22% | nd | 35% |
| Cutoff 3 | 8.88 | nd | 15.1 |
| Sens 3 | 94% | nd | 94% |
| Spec 3 | 12% | nd | 22% |
| Cutoff 4 | 457 | nd | 457 |
| Sens 4 | 61% | nd | 62% |

TABLE 9-continued

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

| | | | |
|---|---|---|---|
| Spec 4 | 71% | nd | 70% |
| Cutoff 5 | 837 | nd | 698 |
| Sens 5 | 50% | nd | 56% |
| Spec 5 | 81% | nd | 81% |
| Cutoff 6 | 1810 | nd | 1810 |
| Sens 6 | 28% | nd | 31% |
| Spec 6 | 91% | nd | 91% |
| OR Quart 2 | 0.21 | nd | 0.29 |
| p Value | 0.18 | nd | 0.30 |
| 95% CI of | 0.022 | nd | 0.028 |
| OR Quart2 | 2.0 | nd | 3.0 |
| OR Quart 3 | 0.96 | nd | 1.0 |
| p Value | 0.95 | nd | 1.0 |
| 95% CI of | 0.21 | nd | 0.18 |
| OR Quart3 | 4.3 | nd | 5.6 |
| OR Quart 4 | 2.8 | nd | 4.1 |
| p Value | 0.14 | nd | 0.063 |
| 95% CI of | 0.73 | nd | 0.93 |
| OR Quart4 | 10 | nd | 18 |

TABLE 10

Comparison of marker levels in enroll EDTA samples collected from Cohort 1 (patients that did not progress beyond RIFLE stage 0 or R within 48 hrs) and in enroll EDTA samples collected from Cohort 2 (subjects reaching RIFLE stage I or F within 48 hrs). Enroll samples from patients already at stage I or F were included in Cohort 2.

| Beta-2-microglobulin | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 2.23 | 3.61 | 2.34 | 4.39 | 2.30 | 3.64 |
| Average | 3.01 | 4.59 | 3.14 | 6.99 | 2.96 | 4.13 |
| Stdev | 2.15 | 4.09 | 2.26 | 6.39 | 2.14 | 2.79 |
| p(t-test) | | 0.0018 | | 2.7E−5 | | 0.014 |
| Min | 0.824 | 1.38 | 0.824 | 2.19 | 0.824 | 1.38 |
| Max | 13.8 | 22.7 | 13.8 | 22.7 | 13.8 | 11.3 |
| n (Samp) | 139 | 36 | 165 | 9 | 110 | 31 |
| n (Patient) | 139 | 36 | 165 | 9 | 110 | 31 |

| | At Enrollment | | |
|---|---|---|---|
| | sCr or UO | sCr only | UO only |
| AUC | 0.64 | 0.79 | 0.64 |
| SE | 0.054 | 0.092 | 0.059 |
| p | 0.0077 | 0.0017 | 0.020 |
| nCohort 1 | 139 | 165 | 110 |
| nCohort 2 | 36 | 9 | 31 |
| Cutoff 1 | 2.19 | 3.52 | 2.19 |
| Sens 1 | 72% | 78% | 71% |
| Spec 1 | 49% | 71% | 47% |
| Cutoff 2 | 1.81 | 2.23 | 1.76 |
| Sens 2 | 81% | 89% | 81% |
| Spec 2 | 31% | 48% | 28% |
| Cutoff 3 | 1.51 | 2.18 | 1.50 |
| Sens 3 | 94% | 100% | 94% |
| Spec 3 | 21% | 46% | 22% |
| Cutoff 4 | 3.15 | 3.48 | 3.00 |
| Sens 4 | 53% | 78% | 55% |
| Spec 4 | 71% | 70% | 70% |
| Cutoff 5 | 4.30 | 4.41 | 4.15 |
| Sens 5 | 36% | 44% | 39% |
| Spec 5 | 81% | 80% | 80% |
| Cutoff 6 | 5.95 | 6.04 | 5.49 |
| Sens 6 | 22% | 44% | 26% |
| Spec 6 | 91% | 91% | 90% |
| OR Quart 2 | 1.2 | >2.0 | 0.81 |
| p Value | 0.80 | <0.56 | 0.74 |
| 95% CI of | 0.36 | >0.18 | 0.22 |

TABLE 10-continued

Comparison of marker levels in enroll EDTA samples collected from Cohort 1 (patients that did not progress beyond RIFLE stage 0 or R within 48 hrs) and in enroll EDTA samples collected from Cohort 2 (subjects reaching RIFLE stage I or F within 48 hrs). Enroll samples from patients already at stage I or F were included in Cohort 2.

| | | | |
|---|---|---|---|
| OR Quart2 | 3.8 | na | 2.9 |
| OR Quart 3 | 1.6 | >1.0 | 1.2 |
| p Value | 0.42 | <0.99 | 0.76 |
| 95% CI of | 0.51 | >0.062 | 0.36 |
| OR Quart3 | 4.9 | na | 4.0 |
| OR Quart 4 | 2.9 | >6.8 | 2.7 |
| p Value | 0.053 | <0.082 | 0.076 |
| 95% CI of | 0.99 | >0.78 | 0.90 |
| OR Quart4 | 8.4 | na | 8.3 |

Renin

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 3930 | 3630 | nd | nd | 4300 | 3630 |
| Average | 4190 | 5880 | nd | nd | 4310 | 5880 |
| Stdev | 1810 | 6690 | nd | nd | 1930 | 6690 |
| p(t-test) | | 0.15 | nd | nd | | 0.22 |
| Min | 1840 | 2100 | nd | nd | 1840 | 2100 |
| Max | 10400 | 23300 | nd | nd | 10400 | 23300 |
| n (Samp) | 43 | 9 | nd | nd | 36 | 9 |
| n (Patient) | 43 | 9 | nd | nd | 36 | 9 |

At Enrollment

| | sCr or UO | sCr only | UO only |
|---|---|---|---|
| AUC | 0.50 | nd | 0.48 |
| SE | 0.11 | nd | 0.11 |
| p | 0.99 | nd | 0.89 |
| nCohort 1 | 43 | nd | 36 |
| nCohort 2 | 9 | nd | 9 |
| Cutoff 1 | 2560 | nd | 2560 |
| Sens 1 | 78% | nd | 78% |
| Spec 1 | 23% | nd | 25% |
| Cutoff 2 | 2110 | nd | 2110 |
| Sens 2 | 89% | nd | 89% |
| Spec 2 | 9% | nd | 11% |
| Cutoff 3 | 2100 | nd | 2100 |
| Sens 3 | 100% | nd | 100% |
| Spec 3 | 7% | nd | 8% |
| Cutoff 4 | 4690 | nd | 4900 |
| Sens 4 | 22% | nd | 22% |
| Spec 4 | 72% | nd | 72% |
| Cutoff 5 | 5340 | nd | 5550 |
| Sens 5 | 22% | nd | 22% |
| Spec 5 | 81% | nd | 81% |
| Cutoff 6 | 6480 | nd | 6490 |
| Sens 6 | 11% | nd | 11% |
| Spec 6 | 91% | nd | 92% |
| OR Quart 2 | 1.0 | nd | 1.1 |
| p Value | 1.0 | nd | 0.92 |
| 95% CI of | 0.12 | nd | 0.13 |
| OR Quart2 | 8.4 | nd | 9.6 |
| OR Quart 3 | 1.0 | nd | 1.9 |
| p Value | 1.0 | nd | 0.54 |
| 95% CI of | 0.12 | nd | 0.25 |
| OR Quart3 | 8.4 | nd | 14 |
| OR Quart 4 | 1.6 | nd | 1.1 |
| p Value | 0.62 | nd | 0.92 |
| 95% CI of | 0.23 | nd | 0.13 |
| OR Quart4 | 12 | nd | 9.6 |

Neprilysin

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 0.607 | 0.869 | nd | nd | 0.605 | 0.869 |
| Average | 0.878 | 1.43 | nd | nd | 0.862 | 1.43 |
| Stdev | 0.838 | 1.32 | nd | nd | 0.864 | 1.32 |
| p(t-test) | | 0.12 | nd | nd | | 0.12 |

TABLE 10-continued

Comparison of marker levels in enroll EDTA samples collected from Cohort 1 (patients that did not progress beyond RIFLE stage 0 or R within 48 hrs) and in enroll EDTA samples collected from Cohort 2 (subjects reaching RIFLE stage I or F within 48 hrs). Enroll samples from patients already at stage I or F were included in Cohort 2.

| | | | | | | |
|---|---|---|---|---|---|---|
| Min | 0.0682 | 0.312 | nd | nd | 0.0682 | 0.312 |
| Max | 3.76 | 4.43 | nd | nd | 3.76 | 4.43 |
| n (Samp) | 42 | 9 | nd | nd | 36 | 9 |
| n (Patient) | 42 | 9 | nd | nd | 36 | 9 |

| | At Enrollment | | |
|---|---|---|---|
| | sCr or UO | sCr only | UO only |
| AUC | 0.66 | nd | 0.68 |
| SE | 0.11 | nd | 0.11 |
| p | 0.14 | nd | 0.095 |
| nCohort 1 | 42 | nd | 36 |
| nCohort 2 | 9 | nd | 9 |
| Cutoff 1 | 0.685 | nd | 0.684 |
| Sens 1 | 78% | nd | 78% |
| Spec 1 | 69% | nd | 72% |
| Cutoff 2 | 0.337 | nd | 0.337 |
| Sens 2 | 89% | nd | 89% |
| Spec 2 | 10% | nd | 8% |
| Cutoff 3 | 0.308 | nd | 0.308 |
| Sens 3 | 100% | nd | 100% |
| Spec 3 | 5% | nd | 6% |
| Cutoff 4 | 0.806 | nd | 0.684 |
| Sens 4 | 67% | nd | 78% |
| Spec 4 | 71% | nd | 72% |
| Cutoff 5 | 0.992 | nd | 0.821 |
| Sens 5 | 33% | nd | 67% |
| Spec 5 | 81% | nd | 81% |
| Cutoff 6 | 1.84 | nd | 1.84 |
| Sens 6 | 33% | nd | 33% |
| Spec 6 | 90% | nd | 92% |
| OR Quart 2 | 0 | nd | 0 |
| p Value | na | nd | na |
| 95% CI of | na | nd | na |
| OR Quart2 | na | nd | na |
| OR Quart 3 | 2.2 | nd | 1.0 |
| p Value | 0.42 | nd | 1.0 |
| 95% CI of | 0.33 | nd | 0.11 |
| OR Quart3 | 15 | nd | 8.7 |
| OR Quart 4 | 1.5 | nd | 3.2 |
| p Value | 0.69 | nd | 0.23 |
| 95% CI of | 0.20 | nd | 0.47 |
| OR Quart4 | 11 | nd | 22 |

Carbonic anhydrase IX

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 0.116 | 0.113 | nd | nd | 0.122 | 0.113 |
| Average | 0.145 | 0.340 | nd | nd | 0.150 | 0.340 |
| Stdev | 0.132 | 0.598 | nd | nd | 0.138 | 0.598 |
| p(t-test) | | 0.053 | nd | nd | | 0.083 |
| Min | 0.0202 | 0.0472 | nd | nd | 0.0202 | 0.0472 |
| Max | 0.657 | 1.90 | nd | nd | 0.657 | 1.90 |
| n (Samp) | 43 | 9 | nd | nd | 36 | 9 |
| n (Patient) | 43 | 9 | nd | nd | 36 | 9 |

| | At Enrollment | | |
|---|---|---|---|
| | sCr or UO | sCr only | UO only |
| AUC | 0.51 | nd | 0.49 |
| SE | 0.11 | nd | 0.11 |
| p | 0.95 | nd | 0.95 |
| nCohort 1 | 43 | nd | 36 |
| nCohort 2 | 9 | nd | 9 |
| Cutoff 1 | 0.0653 | nd | 0.0579 |
| Sens 1 | 78% | nd | 78% |
| Spec 1 | 21% | nd | 19% |
| Cutoff 2 | 0.0472 | nd | 0.0472 |
| Sens 2 | 89% | nd | 89% |
| Spec 2 | 14% | nd | 14% |
| Cutoff 3 | 0.0467 | nd | 0.0467 |

TABLE 10-continued

Comparison of marker levels in enroll EDTA samples collected from Cohort 1 (patients that did not progress beyond RIFLE stage 0 or R within 48 hrs) and in enroll EDTA samples collected from Cohort 2 (subjects reaching RIFLE stage I or F within 48 hrs). Enroll samples from patients already at stage I or F were included in Cohort 2.

| | | | |
|---|---|---|---|
| Sens 3 | 100% | nd | 100% |
| Spec 3 | 14% | nd | 14% |
| Cutoff 4 | 0.147 | nd | 0.155 |
| Sens 4 | 33% | nd | 33% |
| Spec 4 | 72% | nd | 72% |
| Cutoff 5 | 0.183 | nd | 0.183 |
| Sens 5 | 33% | nd | 33% |
| Spec 5 | 81% | nd | 81% |
| Cutoff 6 | 0.241 | nd | 0.241 |
| Sens 6 | 33% | nd | 33% |
| Spec 6 | 91% | nd | 92% |
| OR Quart 2 | 0.61 | nd | 0.30 |
| p Value | 0.62 | nd | 0.33 |
| 95% CI of | 0.083 | nd | 0.026 |
| OR Quart2 | 4.4 | nd | 3.4 |
| OR Quart 3 | 0.28 | nd | 0.67 |
| p Value | 0.30 | nd | 0.69 |
| 95% CI of | 0.025 | nd | 0.089 |
| OR Quart3 | 3.1 | nd | 5.0 |
| OR Quart 4 | 1.0 | nd | 1.1 |
| p Value | 1.0 | nd | 0.90 |
| 95% CI of | 0.16 | nd | 0.17 |
| OR Quart4 | 6.2 | nd | 7.2 |

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method for evaluating and treating renal status in a subject, comprising:
    obtaining a body fluid sample from a subject selected for evaluation based on a determination that the subject is at risk of a future or current acute renal injury;
    performing an analyte binding assay configured to detect C-X-C motif chemokine 2 by introducing the body fluid sample obtained from the subject into an assay instrument which (i) contacts all or a portion of the body fluid sample with a specific binding reagent which specifically binds C-X-C motif chemokine 2, and (ii) generates an assay result indicative of binding of C-X-C motif chemokine 2 to the specific binding reagent;
    displaying the assay result generated by the assay instrument in a human-readable form; and
    correlating the assay result to the renal status of the subject by assigning the subject to a predetermined subpopulation of individuals having a known predisposition of a future acute renal injury, the assignment made by comparing the assay result or a value derived therefrom to a threshold value obtained from a population study, wherein the threshold separates the population into a first subpopulation above the threshold which is at an increased predisposition for future acute renal injury meeting the definition of RIFLE I or F within 48 hours of the time the body fluid sample is obtained relative to a second subpopulation below the threshold; and
    treating the subject based on the predetermined subpopulation of individuals to which the subject is assigned, wherein when the assay result or value derived therefrom is above the threshold value, the subject is treated by one or more of initiating renal replacement therapy, withdrawing delivery of compounds that are known to be damaging to the kidney, delaying or avoiding procedures that are known to be damaging to the kidney, and modifying diuretic administration.

2. A method according to claim 1, wherein a plurality of assay results for a plurality of biomarkers, one of which plurality of assay results is the assay result indicative of binding of C-X-C motif chemokine 2 to the specific binding reagent, are combined using a function that converts the plurality of assay results into a single composite result, and the assay results displayed in human readable form comprise the single composite result.

3. A method according to claim 1, wherein the subject is selected for evaluation of renal status based on the pre-existence in the subject of one or more known risk factors for prerenal, intrinsic renal, or postrenal ARF.

4. A method according to claim 1, wherein the subject is selected for evaluation of renal status based on an existing diagnosis of one or more of congestive heart failure, preeclampsia, eclampsia, diabetes mellitus, hypertension, coronary artery disease, proteinuria, renal insufficiency, glomerular filtration below the normal range, cirrhosis, serum creatinine above the normal range, sepsis, injury to renal function, reduced renal function, or ARF, or based on undergoing or having undergone major vascular surgery, coronary artery bypass, or other cardiac surgery, or based on exposure to NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin.

5. A method according to claim 1, wherein the threshold separates the population into a first subpopulation above the threshold which is at an increased predisposition for future acute renal injury meeting the definition of RIFLE I or F within 24hours of the time the body fluid sample is obtained relative to a second subpopulation below the threshold.

* * * * *

SEQUENCE LISTING

<160> NUMBER OF SEQ ID NOS: 7

<210> SEQ ID NO 1
<211> LENGTH: 339
<212> TYPE: PRT
<213> ORGANISM: Homo sapiens

<400> SEQUENCE: 1

Met Trp Gln Leu Trp Ala Ser Leu Cys Cys Leu Leu Val Leu Ala Asn
1               5                   10                  15

Ala Arg Ser Arg Pro Ser Phe His Pro Leu Ser Asp Glu Leu Val Asn
            20                  25                  30

Tyr Val Asn Lys Arg Asn Thr Thr Trp Gln Ala Gly His Asn Phe Tyr

```
            35                  40                  45
Asn Val Asp Met Ser Tyr Leu Lys Arg Leu Cys Gly Thr Phe Leu Gly
 50                  55                  60
Gly Pro Lys Pro Pro Gln Arg Val Met Phe Thr Asp Leu Lys Leu
 65                  70                  75                  80
Pro Ala Ser Phe Asp Ala Arg Glu Gln Trp Pro Gln Cys Pro Thr Ile
                 85                  90                  95
Lys Glu Ile Arg Asp Gln Gly Ser Cys Gly Ser Cys Trp Ala Phe Gly
                100                 105                 110
Ala Val Glu Ala Ile Ser Asp Arg Ile Cys Ile His Thr Asn Ala His
                115                 120                 125
Val Ser Val Glu Val Ser Ala Glu Asp Leu Leu Thr Cys Cys Gly Ser
130                 135                 140
Met Cys Gly Asp Gly Cys Asn Gly Gly Tyr Pro Ala Glu Ala Trp Asn
145                 150                 155                 160
Phe Trp Thr Arg Lys Gly Leu Val Ser Gly Gly Leu Tyr Glu Ser His
                165                 170                 175
Val Gly Cys Arg Pro Tyr Ser Ile Pro Pro Cys Glu His His Val Asn
                180                 185                 190
Gly Ser Arg Pro Pro Cys Thr Gly Glu Gly Asp Thr Pro Lys Cys Ser
                195                 200                 205
Lys Ile Cys Glu Pro Gly Tyr Ser Pro Thr Tyr Lys Gln Asp Lys His
210                 215                 220
Tyr Gly Tyr Asn Ser Tyr Ser Val Ser Asn Ser Glu Lys Asp Ile Met
225                 230                 235                 240
Ala Glu Ile Tyr Lys Asn Gly Pro Val Glu Gly Ala Phe Ser Val Tyr
                245                 250                 255
Ser Asp Phe Leu Leu Tyr Lys Ser Gly Val Tyr Gln His Val Thr Gly
                260                 265                 270
Glu Met Met Gly Gly His Ala Ile Arg Ile Leu Gly Trp Gly Val Glu
                275                 280                 285
Asn Gly Thr Pro Tyr Trp Leu Val Ala Asn Ser Trp Asn Thr Asp Trp
                290                 295                 300
Gly Asp Asn Gly Phe Phe Lys Ile Leu Arg Gly Gln Asp His Cys Gly
305                 310                 315                 320
Ile Glu Ser Glu Val Val Ala Gly Ile Pro Arg Thr Asp Gln Tyr Trp
                325                 330                 335
Glu Lys Ile

<210> SEQ ID NO 2
<211> LENGTH: 406
<212> TYPE: PRT
<213> ORGANISM: Homo sapiens

<400> SEQUENCE: 2

Met Asp Gly Trp Arg Arg Met Pro Arg Trp Gly Leu Leu Leu Leu Leu
 1               5                  10                  15
Trp Gly Ser Cys Thr Phe Gly Leu Pro Thr Asp Thr Thr Thr Phe Lys
                20                  25                  30
Arg Ile Phe Leu Lys Arg Met Pro Ser Ile Arg Glu Ser Leu Lys Glu
                35                  40                  45
Arg Gly Val Asp Met Ala Arg Leu Gly Pro Glu Trp Ser Gln Pro Met
 50                  55                  60
Lys Arg Leu Thr Leu Gly Asn Thr Thr Ser Ser Val Ile Leu Thr Asn
```

```
            65                  70                  75                  80
        Tyr Met Asp Thr Gln Tyr Tyr Gly Glu Ile Gly Ile Gly Thr Pro Pro
                        85                  90                  95

Gln Thr Phe Lys Val Val Phe Asp Thr Gly Ser Ser Asn Val Trp Val
                        100                 105                 110

Pro Ser Ser Lys Cys Ser Arg Leu Tyr Thr Ala Cys Val Tyr His Lys
                        115                 120                 125

Leu Phe Asp Ala Ser Asp Ser Ser Tyr Lys His Asn Gly Thr Glu
                130                 135                 140

Leu Thr Leu Arg Tyr Ser Thr Gly Thr Val Ser Gly Phe Leu Ser Gln
        145                 150                 155                 160

Asp Ile Ile Thr Val Gly Gly Ile Thr Val Thr Gln Met Phe Gly Glu
                        165                 170                 175

Val Thr Glu Met Pro Ala Leu Pro Phe Met Leu Ala Glu Phe Asp Gly
                        180                 185                 190

Val Val Gly Met Gly Phe Ile Glu Gln Ala Ile Gly Arg Val Thr Pro
                        195                 200                 205

Ile Phe Asp Asn Ile Ile Ser Gln Gly Val Leu Lys Glu Asp Val Phe
                        210                 215                 220

Ser Phe Tyr Tyr Asn Arg Asp Ser Glu Asn Ser Gln Ser Leu Gly Gly
        225                 230                 235                 240

Gln Ile Val Leu Gly Gly Ser Asp Pro Gln His Tyr Glu Gly Asn Phe
                        245                 250                 255

His Tyr Ile Asn Leu Ile Lys Thr Gly Val Trp Gln Ile Gln Met Lys
                        260                 265                 270

Gly Val Ser Val Gly Ser Ser Thr Leu Leu Cys Glu Asp Gly Cys Leu
                        275                 280                 285

Ala Leu Val Asp Thr Gly Ala Ser Tyr Ile Ser Gly Ser Thr Ser Ser
                        290                 295                 300

Ile Glu Lys Leu Met Glu Ala Leu Gly Ala Lys Lys Arg Leu Phe Asp
        305                 310                 315                 320

Tyr Val Val Lys Cys Asn Glu Gly Pro Thr Leu Pro Asp Ile Ser Phe
                        325                 330                 335

His Leu Gly Gly Lys Glu Tyr Thr Leu Thr Ser Ala Asp Tyr Val Phe
                        340                 345                 350

Gln Glu Ser Tyr Ser Ser Lys Lys Leu Cys Thr Leu Ala Ile His Ala
                        355                 360                 365

Met Asp Ile Pro Pro Pro Thr Gly Pro Thr Trp Ala Leu Gly Ala Thr
                        370                 375                 380

Phe Ile Arg Lys Phe Tyr Thr Glu Phe Asp Arg Arg Asn Asn Arg Ile
        385                 390                 395                 400

Gly Phe Ala Leu Ala Arg
                        405

<210> SEQ ID NO 3
<211> LENGTH: 766
<212> TYPE: PRT
<213> ORGANISM: Homo sapiens

<400> SEQUENCE: 3

Met Lys Thr Pro Trp Lys Val Leu Leu Gly Leu Leu Gly Ala Ala Ala
1               5                   10                  15

Leu Val Thr Ile Ile Thr Val Pro Val Val Leu Leu Asn Lys Gly Thr
                20                  25                  30
```

```
Asp Asp Ala Thr Ala Asp Ser Arg Lys Thr Tyr Thr Leu Thr Asp Tyr
         35                  40                  45
Leu Lys Asn Thr Tyr Arg Leu Lys Leu Tyr Ser Leu Arg Trp Ile Ser
 50                  55                  60
Asp His Glu Tyr Leu Tyr Lys Gln Glu Asn Asn Ile Leu Val Phe Asn
 65                  70                  75                  80
Ala Glu Tyr Gly Asn Ser Ser Val Phe Leu Glu Asn Ser Thr Phe Asp
                 85                  90                  95
Glu Phe Gly His Ser Ile Asn Asp Tyr Ser Ile Ser Pro Asp Gly Gln
            100                 105                 110
Phe Ile Leu Leu Glu Tyr Asn Tyr Val Lys Gln Trp Arg His Ser Tyr
        115                 120                 125
Thr Ala Ser Tyr Asp Ile Tyr Asp Leu Asn Lys Arg Gln Leu Ile Thr
    130                 135                 140
Glu Glu Arg Ile Pro Asn Asn Thr Gln Trp Val Thr Trp Ser Pro Val
145                 150                 155                 160
Gly His Lys Leu Ala Tyr Val Trp Asn Asn Asp Ile Tyr Val Lys Ile
                165                 170                 175
Glu Pro Asn Leu Pro Ser Tyr Arg Ile Thr Trp Thr Gly Lys Glu Asp
            180                 185                 190
Ile Ile Tyr Asn Gly Ile Thr Asp Trp Val Tyr Glu Glu Val Phe
        195                 200                 205
Ser Ala Tyr Ser Ala Leu Trp Trp Ser Pro Asn Gly Thr Phe Leu Ala
    210                 215                 220
Tyr Ala Gln Phe Asn Asp Thr Glu Val Pro Leu Ile Glu Tyr Ser Phe
225                 230                 235                 240
Tyr Ser Asp Glu Ser Leu Gln Tyr Pro Lys Thr Val Arg Val Pro Tyr
                245                 250                 255
Pro Lys Ala Gly Ala Val Asn Pro Thr Val Lys Phe Phe Val Val Asn
            260                 265                 270
Thr Asp Ser Leu Ser Ser Val Thr Asn Ala Thr Ser Ile Gln Ile Thr
        275                 280                 285
Ala Pro Ala Ser Met Leu Ile Gly Asp His Tyr Leu Cys Asp Val Thr
    290                 295                 300
Trp Ala Thr Gln Glu Arg Ile Ser Leu Gln Trp Leu Arg Arg Ile Gln
305                 310                 315                 320
Asn Tyr Ser Val Met Asp Ile Cys Asp Tyr Asp Glu Ser Ser Gly Arg
                325                 330                 335
Trp Asn Cys Leu Val Ala Arg Gln His Ile Glu Met Ser Thr Thr Gly
            340                 345                 350
Trp Val Gly Arg Phe Arg Pro Ser Glu Pro His Phe Thr Leu Asp Gly
        355                 360                 365
Asn Ser Phe Tyr Lys Ile Ile Ser Asn Glu Glu Gly Tyr Arg His Ile
    370                 375                 380
Cys Tyr Phe Gln Ile Asp Lys Lys Asp Cys Thr Phe Ile Thr Lys Gly
385                 390                 395                 400
Thr Trp Glu Val Ile Gly Ile Glu Ala Leu Thr Ser Asp Tyr Leu Tyr
                405                 410                 415
Tyr Ile Ser Asn Glu Tyr Lys Gly Met Pro Gly Gly Arg Asn Leu Tyr
            420                 425                 430
Lys Ile Gln Leu Ser Asp Tyr Thr Lys Val Thr Cys Leu Ser Cys Glu
        435                 440                 445
Leu Asn Pro Glu Arg Cys Gln Tyr Tyr Ser Val Ser Phe Ser Lys Glu
```

```
                450                 455                 460
Ala Lys Tyr Tyr Gln Leu Arg Cys Ser Gly Pro Gly Leu Pro Leu Tyr
465                 470                 475                 480

Thr Leu His Ser Ser Val Asn Asp Lys Gly Leu Arg Val Leu Glu Asp
                485                 490                 495

Asn Ser Ala Leu Asp Lys Met Leu Gln Asn Val Gln Met Pro Ser Lys
                500                 505                 510

Lys Leu Asp Phe Ile Ile Leu Asn Glu Thr Lys Phe Trp Tyr Gln Met
                515                 520                 525

Ile Leu Pro Pro His Phe Asp Lys Ser Lys Lys Tyr Pro Leu Leu Leu
                530                 535                 540

Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
                565                 570                 575

Ser Phe Asp Gly Arg Gly Ser Gly Tyr Gln Gly Asp Lys Ile Met His
                580                 585                 590

Ala Ile Asn Arg Arg Leu Gly Thr Phe Glu Val Glu Asp Gln Ile Glu
                595                 600                 605

Ala Ala Arg Gln Phe Ser Lys Met Gly Phe Val Asp Asn Lys Arg Ile
                610                 615                 620

Ala Ile Trp Gly Trp Ser Tyr Gly Gly Tyr Val Thr Ser Met Val Leu
625                 630                 635                 640

Gly Ser Gly Ser Gly Val Phe Lys Cys Gly Ile Ala Val Ala Pro Val
                645                 650                 655

Ser Arg Trp Glu Tyr Tyr Asp Ser Val Tyr Thr Glu Arg Tyr Met Gly
                660                 665                 670

Leu Pro Thr Pro Glu Asp Asn Leu Asp His Tyr Arg Asn Ser Thr Val
                675                 680                 685

Met Ser Arg Ala Glu Asn Phe Lys Gln Val Glu Tyr Leu Leu Ile His
                690                 695                 700

Gly Thr Ala Asp Asp Asn Val His Phe Gln Gln Ser Ala Gln Ile Ser
705                 710                 715                 720

Lys Ala Leu Val Asp Val Gly Val Asp Phe Gln Ala Met Trp Tyr Thr
                725                 730                 735

Asp Glu Asp His Gly Ile Ala Ser Ser Thr Ala His Gln His Ile Tyr
                740                 745                 750

Thr His Met Ser His Phe Ile Lys Gln Cys Phe Ser Leu Pro
                755                 760                 765

<210> SEQ ID NO 4
<211> LENGTH: 750
<212> TYPE: PRT
<213> ORGANISM: Homo sapiens

<400> SEQUENCE: 4

Met Gly Lys Ser Glu Ser Gln Met Asp Ile Thr Asp Ile Asn Thr Pro
1               5                   10                  15

Lys Pro Lys Lys Lys Gln Arg Trp Thr Pro Leu Glu Ile Ser Leu Ser
                20                  25                  30

Val Leu Val Leu Leu Leu Thr Ile Ile Ala Val Thr Met Ile Ala Leu
                35                  40                  45

Tyr Ala Thr Tyr Asp Asp Gly Ile Cys Lys Ser Ser Asp Cys Ile Lys
                50                  55                  60
```

```
Ser Ala Ala Arg Leu Ile Gln Asn Met Asp Ala Thr Thr Glu Pro Cys
 65                  70                  75                  80

Thr Asp Phe Phe Lys Tyr Ala Cys Gly Gly Trp Leu Lys Arg Asn Val
                 85                  90                  95

Ile Pro Glu Thr Ser Ser Arg Tyr Gly Asn Phe Asp Ile Leu Arg Asp
            100                 105                 110

Glu Leu Glu Val Val Leu Lys Asp Val Leu Gln Gly Pro Lys Thr Glu
        115                 120                 125

Asp Ile Val Ala Val Gln Lys Ala Lys Ala Leu Tyr Arg Ser Cys Ile
    130                 135                 140

Asn Glu Ser Ala Ile Asp Ser Arg Gly Gly Glu Pro Leu Leu Lys Leu
145                 150                 155                 160

Leu Pro Asp Ile Tyr Gly Trp Pro Val Ala Thr Glu Asn Trp Glu Gln
                165                 170                 175

Lys Tyr Gly Ala Ser Trp Thr Ala Glu Lys Ala Ile Ala Gln Leu Asn
            180                 185                 190

Ser Lys Tyr Gly Lys Lys Val Leu Ile Asn Leu Phe Val Gly Thr Asp
        195                 200                 205

Asp Lys Asn Ser Val Asn His Val Ile His Ile Asp Gln Pro Arg Leu
    210                 215                 220

Gly Leu Pro Ser Arg Asp Tyr Tyr Glu Cys Thr Gly Ile Tyr Lys Glu
225                 230                 235                 240

Ala Cys Thr Ala Tyr Val Asp Phe Met Ile Ser Val Ala Arg Leu Ile
                245                 250                 255

Arg Gln Glu Glu Arg Leu Pro Ile Asp Glu Asn Gln Leu Ala Leu Glu
            260                 265                 270

Met Asn Lys Val Met Glu Leu Glu Lys Glu Ile Ala Asn Ala Thr Ala
        275                 280                 285

Lys Pro Glu Asp Arg Asn Asp Pro Met Leu Leu Tyr Asn Lys Met Thr
    290                 295                 300

Leu Ala Gln Ile Gln Asn Asn Phe Ser Leu Glu Ile Asn Gly Lys Pro
305                 310                 315                 320

Phe Ser Trp Leu Asn Phe Thr Asn Glu Ile Met Ser Thr Val Asn Ile
                325                 330                 335

Ser Ile Thr Asn Glu Glu Asp Val Val Val Tyr Ala Pro Glu Tyr Leu
            340                 345                 350

Thr Lys Leu Lys Pro Ile Leu Thr Lys Tyr Ser Ala Arg Asp Leu Gln
        355                 360                 365

Asn Leu Met Ser Trp Arg Phe Ile Met Asp Leu Val Ser Ser Leu Ser
    370                 375                 380

Arg Thr Tyr Lys Glu Ser Arg Asn Ala Phe Arg Lys Ala Leu Tyr Gly
385                 390                 395                 400

Thr Thr Ser Glu Thr Ala Thr Trp Arg Arg Cys Ala Asn Tyr Val Asn
                405                 410                 415

Gly Asn Met Glu Asn Ala Val Gly Arg Leu Tyr Val Glu Ala Ala Phe
            420                 425                 430

Ala Gly Glu Ser Lys His Val Val Glu Asp Leu Ile Ala Gln Ile Arg
        435                 440                 445

Glu Val Phe Ile Gln Thr Leu Asp Asp Leu Thr Trp Met Asp Ala Glu
    450                 455                 460

Thr Lys Lys Arg Ala Glu Glu Lys Ala Leu Ala Ile Lys Glu Arg Ile
465                 470                 475                 480

Gly Tyr Pro Asp Asp Ile Val Ser Asn Asp Asn Lys Leu Asn Asn Glu
```

```
                485                 490                 495
Tyr Leu Glu Leu Asn Tyr Lys Glu Asp Glu Tyr Phe Glu Asn Ile Ile
            500                 505                 510
Gln Asn Leu Lys Phe Ser Gln Ser Lys Gln Leu Lys Lys Leu Arg Glu
            515                 520                 525
Lys Val Asp Lys Asp Glu Trp Ile Ser Gly Ala Ala Val Val Asn Ala
530                 535                 540
Phe Tyr Ser Ser Gly Arg Asn Gln Ile Val Phe Pro Ala Gly Ile Leu
545                 550                 555                 560
Gln Pro Pro Phe Phe Ser Ala Gln Gln Ser Asn Ser Leu Asn Tyr Gly
                565                 570                 575
Gly Ile Gly Met Val Ile Gly His Glu Ile Thr His Gly Phe Asp Asp
            580                 585                 590
Asn Gly Arg Asn Phe Asn Lys Asp Gly Asp Leu Val Asp Trp Trp Thr
            595                 600                 605
Gln Gln Ser Ala Ser Asn Phe Lys Glu Gln Ser Gln Cys Met Val Tyr
            610                 615                 620
Gln Tyr Gly Asn Phe Ser Trp Asp Leu Ala Gly Gly Gln His Leu Asn
625                 630                 635                 640
Gly Ile Asn Thr Leu Gly Glu Asn Ile Ala Asp Asn Gly Gly Leu Gly
                645                 650                 655
Gln Ala Tyr Arg Ala Tyr Gln Asn Tyr Ile Lys Lys Asn Gly Glu Glu
            660                 665                 670
Lys Leu Leu Pro Gly Leu Asp Leu Asn His Lys Gln Leu Phe Phe Leu
            675                 680                 685
Asn Phe Ala Gln Val Trp Cys Gly Thr Tyr Arg Pro Glu Tyr Ala Val
            690                 695                 700
Asn Ser Ile Lys Thr Asp Val His Ser Pro Gly Asn Phe Arg Ile Ile
705                 710                 715                 720
Gly Thr Leu Gln Asn Ser Ala Glu Phe Ser Glu Ala Phe His Cys Arg
                725                 730                 735
Lys Asn Ser Tyr Met Asn Pro Glu Lys Lys Cys Arg Val Trp
            740                 745                 750

<210> SEQ ID NO 5
<211> LENGTH: 119
<212> TYPE: PRT
<213> ORGANISM: Homo sapiens

<400> SEQUENCE: 5

Met Ser Arg Ser Val Ala Leu Ala Val Leu Ala Leu Leu Ser Leu Ser
1               5                   10                  15
Gly Leu Glu Ala Ile Gln Arg Thr Pro Lys Ile Gln Val Tyr Ser Arg
            20                  25                  30
His Pro Ala Glu Asn Gly Lys Ser Asn Phe Leu Asn Cys Tyr Val Ser
        35                  40                  45
Gly Phe His Pro Ser Asp Ile Glu Val Asp Leu Leu Lys Asn Gly Glu
    50                  55                  60
Arg Ile Glu Lys Val Glu His Ser Asp Leu Ser Phe Ser Lys Asp Trp
65                  70                  75                  80
Ser Phe Tyr Leu Leu Tyr Tyr Thr Glu Phe Thr Pro Thr Glu Lys Asp
                85                  90                  95
Glu Tyr Ala Cys Arg Val Asn His Val Thr Leu Ser Gln Pro Lys Ile
            100                 105                 110
```

```
Val Lys Trp Asp Arg Asp Met
        115

<210> SEQ ID NO 6
<211> LENGTH: 459
<212> TYPE: PRT
<213> ORGANISM: Homo sapiens

<400> SEQUENCE: 6

Met Ala Pro Leu Cys Pro Ser Pro Trp Leu Pro Leu Ile Pro Ala
1               5                   10                  15

Pro Ala Pro Gly Leu Thr Val Gln Leu Leu Ser Leu Leu Leu Leu
            20                  25                  30

Val Pro Val His Pro Gln Arg Leu Pro Arg Met Gln Glu Asp Ser Pro
            35                  40                  45

Leu Gly Gly Gly Ser Ser Gly Glu Asp Asp Pro Leu Gly Glu Glu Asp
    50                  55                  60

Leu Pro Ser Glu Glu Asp Ser Pro Arg Glu Glu Asp Pro Pro Gly Glu
65                  70                  75                  80

Glu Asp Leu Pro Gly Glu Glu Asp Leu Pro Gly Glu Glu Asp Leu Pro
                85                  90                  95

Glu Val Lys Pro Lys Ser Glu Glu Gly Ser Leu Lys Leu Glu Asp
            100                 105                 110

Leu Pro Thr Val Glu Ala Pro Gly Asp Pro Gln Glu Pro Gln Asn Asn
        115                 120                 125

Ala His Arg Asp Lys Glu Gly Asp Asp Gln Ser His Trp Arg Tyr Gly
    130                 135                 140

Gly Asp Pro Pro Trp Pro Arg Val Ser Pro Ala Cys Ala Gly Arg Phe
145                 150                 155                 160

Gln Ser Pro Val Asp Ile Arg Pro Gln Leu Ala Ala Phe Cys Pro Ala
                165                 170                 175

Leu Arg Pro Leu Glu Leu Leu Gly Phe Gln Leu Pro Pro Leu Pro Glu
            180                 185                 190

Leu Arg Leu Arg Asn Asn Gly His Ser Val Gln Leu Thr Leu Pro Pro
        195                 200                 205

Gly Leu Glu Met Ala Leu Gly Pro Gly Arg Glu Tyr Arg Ala Leu Gln
    210                 215                 220

Leu His Leu His Trp Gly Ala Ala Gly Arg Pro Gly Ser Glu His Thr
225                 230                 235                 240

Val Glu Gly His Arg Phe Pro Ala Glu Ile His Val Val His Leu Ser
                245                 250                 255

Thr Ala Phe Ala Arg Val Asp Glu Ala Leu Gly Arg Pro Gly Gly Leu
            260                 265                 270

Ala Val Leu Ala Ala Phe Leu Glu Glu Gly Pro Glu Glu Asn Ser Ala
        275                 280                 285

Tyr Glu Gln Leu Leu Ser Arg Leu Glu Glu Ile Ala Glu Glu Gly Ser
    290                 295                 300

Glu Thr Gln Val Pro Gly Leu Asp Ile Ser Ala Leu Leu Pro Ser Asp
305                 310                 315                 320

Phe Ser Arg Tyr Phe Gln Tyr Glu Gly Ser Leu Thr Thr Pro Pro Cys
                325                 330                 335

Ala Gln Gly Val Ile Trp Thr Val Phe Asn Gln Thr Val Met Leu Ser
            340                 345                 350

Ala Lys Gln Leu His Thr Leu Ser Asp Thr Leu Trp Gly Pro Gly Asp
        355                 360                 365
```

```
Ser Arg Leu Gln Leu Asn Phe Arg Ala Thr Gln Pro Leu Asn Gly Arg
    370                 375                 380

Val Ile Glu Ala Ser Phe Pro Ala Gly Val Asp Ser Ser Pro Arg Ala
385                 390                 395                 400

Ala Glu Pro Val Gln Leu Asn Ser Cys Leu Ala Ala Gly Asp Ile Leu
                405                 410                 415

Ala Leu Val Phe Gly Leu Leu Phe Ala Val Thr Ser Val Ala Phe Leu
                420                 425                 430

Val Gln Met Arg Arg Gln His Arg Arg Gly Thr Lys Gly Gly Val Ser
            435                 440                 445

Tyr Arg Pro Ala Glu Val Ala Glu Thr Gly Ala
    450                 455

<210> SEQ ID NO 7
<211> LENGTH: 107
<212> TYPE: PRT
<213> ORGANISM: Homo sapiens

<400> SEQUENCE: 7

Met Ala Arg Ala Thr Leu Ser Ala Ala Pro Ser Asn Pro Arg Leu Leu
1               5                   10                  15

Arg Val Ala Leu Leu Leu Leu Leu Val Ala Ala Ser Arg Arg Ala
                20                  25                  30

Ala Gly Ala Pro Leu Ala Thr Glu Leu Arg Cys Gln Cys Leu Gln Thr
            35                  40                  45

Leu Gln Gly Ile His Leu Lys Asn Ile Gln Ser Val Lys Val Lys Ser
        50                  55                  60

Pro Gly Pro His Cys Ala Gln Thr Glu Val Ile Ala Thr Leu Lys Asn
65                  70                  75                  80

Gly Gln Lys Ala Cys Leu Asn Pro Ala Ser Pro Met Val Lys Lys Ile
                85                  90                  95

Ile Glu Lys Met Leu Lys Asn Gly Lys Ser Asn
                100                 105
```